US008883888B2

(12) United States Patent
Sakamoto et al.

(10) Patent No.: US 8,883,888 B2
(45) Date of Patent: Nov. 11, 2014

(54) DIARYLAMINE COMPOUNDS, AGING INHIBITOR, POLYMER COMPOSITION, CROSSLINKED RUBBER PRODUCT AND MOLDED ARTICLE OF THE CROSSLINKED PRODUCT, AND METHOD OF PRODUCING DIARYLAMINE COMPOUND

(75) Inventors: Kei Sakamoto, Tokyo (JP); Tomonori Ogawa, Tokyo (JP); Satoshi Kiriki, Tokyo (JP); Masanobu Shinohara, Tokyo (JP); Yasushi Nakano, Tokyo (JP)

(73) Assignee: Zeon Corporation, Tokyo (JP)

( * ) Notice: Subject to any disclaimer, the term of this patent is extended or adjusted under 35 U.S.C. 154(b) by 134 days.

(21) Appl. No.: 13/381,613

(22) PCT Filed: Jun. 30, 2010

(86) PCT No.: PCT/JP2010/061199
§ 371 (c)(1),
(2), (4) Date: Dec. 29, 2011

(87) PCT Pub. No.: WO2011/002038
PCT Pub. Date: Jan. 6, 2011

(65) Prior Publication Data
US 2012/0101196 A1 Apr. 26, 2012

(30) Foreign Application Priority Data

| Jun. 30, 2009 | (JP) | 2009-156401 |
| Jun. 30, 2009 | (JP) | 2009-156402 |
| Sep. 29, 2009 | (JP) | 2009-225016 |
| Feb. 23, 2010 | (JP) | 2010-037103 |
| Jun. 15, 2010 | (JP) | 2010-135896 |

(51) Int. Cl.
*C08K 5/3417* (2006.01)
*C07D 209/56* (2006.01)
*C07D 403/04* (2006.01)
*C07D 209/48* (2006.01)
*C07D 209/72* (2006.01)
*C07D 217/24* (2006.01)
*C08K 5/18* (2006.01)

(52) U.S. Cl.
CPC ............ *C07D 217/24* (2013.01); *C07D 209/48* (2013.01); *C07D 209/72* (2013.01); *C07D 403/04* (2013.01); *C08K 5/3417* (2013.01); *C08K 5/18* (2013.01)
USPC ............... 524/89; 524/94; 548/435; 548/466; 548/476

(58) Field of Classification Search
USPC ........................ 548/435, 466, 476; 524/89, 94
See application file for complete search history.

(56) References Cited

U.S. PATENT DOCUMENTS

| 3,507,880 | A |   | 4/1970 | Altwicker |
| 4,069,209 | A | * | 1/1978 | Lange ........................... 528/289 |
| 4,463,170 | A |   | 7/1984 | Gloth et al. |
| 4,743,657 | A |   | 5/1988 | Rekers et al. |
| 4,840,868 | A |   | 6/1989 | Pawlowski et al. |
| 5,075,421 | A |   | 12/1991 | Wideman et al. |
| 5,229,484 | A |   | 7/1993 | Wolf et al. |
| 5,296,610 | A |   | 3/1994 | Wolf et al. |
| 5,420,123 | A |   | 5/1995 | Murugesan |
| 2003/0219718 | A1 |   | 11/2003 | Weber et al. |
| 2007/0142616 | A1 |   | 6/2007 | Murray et al. |
| 2008/0071014 | A1 |   | 3/2008 | Ohishi et al. |
| 2009/0227730 | A1 |   | 9/2009 | Gerster et al. |

FOREIGN PATENT DOCUMENTS

| EP | 0 152 021 | A2 | 8/1985 |
| JP | 49-110665 | A | 10/1974 |
| JP | 55-53249 | A | 4/1980 |
| JP | 59-140227 | A | 8/1984 |
| JP | 60-237064 | A | 11/1985 |
| JP | 62-190237 | A | 8/1987 |
| JP | 63-172154 | A | 7/1988 |
| JP | 3-504020 | A | 9/1991 |
| JP | 4-353520 | A | 12/1992 |
| JP | 5-53789 | B2 | 8/1993 |
| JP | 58-213049 | A | 12/1993 |
| JP | 9-53070 | A | 2/1997 |
| JP | 10-298551 | A | 11/1998 |
| JP | 11-21411 | A | 1/1999 |
| JP | 2006-508330 | A | 3/2006 |
| JP | 2009-7491 | A | 1/2009 |
| JP | 2009-511532 | A | 3/2009 |
| JP | 2009-84514 | A | 4/2009 |
| WO | WO 2006/001299 | A1 | 1/2006 |
| WO | WO 2007/071717 | A2 | 6/2007 |

OTHER PUBLICATIONS

Brigas et al., "Metal-assisted reactions. Part 29. Structure and hydrogenolysis of C-N bonds in derivatives of aromatic amines. Bond length and electronegativity changes from X-ray crystallographic data", Journal of the Chemical Society, Perkin Transactions 2, No. 8, 2001, pp. 1315-1324.

Chao et al., "Electroactive polyimide with oligoaniline in the main chain via oxidative coupling polymerization", European Polymer Journal, No. 43(6), 2007, pp. 2641-2647.

(Continued)

Primary Examiner — Kriellion Sanders
(74) Attorney, Agent, or Firm — Birch, Stewart, Kolasch & Birch, LLP

(57) ABSTRACT

There are provided a novel diarylamine compound represented by the following formula (I), (II) or (III), which has at least one signal attributable to the hydrogen of the N—H moiety at 8.30 ppm to 9.00 ppm when a deuterated dimethyl sulfoxide solution of the diarylamine compound is analyzed by $^1$H-NMR; and an aging inhibitor, a polymer composition, a crosslinked rubber product and a molded article thereof, and a method of producing a diarylamine compound. In the formulas, $A_1$ to $A_6$ each represent an aromatic group which may have a substituent; A represents an aromatic group or a cyclic aliphatic group, which may both have a substituent; L represents 1 or 2; and n represents 0 or 1.

10 Claims, No Drawings

(56) References Cited

OTHER PUBLICATIONS

Contino-Pepin et al., "Preliminary biological evaluations of new thalidomide analogues for multiple sclerosis application", Bioorganic & Medicinal Chemistry Letters 19, 2009, pp. 878-881.

International Search Report, dated Aug. 24, 2010 in PCT/JP2010/061199.

Magomedova et al., Crystallographic characteristics, optical and photoelectric properties of some phthalimide derivatives, Zhurnal Fizicheskoi Khimii, No. 50(8), 1976, pp. 2003-2006.

Oksent'Evich et al., Study of the mechanism of thermal degradation of compounds modeling aromatic polyimides, Vysokomolekulyarnye Soedineniya, Seriya A, No. 19(3), 1977, pp. 553-559.

Pebalk et al., Electron-acceptor properties of N-arylphtalimides, Doklady Akademii Nauk SSSR, No. 266(5), 1982, pp. 1170-1174.

Wang et al., Redox polyimides based on aniline trimer, Polymer Preprints (American Chemical Society, Division of Polymer Chemistry), No. 39(1), 1998, pp. 119-120.

Extended European Search Report dated Nov. 30, 2012, for European Application No. 10794206.2.

* cited by examiner

DIARYLAMINE COMPOUNDS, AGING INHIBITOR, POLYMER COMPOSITION, CROSSLINKED RUBBER PRODUCT AND MOLDED ARTICLE OF THE CROSSLINKED PRODUCT, AND METHOD OF PRODUCING DIARYLAMINE COMPOUND

TECHNICAL FIELD

The present invention relates to novel diarylamine compounds which can be used as an aging inhibitor having excellent effects even for rubber materials and the like that are required to have high heat resistance, an aging inhibitor, a polymer composition, a crosslinked rubber product and a molded article of the crosslinked product, and a method of producing a diarylamine compound.

BACKGROUND ART

Polymers such as rubbers and resins in their original state are susceptible to oxidative deterioration by means of heat or the like. Therefore, in order to enhance their heat resistance, various aging inhibitors are added thereto, and thus heat resistance is obtained for purposes. Well-known aging inhibitors include phenol-based aging inhibitors and amine-based aging inhibitors, and a representative class of the amine-based aging inhibitors is diphenylamine-based aging inhibitors, which are diarylamine compounds.

As the diphenylamine-based aging inhibitors which are diarylamine compounds, compounds such as shown below are described in Japanese Patent Application Laid-Open (JP-A) No. 9-53070 (Patent Literature 1), JP-A No. 10-298551 (Patent Literature 2), JP-A No. 11-21411 (Patent Literature 3) and the like, and those compounds are used for general use.

[Chemical Formula 1]

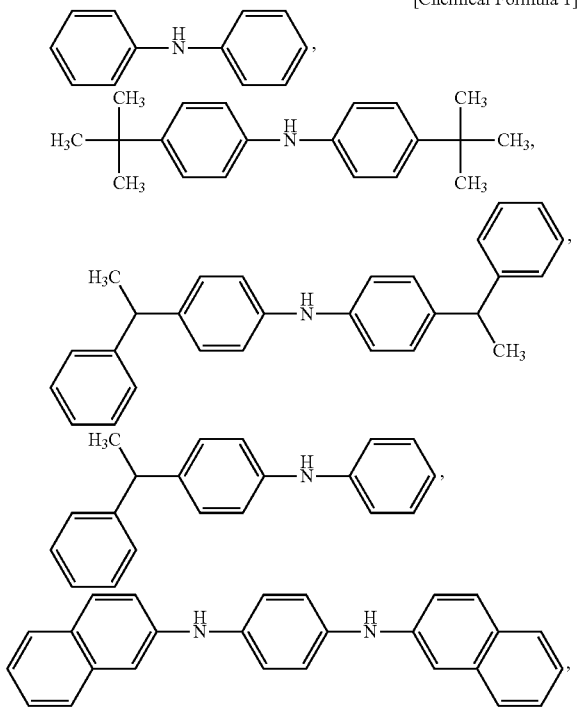

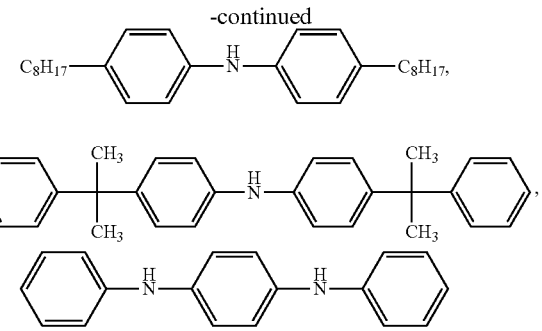

In recent years, polymeric materials such as rubbers are increasingly used in high temperature conditions which are severer than in the past. To take an example of a rubber used in the periphery of an engine of an automobile, there is a tendency that the temperature inside the engine room increases due to the increased power output of automobile engines, or the emergence of low pollution engines. Thus, rubber materials that are used in the periphery of such an engine are required to have a heat resistance property higher than conventional rubber materials, and therefore, there is a strong demand for a rubber material which can endure in that environment. As one of the means to achieve the purpose, there is a strong demand for a diphenylamine-based compound having a new structure, which does not cause oxidative deterioration of polymers such as rubbers and resins even if used in a higher temperature environment than in conventional cases, and is appropriate for aging inhibitors having high heat resistant effect. However, sufficient effects could not be obtained with diphenylamine-based aging inhibitors that are conventionally known.

Among rubber materials, an acrylic rubber is known as a rubber having excellent oil resistance, particularly oil resistance at high temperatures, and having satisfactory heat resistance, and there is an increasing demand for an acrylic rubber for hoses, oil seals, gaskets, O-rings in automobile-related fields, and for conveyor belts mounted in apparatuses and machines. For the rubber members for use in automobiles, particularly the rubber members in the engine rooms, performance enhancement of superchargers (turbochargers) along with an increase in the output power of engines, and the recent tightened regulations on exhaust gas have caused a further demand for an enhancement of the heat resistant performance.

For example, it is disclosed in JP-A No. 11-21411 (Patent Literature 3) described above that when an acrylic rubber and two kinds of diphenylamine-based oxidation inhibitor are used in combination, the heat resistance of a crosslinked acrylic rubber product is enhanced. However, when this technology is employed, improvements in the tensile force change rate, the elongation change rate, and the compression set in a short-term heat resistance test are recognized, but the effect in a long-term heat resistance test of the crosslinked acrylic rubber product at high temperatures is not recognized.

Furthermore, in recent years, it has been suggested to use various aging inhibitors instead of 4,4'-bis(α,α'-dimethylbenzyl)diphenylamine or the like, in order to enhance the heat resistance of crosslinked acrylic rubber products. For example, it is disclosed in WO 2006/001299 (Patent Literature 4) that the heat resistance of a crosslinked acrylic rubber product is enhanced by incorporating a styrenated diphenylamine compound into a carboxyl group-containing acrylic rubber. However, when this technology is employed, an improvement in the tensile strength change rate is acknowledged compared to the case of incorporating 4,4'-bis(α,α'-dimethylbenzyl)diphenylamine; however, improvements in the elongation change rate, the compression set, and the effect in a long-term heat resistance test of the crosslinked acrylic rubber product at high temperatures are insufficient.

PRIOR ART DOCUMENTS

Patent Literatures

Patent Literature 1: JP-A No. 9-53070
Patent Literature 2: JP-A No. 10-298551
Patent Literature 3: JP-A No. 11-21411
Patent Literature 4: WO 2006/001299

SUMMARY OF THE INVENTION

Problem to be Solved by the Invention

An object of the present invention is to provide diarylamine compounds having new structures, which do not cause oxidative deterioration of polymers such as rubbers and resins even if used in a higher temperature environment than in conventional cases, and are appropriate for aging inhibitors having high heat resistant effect. Another object of the present invention is to provide an aging inhibitor, particularly an aging inhibitor for polymers, which contains one of the compounds. Another object of the present invention is to provide a polymer composition, particularly a rubber composition, more particularly an acrylic rubber composition, which contains one of the compounds and a polymer and has high heat resistance. Furthermore, another object of the present invention is to provide a crosslinked rubber product formed by crosslinking the rubber composition, and a molded article formed from the crosslinked rubber product. Another object of the present invention is to provide a method of producing a diarylamine compound.

Means for Solving the Problem

The inventors of the present invention conducted a thorough investigation in order to achieve the objects described above, and as a result, the inventors found that a diarylamine compound having a novel structure, which does not easily cause aging deterioration of polymers such as rubbers and resins even if used in a higher temperature environment than in conventional cases, is capable of imparting highly excellent thermal stability, and is appropriate for aging inhibitors. Furthermore, the inventors succeeded in obtaining an aging inhibitor containing this novel compound, particularly an aging inhibitor for polymers, and a polymer composition, particularly a rubber composition, more particularly an acrylic rubber composition, which has high heat resistance. In addition, the inventors of the present invention succeeded in providing a crosslinked rubber product which is formed by crosslinking the rubber composition, and a molded article formed from the crosslinked rubber product, and thus found a method of efficiently producing a diarylamine compound.

That is, according to the present invention, there is provided, as a novel diarylamine compound, a diarylamine compound represented by any one of the following formulas (I), (II) or (III), which has at least one signal attributable to the hydrogen of the N—H moiety at 8.30 ppm to 9.00 ppm when a deuterated dimethyl sulfoxide solution of the diarylamine compound is analyzed by $^1$H-NMR:

Formula (I)

[Chemical Formula 2]

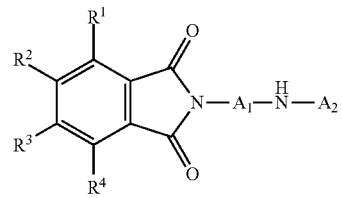

wherein in the formula (I), $A_1$ and $A_2$ each independently represent an aromatic group which may have a substituent having 1 to 30 carbon atoms;

$R^1$, $R^3$ and $R^4$ each independently represent a hydrogen atom, a halogen atom, an alkyl group having 1 to 10 carbon atoms which may have a substituent, a cyano group, a nitro group, —OR, —O—C(=O)—R, —C(=O)—OR, —O—C(=O)—OR, —NR'—C(=O)—R, —C(=O)—NRR°, or —O—C(=O)—NRR°;

R and R° each independently represent a hydrogen atom, or an organic group having 1 to 30 carbon atoms which may have a substituent;

R's each independently represent a hydrogen atom, or an alkyl group having 1 to 6 carbon atoms;

the relevant organic group may be an organic group which is interrupted by at least one linking group selected from the group consisting of —O—, —S—, —O—C(=O)—, —C(=O)—O—, —O—C(=O)—O—, —NR"—C(=O)—, —C(=O)—NR"—, —NR"— and —C(=O)—, but organic groups which are interrupted by two or more contiguous —O— or —S— moieties are excluded;

R"s each independently represent a hydrogen atom, or an alkyl group having 1 to 6 carbon atoms;

$R^2$ represents a hydrogen atom, a halogen atom, an alkyl group having 1 to 10 carbon atoms which may have a substituent, a cyano group, a nitro group, —O—C(=O)—R'", —C(=O)—OR'", —NR'—C(=O)—R'", —C(=O)—NR'"R"" or —O—C(=O)—NR'"R"";

R'"s and R""s each independently represent an organic group having 1 to 30 carbon atoms which may have a substituent;

the relevant organic group may be an organic group which is interrupted by at least one linking group selected from the group consisting of —O—, —S—, —O—C(=O)—, —C(=O)—O—, —NR"—C(=O)—, —C(=O)—NR"—, —NR"— and —C(=O)—, but organic groups which are interrupted by two or more contiguous —O— or —S— moieties are excluded; and R's and R"s each independently represent a hydrogen atom, or an alkyl group having 1 to 6 carbon atoms;

Formula (II)

[Chemical Formula 3]

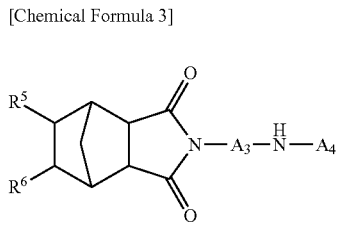
(II)

wherein in the formula (II), $A_3$ and $A_4$ each independently represent an aromatic group which may have a substituent having 1 to 30 carbon atoms;

$R^5$ and $R^6$ each independently represent a hydrogen atom, a halogen atom, an alkyl group having 1 to 10 carbon atoms which may have a substituent, a cyano group, a nitro group, —OR, —O—C(=O)—R, —C(=O)—OR, —O—C(=O)—OR, —NR'—C(=O)—R, —C(=O)—NRR° or —O—C(=O)—NRR°;

R and R° each independently represent a hydrogen atom, or an organic group having 1 to 30 carbon atoms which may have a substituent;

the relevant organic group may be interrupted by at least one linking group selected from the group consisting of —O—, —S—, —O—C(=O)—, —C(=O)—O—, —O—C(=O)—O—, —NR"—C(=O)—, —C(=O)—NR"—, —NR"— and —C(=O)—, but organic groups which are interrupted by two or more contiguous —O— or —S— moieties are excluded; and R's and R"s each independently represent a hydrogen atom, or an alkyl group having 1 to 6 carbon atoms; or Formula (III)

[Chemical Formula 4]

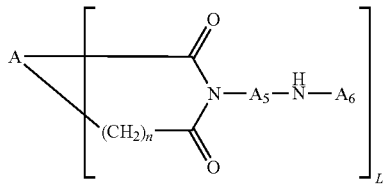
(III)

wherein in the formula (III),

A represents an aromatic group having 6 to 30 carbon atoms which may have a substituent, or a cyclic aliphatic group having 4 to 30 carbon atoms which may have a substituent;

L represents 1 or 2, and n represents 0 or 1;

the following formula (iii-1) represents the following formula (iii-2):

Formula (iii-1)

[Chemical Formula 5]

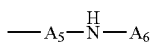
(iii-1)

Formula (iii-2)

[Chemical Formula 6]

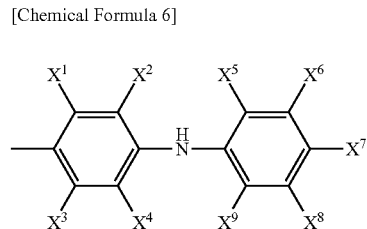
(iii-2)

$X^1$ to $X^9$ each independently represent a hydrogen atom, a halogen atom, an alkyl group having 1 to 10 carbon atoms which may have a substituent, a cyano group, a nitro group, —OR, —O—C(=O)—R, —C(=O)—OR, —O—C(=O)—OR, —NR'—C(=O)—R, —C(=O)—NRR° or —O—C(=O)—NRR°;

R and R° each independently represent a hydrogen atom, or an organic group having 1 to 30 carbon atoms which may have a substituent;

the relevant organic group may be an organic group which is interrupted by at least one linking group selected from the group consisting of —O—, —S—, —O—C(=O)—, —C(=O)—O—, —O—C(=O)—O—, —NR"—C(=O)—, —C(=O)—NR"—, —NR"— and —C(=O)—, but organic groups which are interrupted by two or more contiguous —O— or —S— moieties are excluded; and R's and R"s each independently represent a hydrogen atom, or an alkyl group having 1 to 6 carbon atoms.

Furthermore, according to the present invention, the following embodiments are provided as novel diarylamine compounds having at least one signal attributable to the hydrogen of the N—H moiety at 8.30 ppm to 9.00 ppm when a deuterated dimethyl sulfoxide solution of the diarylamine compound is analyzed by $^1$H-NMR.

(1) A diarylamine compound represented by the formula (I), in which $A_1$ represents a phenylene group which may have a substituent having 1 to 30 carbon atoms;

$A_2$ represents a phenyl group which may have a substituent having 1 to 30 carbon atoms;

$R^1$, $R^3$ and $R^4$ represent hydrogen atoms;

$R^2$ represents —O—C(=O)—R''', —C(=O)—OR''', —NR'—C(=O)—R''', —C(=O)—NR'''R'''' or —O—C(=O)—NR'''R'''';

R' represents a hydrogen atom, or an alkyl group having 1 to 6 carbon atoms; and R'''s and R''''s each independently represent an organic group having 1 to 30 carbon atoms which may have a substituent.

(2) A diarylamine compound represented by the formula (I), in which:

$R^2$ represents —C(=O)—OR'''; and

R''' represents a phenyl group which may have a substituent having 1 to 18 carbon atoms, or a naphthyl group which may have a substituent having 1 to 18 carbon atoms.

(3) A diarylamine compound represented by the formula (I), in which:

$R^2$ represents —C(=O)—OR''', R''' represents an alkyl group having 1 to 10 carbon atoms which may have a substituent, or an aromatic group having 4 to 30 carbon atoms which may have a substituent;

the relevant substituents are each independently a halogen atom, an alkyl group having 1 to 10 carbon atoms, an aralkyl group having 1 to 20 carbon atoms, an aromatic group having 6 to 30 carbon atoms, a cyano group, a nitro group, a sulfo group, —OR$^a$, —C(=O)—OR$^a$, —O—C(=O)—OR$^a$, —NR$^c$—C(=O)—R$^a$, —C(=O)—NR$^a$R$^b$, —O—C(=O)—NR$^a$R$^b$, —SR$^a$, —S(=O)—R$^a$, or —S(=O)$_2$—R$^a$;

R$^a$, R$^b$ and R$^c$ each independently represent a hydrogen atom, an alkyl group having 1 to 8 carbon atoms, or a phenyl group;

meanwhile, A$_1$ and A$_2$ each independently represent an aromatic group having 6 to 30 carbon atoms which may have a substituent; and the relevant substituent is an alkyl group having 1 to 10 carbon atoms, a halogen-substituted alkyl group having 1 to 10 carbon atoms, a halogen atom, a cyano group or a nitrile group.

(4) A diarylamine compound represented by the formula (II), in which:

A$_3$ represents a phenylene group which may have a substituent having 1 to 30 carbon atoms;

A$_4$ represents a phenyl group which may have a substituent having 1 to 30 carbon atoms;

R$^5$ and R$^6$ each independently represent a hydrogen atom, —O—C(=O)—R, —C(=O)—OR, —NR'—C(=O)—R, —C(=O)—NRR$^0$ or —O—C(=O)—NRR$^0$;

R and R$^0$ each independently represent an organic having 1 to 30 carbon atoms which may have a substituent;

the relevant organic group may be an organic group which is interrupted by at least one linking group selected from the group consisting of —O—, —S—, —O—C(=O)—, —C(=O)—O—, —O—C(=O)—O—, —NR''—C(=O)—, —C(=O)—NR''—, —NR''— or —C(=O)—, but organic groups which are interrupted by two or more contiguous —O— or —S— moieties are excluded; and R's and R''s each independently represent a hydrogen atom, or an alkyl group having 1 to 6 carbon atoms.

(5) A diarylamine compound represented by the formula (II), in which R$^5$ and R$^6$ represent hydrogen atoms.

(6) A diarylamine compound represented by the formula (III), in which A represents one selected from the group consisting of a phenyl group which may have a substituent, a 5-membered ring cyclic aliphatic group which may have a substituent, a 6-membered ring cyclic aliphatic group which may have a substituent, and a bicyclo[2.2.1]heptyl group which may have a substituent.

According to the present invention, there is provided an aging inhibitor, particularly an aging inhibitor for polymers, containing any one of these diarylamine compounds.

According to the present invention, there is provided a polymer composition containing any one of these compounds and a polymer. According to the present invention, there is provided a polymer composition in which the polymer is a rubber, that is, a rubber composition. According to the present invention, there is provided a rubber composition in which the rubber is an acrylic rubber or a hydrogenated nitrile rubber, and there is provided a rubber composition containing an acrylic rubber and a crosslinking agent, particularly a rubber composition containing 100 parts by weight of an acrylic rubber, 0.1 to 50 parts by weight of a compound represented by one of the formulas (I) to (III), and 0.05 to 20 parts by weight of a crosslinking agent. According to the present invention, there is provided a crosslinked rubber product formed by crosslinking the rubber composition, and particularly, there is provided a crosslinked rubber product which is an extrusion molded article or a sealing member.

Furthermore, according to the present invention, there is provided, as a method of producing a novel diarylamine compound, a method of producing a novel diarylamine compound represented by the following formula (VII):

[Chemical Formula 13]

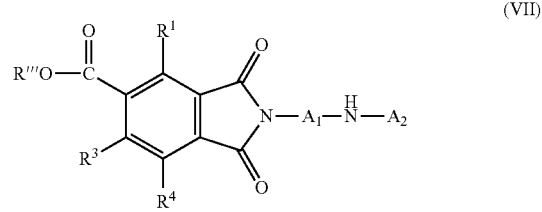

(VII)

the method including three processes, such as Process 1 of allowing a trimellitic anhydride halide compound represented by the following formula (IV):

[Chemical Formula 7]

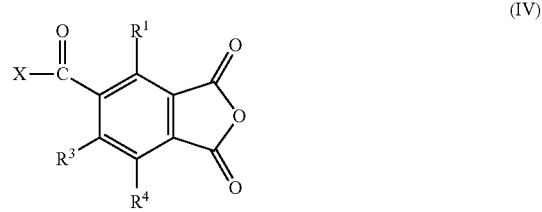

(IV)

wherein in the formula (IV),

R$^1$, R$^3$ and R$^4$ each independently represent a hydrogen atom, a halogen atom, an alkyl group having 1 to 10 carbon atoms which may have a substituent, a cyano group, a nitro group, —OR, —O—C(=O)—R, —C(=O)—OR, —O—C(=O)—OR, —NR'—C(=O)—R, —C(=O)—NRR$^0$ or —O—C(=O)—NRR$^0$;

R and R$^0$ each independently represent a hydrogen atom, or an organic group having 1 to 30 carbon atoms which may have a substituent;

the relevant organic group may be an organic group which is interrupted by at least one linking group selected from the group consisting of —O—, —S—, —O—C(=O)—, —C(=O)—O—, —O—C(=O)—O—, —NR''—C(=O)—, —C(=O)—NR''—, —NR''— and —C(=O)—, but organic groups which are interrupted by two or more contiguous —O— or —S— moieties are excluded;

R' and R'' each independently represent a hydrogen atom, or an alkyl group having 1 to 6 carbon atoms;

the relevant substituent includes a halogen atom, a cyano group, or a nitro group; and X represents a halogen atom, to react with a hydroxyl group-containing compound represented by the following formula (V):

[Chemical Formula 8]

R'''OH (V)

wherein in the formula (V),

R''' represents an alkyl group having 1 to 10 carbon atoms which may have a substituent, or an aromatic group having 4 to 30 carbon atoms which may have a substituent;

the relevant substituents are each independently a halogen atom, an alkyl group having 1 to 10 carbon atoms, an aralkyl group having 1 to 20 carbon atoms, an aromatic group having 6 to 30 carbon atoms, a cyano group, a nitro group, a sulfo group, $-OR^a$, $-O-C(=O)-R^a$, $-C(=O)-OR^a$, $-O-C(=O)-OR^a$, $-NR^c-C(=O)-R^a$, $-C(=O)-NR^aR^b$, $-O-C(=O)-NR^aR^b$, $-SR^a$, $-S(=O)-R^a$ or $-S(=O)_2-R^a$; and $R^a$, $R^b$ and $R^c$ each independently represent a hydrogen atom, an alkyl group having 1 to 8 carbon atoms, or a phenyl group, in an organic solvent in the presence of a base, and thereby producing a trimellitic anhydride ester compound by the following reaction scheme (1):

[Chemical Formula 9]

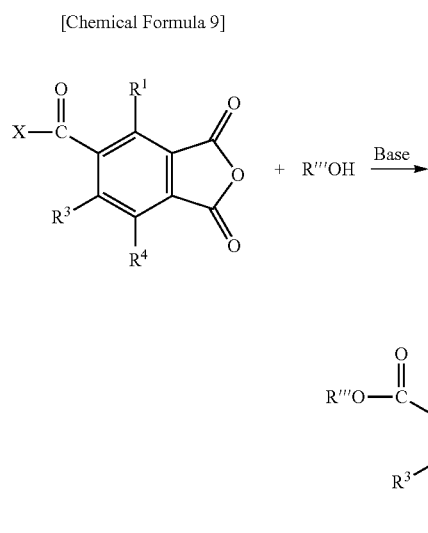

(1)

wherein the symbols used in the reaction scheme (1) respectively have the same meanings as defined above;

Process 2 of allowing the trimellitic anhydride ester compound produced in Process 1 to react with an amino group-containing diarylamine compound represented by the following formula (VI):

[Chemical Formula 10]

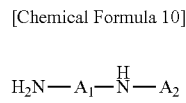

(VI)

wherein in the formula (VI), $A_1$ and $A_2$ each independently represent an aromatic group having 6 to 30 carbon atoms which may have a substituent; and the relevant substituents are each independently an alkyl group having 1 to 10 carbon atoms, a halogen-substituted alkyl group having 1 to 10 carbon atoms, a halogen atom, a cyano group, or a nitro group, in an organic solvent, and thereby producing an amide acid compound by the following reaction scheme (2):

[Chemical Formula 11]

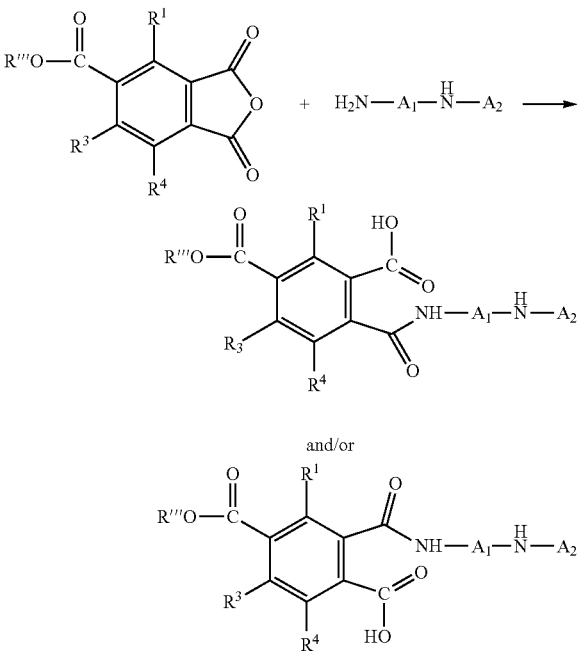

(2)

wherein the symbols used in the reaction scheme (2) respectively have the same meanings as defined above; and Process 3 of heating the reaction solution containing the amide acid compound produced in Process 2, and thereby imidating the amide acid compound by the following reaction scheme (3):

[Chemical Formula 12]

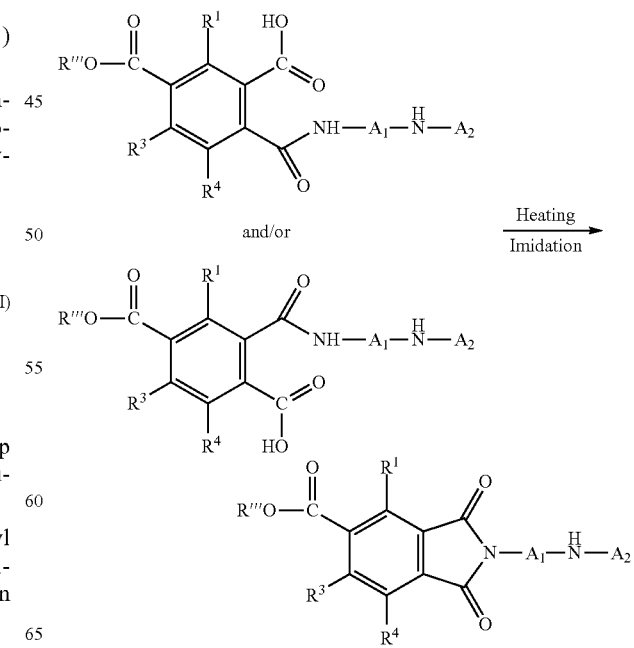

(3)

wherein the symbols used in the reaction scheme (3) respectively have the same meanings as defined above, wherein these three processes are carried out in a one-pot process in the presence of an organic solvent.

Furthermore, according to the present invention, the following embodiments are provided as the method of producing a diarylamine compound.

(1) The method of producing a diarylamine compound as described above, wherein the amino group-containing diarylamine compound is an aminodiphenylamine compound represented by the following formula (VIII):

[Chemical Formula 14]

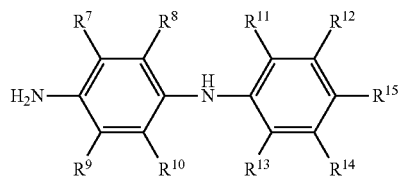

(VIII)

the method includes three processes represented by the following reaction scheme (1a):

[Chemical Formula 15]

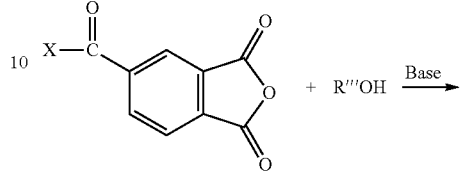

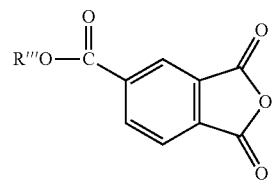

(1a)

wherein in the reaction scheme (1a), R''' has the same meaning as defined above, the following reaction scheme (2a):

[Chemical Formula 16]

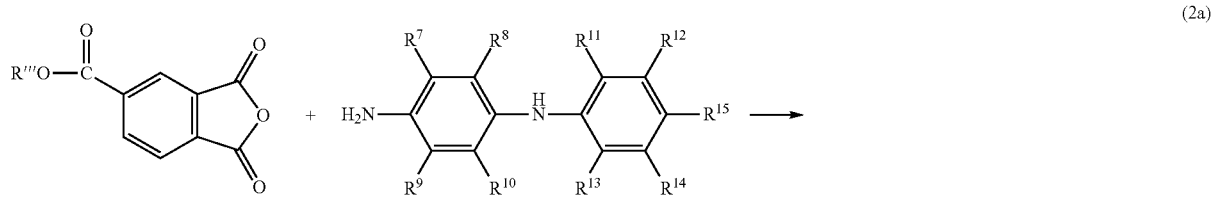

(2a)

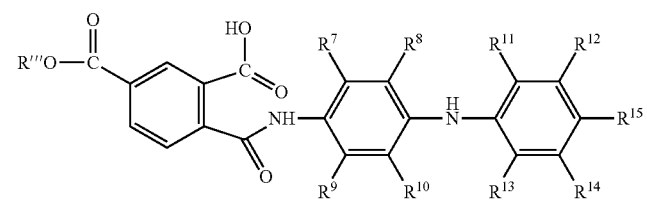

and/or

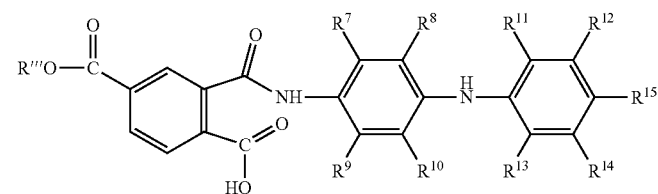

wherein in the formula (VIII),

R$^7$ to R$^{15}$ each independently represent a hydrogen atom, an alkyl group having 1 to 10 carbon atoms, a halogen-substituted alkyl group having 1 to 10 carbon atoms, a halogen atom, a cyano group, or a nitro group, and wherein in the reaction scheme (2a), R''' has the same meaning as defined above; and R$^7$ to R$^{15}$ respectively have the same meanings as defined above, and the following reaction scheme (3a):

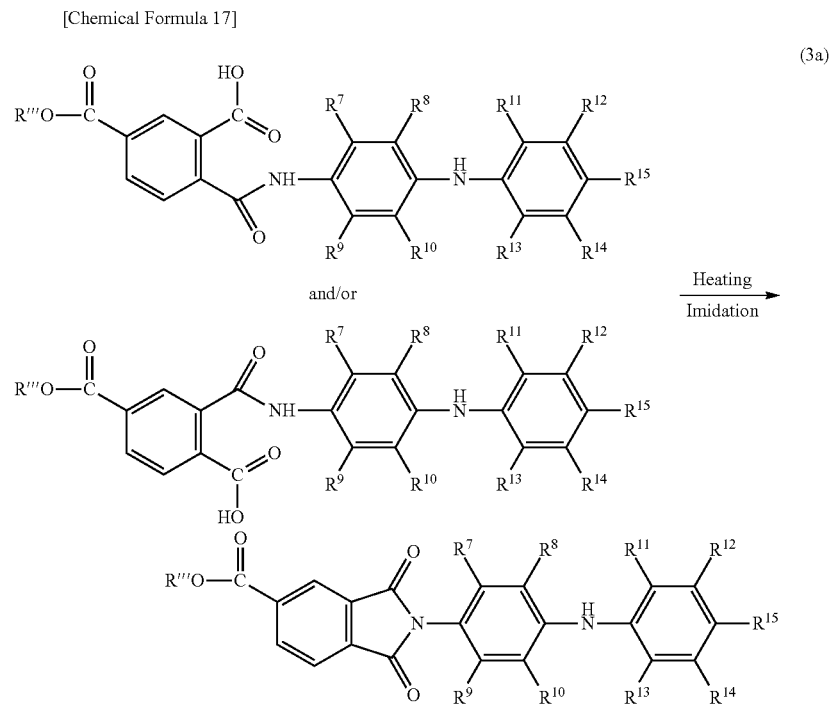

wherein the symbols used in the reaction scheme (3a) respectively have the same meanings as defined above, wherein these three processes are carried out in a one-pot process in the presence of an organic solvent, and thereby, a phthalimide group-containing diphenylamine compound having an ester group at the 4-position, represented by the following formula (IX), as a phthalimide group-containing diarylamine compound having an ester group at the 4-position:

[Chemical Formula 18]

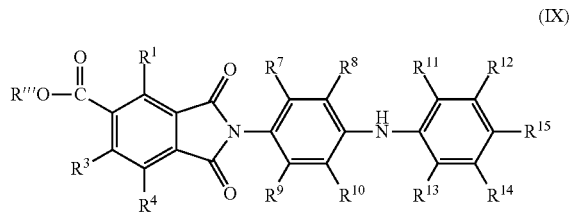

wherein the symbols used in the formula (IX) respectively have the same meanings as defined above, is produced.

(2) The method of producing a diarylamine compound as described above, wherein the trimellitic anhydride halide compound is trimellitic anhydride chloride, and the amino group-containing diarylamine compound is an aminodiphenylamine compound represented by the following formula (X):

[Chemical Formula 19]

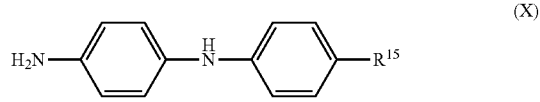

wherein in the formula (X), $R^{15}$ represents a hydrogen atom, an alkyl group having 1 to 10 carbon atoms, a halogen-substituted alkyl group having 1 to 10 carbon atoms, a halogen atom, a cyano group, or a nitro group, and wherein the method includes three processes represented by the following reaction scheme (1b):

[Chemical Formula 20]

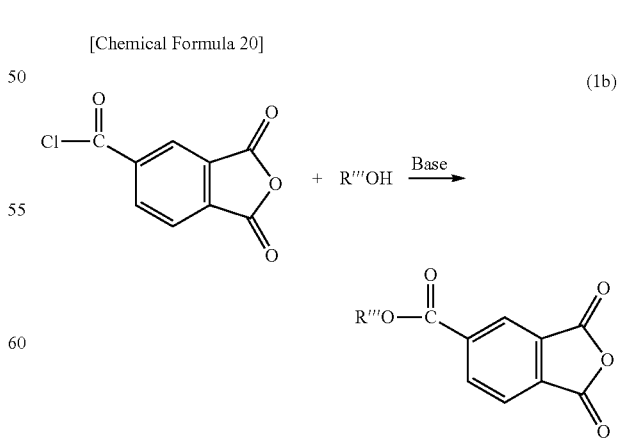

wherein in the reaction scheme (1b), R''' has the same meaning as defined above, the following reaction scheme (2b):

[Chemical Formula 21]

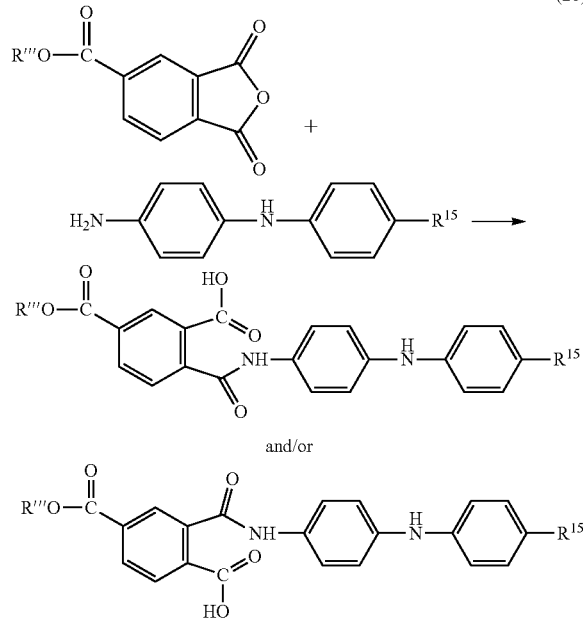

(2b)

and/or wherein the symbols used in the reaction scheme (2b) respectively have the same meanings as defined above, and the following reaction scheme (3b):

[Chemical Formula 22]

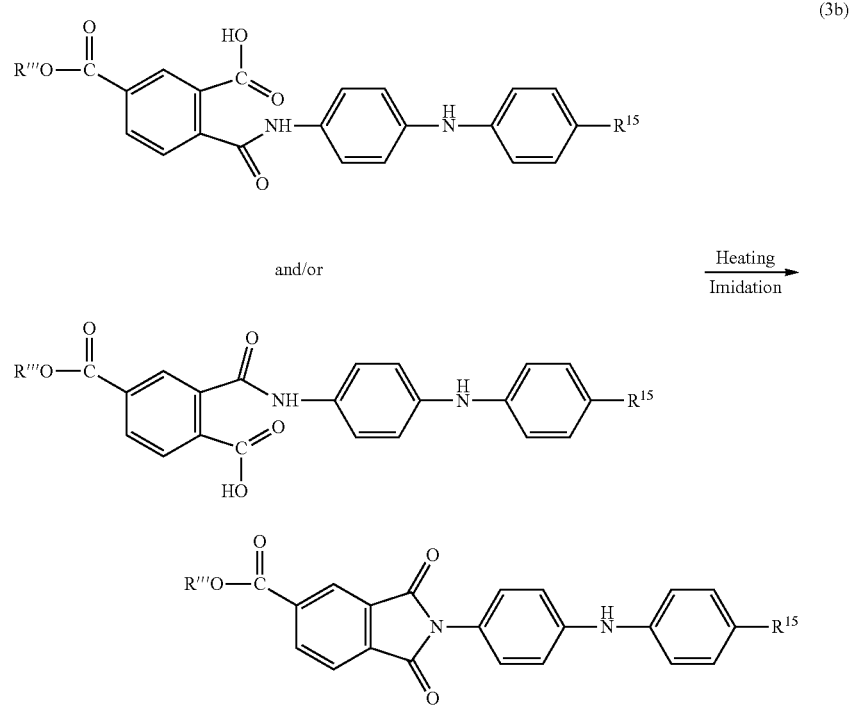

(3b)

wherein the symbols used in the reaction scheme (3b) respectively have the same meanings as defined above, and these three processes are carried out in a one-pot process in the presence of an organic solvent to thereby produce a phthalimide group-containing diphenylamine compound having an ester group at the 4-position, as represented by the following formula (XI), as a phthalimide group-containing diarylamine compound having an ester group at the 4-position:

[Chemical Formula 23]

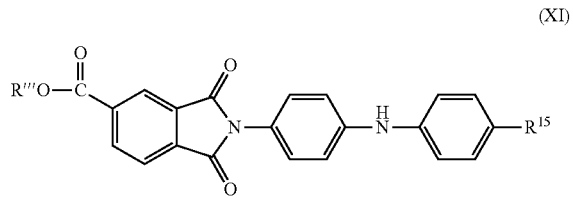

(XI)

wherein the symbols used in the formula (XI) respectively have the same meanings as defined above.

(3) The method of producing a diarylamine compound as described above, wherein the organic solvent is at least one organic solvent selected from the group consisting of an aprotic polar solvent and a non-polar solvent.

(4) The method of producing a diarylamine compound as described above, wherein the organic solvent is a solvent mixture of a nitrogen-containing aprotic polar solvent and an aromatic hydrocarbon-based non-polar solvent.

(5) The method of producing a diarylamine compound as described above, wherein the organic solvent is a solvent mixture of N,N-dimethylformamide and xylene.

In regard to the compounds represented by the formulas (I) to (III) of the present invention, since the signal attributable to the hydrogen of the N—H moiety in the diarylamine molecular skeleton appears at 8.14 ppm, the diarylamine compound of the present invention is a compound having a signal on the lower magnetic field side. It is speculated that for the N—H moiety in the diarylamine molecular skeleton, an imide ring-containing group bonded to the p-position acts as an electron-withdrawing group, and as a result, the electron density of the hydrogen atom of the N—H moiety is decreased. Conventionally, it has been considered that a diphenylamine having an electron-donating group and the like increases the efficacy as a stabilizer. Therefore, the present invention is based on a novel idea that defies this common belief, and the inventors have newly found that decreasing the electron density of the hydrogen atom of the N—H moiety provides an effect of enhancing heat resistance when the diarylamine compounds are used as aging inhibitors for polymers and the like. Thus, the inventors have conceived the new compounds.

The compounds of the present invention have at least one signal attributable to the hydrogen of the N—H moiety at 8.30 ppm to 9.00 ppm when a deuterated dimethyl sulfoxide (DMSO-d6) solution of one of the compounds is analyzed by $^1$H-NMR. However, a compound having the signal preferably at 8.31 ppm to 8.97 ppm, and more preferably at 8.37 ppm to 8.95 ppm, is used, heat resistance and rubber elasticity can be improved in a well-balanced manner.

Furthermore, when the diphenylamine-based compounds of the present invention have plural N—H moieties in the molecule, it is preferable that the signal attributable to the hydrogen of at least one of the N—H moieties appears at 8.30 ppm to 9.00 ppm.

Effect of the Invention

According to the present invention, there are provided diarylamine compounds having novel structures, which do not cause oxidative deterioration or the like of polymers such as rubbers or resins even if used in a higher temperature environment than in conventional cases, and can be used for aging inhibitors. Furthermore, according to the present invention, there is provided an aging inhibitor, particularly an aging inhibitor for polymers, which contain one of the diarylamine compounds. Furthermore, there is provided a polymer composition having high heat resistance, which contains one of the compounds and a polymer, particularly a rubber composition, more particularly an acrylic rubber composition, which can suppress a decrease in the properties such as elongation and compression set even if exposed to high temperature conditions for long hours. According to the present invention, there are provided a crosslinked rubber product having high heat resistance, which is formed by crosslinking the rubber composition, and a molded article, particularly an extrusion molded article, and a sealing member, which are formed from the crosslinked rubber product. According to the present invention, diarylamine compounds can be efficiently produced.

BEST MODE(S) FOR CARRYING OUT THE INVENTION

The diarylamine compound having a novel structure that can be used in the aging inhibitor of the present invention is a diarylamine compound represented by one of the above-described formulas (I), (II) and (III), which has at least one signal attributable to the hydrogen of the N—H moiety at 8.30 ppm to 9.00 ppm when a deuterated dimethyl sulfoxide solution of the diarylamine compound is analyzed by $^1$H-NMR. The diarylamine compound may be a diarylamine compound represented by one of the formulas (I), (II) and (III), or may be a diarylamine compound represented by two of the formulas (I), (II) and (III). For example, the diarylamine compound may be a diarylamine compound represented by both the formula (I) and the formula (III), or may be a diarylamine compound represented by both the formula (II) and the formula (III).

1. Diarylamine Compound Represented by Formula (I)

The diarylamine compound represented by formula (I), which has at least one signal attributable to the hydrogen of the N—H moiety at 8.30 ppm to 9.00 ppm when the deuterated dimethyl sulfoxide solution of the present invention is analyzed by is a diarylamine compound represented by the formula:

[Chemical Formula 24]

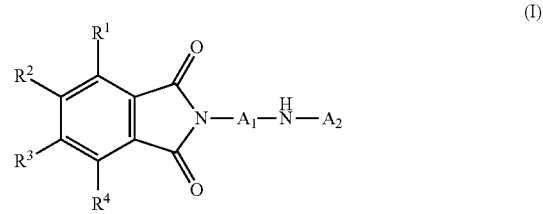

(I)

wherein in the formula (I), $A_1$ and $A_2$ each independently represent an aromatic group which may have a substituent having 1 to 30 carbon atoms;

$R^1$, $R^3$ and $R^4$ each independently represent a hydrogen atom, a halogen atom, an alkyl group having 1 to 10 carbon atoms which may have a substituent, a cyano group, a nitro group, —OR, —O—C(=O)—R, —C(=O)—OR, —O—C(=O)—OR, —NR'—C(=O)—R, —C(=O)—NRR°, or —O—C(=O)—NRR°;

R and R° each independently represent a hydrogen atom, or an organic group having 1 to 30 carbon atoms which may have a substituent;

R's each independently represent a hydrogen atom, or an alkyl group having 1 to 6 carbon atoms;

the relevant organic group may be an organic group which is interrupted by at least one linking group selected from the group consisting of —O—, —S—, —O—C(=O)—, —C(=O)—O—, —NR"—C(=O)—, —C(=O)—NR"—, —NR"— and —C(=O)—, but organic groups which are interrupted by two or more contiguous —O— or —S— moieties are excluded;

R"s each independently represent a hydrogen atom, or an alkyl group having 1 to 6 carbon atoms;

$R^2$ represents a hydrogen atom, a halogen atom, an alkyl group having 1 to 10 carbon atoms which may have a substituent, a cyano group, a nitro group, —O—C(=O)—R''', —C(=O)—OR''', —NR'—C(=O)—R''', —C(=O)—NR'''R'''' or —O—C(=O)—NR'''R'''';

R'''s and R''''s each independently represent an organic group having 1 to 30 carbon atoms which may have a substituent;

the relevant organic group may be an organic group which is interrupted by at least one linking group selected from the group consisting of —O—, —S—, —O—C(=O)—, —C(=O)—O—, —NR"—C(=O)—, —C(=O)—NR"—, —NR"— and —C(=O)—, but organic groups which are interrupted by two or more contiguous —O— or —S— moieties are excluded; and R's and R"s each independently represent a hydrogen atom, or an alkyl group having 1 to 6 carbon atoms.

In the formula (I), it is preferable to select a compound represented by the formula in which, preferably, $A_1$ represents a phenylene group which may have a substituent having 1 to 30 carbon atoms;

$A_2$ represents a phenyl group which may have a substituent having 1 to 30 carbon atoms;

$R^1$, $R^3$ and $R^4$ represent hydrogen atoms;

$R^2$ represents —O—C(=O)—R'", —C(=O)—OR'", —NR'—C(=O)—R'", —C(=O)—NR'"R"", or —O—C(=O)—NR'"R"";

R' represents a hydrogen atom, or an alkyl group having 1 to 6 carbon atoms; and R'" and R"" each independently represent an organic group having 1 to 30 carbon atoms which may have a substituent.

Among these, more preferably, a diarylamine compound represented by the formula (I), in which:

$R^2$ is —C(=O)—OR'"; and

R'" is a phenyl group which may have a substituent having 1 to 18 carbon atoms, or a naphthyl group which may have a substituent having 1 to 18 carbon atoms, can be selected.

Even more preferably, a diarylamine compound represented by the formula (I), in which:

$R^2$ is —C(=O)—OR'", and R'" represents an alkyl group having 1 to 10 carbon atoms which may have a substituent, or an aromatic group having 4 to 30 carbon atoms which may have a substituent;

the relevant substituents each independently represent a halogen atom, an alkyl group having 1 to 10 carbon atoms, an aralkyl group having 1 to 20 carbon atoms, an aromatic group having 6 to 30 carbon atoms, a cyano group, a nitro group, a sulfo group, —$OR^a$, —O—C(=O)—$R^a$, —C(=O)—$OR^a$, —O—C(=O)—$OR^a$, —$NR^c$—C(=O)—$R^a$, —C(=O)—$NR^aR^b$, —O—C(=O)—$NR^aR^b$, —$SR^a$, —S(=O)—$R^a$, or —$S(=O)_2$—$R^a$;

$R^a$, $R^b$ and $R^c$ each independently represent a hydrogen atom, an alkyl group having 1 to 8 carbon atoms, or a phenyl group;

on the other hand, $A_1$ and $A_2$ each independently represent an aromatic group having 6 to 30 carbon atoms which may have a substituent; and the relevant substituent is an alkyl group having 1 to 10 carbon atoms, a halogen-substituted alkyl group having 1 to 10 carbon atoms, a halogen atom, a cyano group, or a nitro group, that is, a phthalimide group-containing diarylamine compound having an ester group at the 4-position of the following formula can be selected:

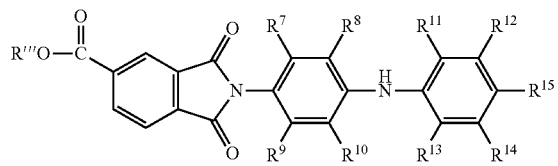

[Chemical Formula 25]

Furthermore, the diarylamine compound represented by the formula (I) will specifically be described.

It is preferable that $R^2$ be an ester group represented by the formula: —C(=O)—OR'", from the viewpoint that the production of the compound is easy. Here, R'" is an organic group having 1 to 30 carbon atoms which may have a substituent, and the relevant organic group can be selected from many aliphatic groups or aromatic groups, such as an alkyl group, a cycloalkyl group, an aryl group, an arylalkyl group, an alkylaryl group, an arylalkylaryl group, and an alkoxy group. However, from the viewpoint of heat resistance, it is preferable to select an aromatic group, particularly a phenyl group or a naphthyl group.

Particularly, if $R^2$ is —C(=O)—OR'", and R'" is an aromatic group having 1 to 20 carbon atoms which may have a substituent, when the diarylamine compound is used as an aging inhibitor, a superior effect of enhancing heat resistance is obtained. The fact that if the compound has an ester structure in which $R^2$ is —C(=O)—OR'", and R'" is a phenyl group which may have a substituent having 1 to 18 carbon atoms or a naphthyl group which may have a substituent having 1 to 18 carbon atoms, the diarylamine compound provides a particularly excellent effect of enhancing heat resistance, cannot ever be predicted by those having ordinary skill in the art.

There are no particular limitations on the diarylamine compound having a novel structure that can be used in the aging inhibitor of the present invention, as long as the diarylamine compound has at least one signal attributable to the hydrogen of the N—H moiety at 8.30 ppm to 9.00 ppm when a deuterated dimethyl sulfoxide solution of the diarylamine compound is analyzed by $^1$H-NMR, and the diarylamine compound satisfies the formula (I). However, from the viewpoint of providing an excellent effect of enhancing heat resistance, particularly preferred examples of the compound include the following compounds.

Compound 1

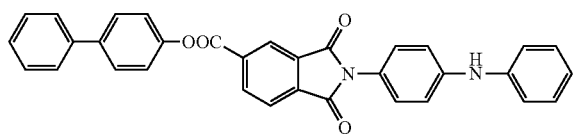

[Chemical Formula 26]

Compound 2
[Chemical Formula 27]
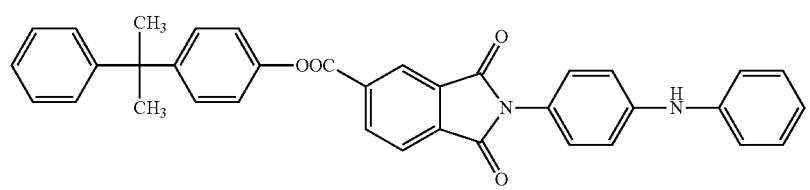
Compound 3
[Chemical Formula 28]
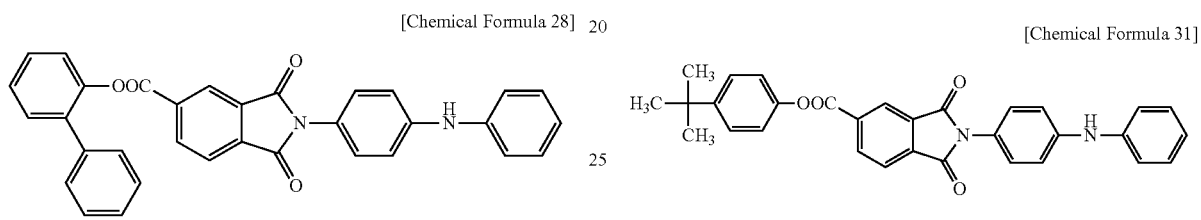
Compound 4
[Chemical Formula 29]
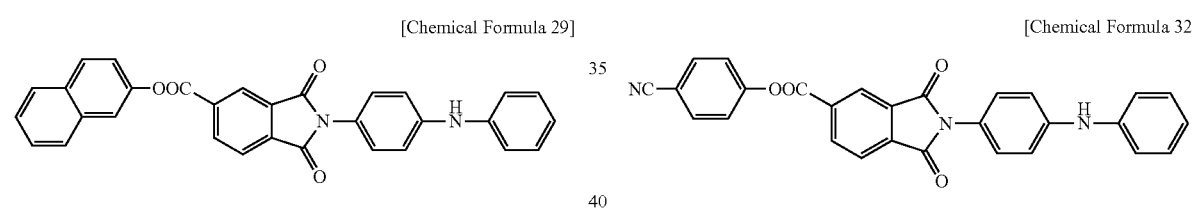
Compound 5
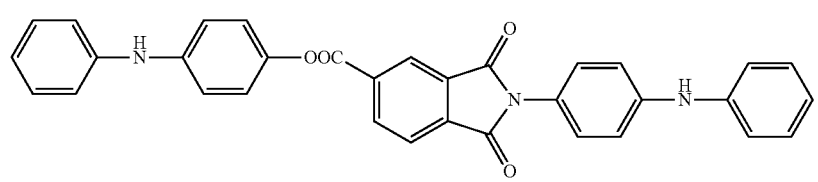
Compound 6
[Chemical Formula 31]
Compound 7
[Chemical Formula 32]
Compound 8
[Chemical Formula 30]
[Chemical Formula 33]
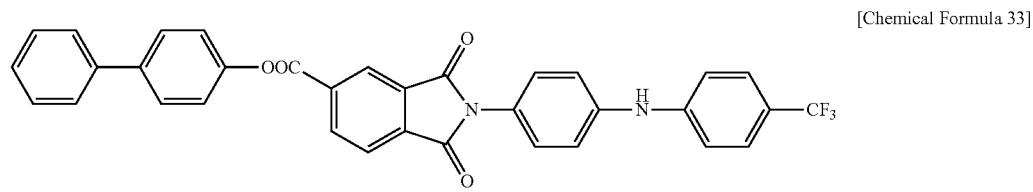

Among them, since compound 8 has a group having high electron-withdrawing properties (—CF$_3$ group) also on the phenyl group that is not the phenyl group to which R$^2$ is linked via a phthalimide structure in the diarylamine skeleton, specifically the diphenylamine skeleton, the compound can provide a particularly excellent effect of enhancing heat resistance, as will be described below.

2. Method of Producing Diarylamine Compound Represented by Formula (I)

There are no particular limitations on the method of producing a diarylamine compound represented by the formula (I) which has at least one signal attributable to the hydrogen of the N—H moiety at 8.30 ppm to 9.00 ppm when a deuterated dimethyl sulfoxide solution of the compound is analyzed by $^1$H-NMR. However, for example, the diarylamine compound can be simply produced by a method in which, in a first stage, an intermediate of formula (b) having a phthalimide structure is produced by allowing 4-aminodiphenylamine to react, in a heated solution, with an aromatic 1,2-dicarboxylic acid anhydride substituted with a group containing carbonyl groups, as represented by formula (a), in which —C(=O)—OH, —OH, —NH$_2$ or —NHR$^0$ (wherein R$^0$ simply means any organic group) is present at the 4-position, and thereby forming an imide bond:

[Chemical Formula 34]

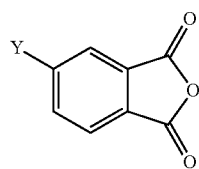

(a)

wherein Y represents —C(=O)—OH, —OH, —NH$_2$ or —NHR$^0$;

[Chemical Formula 35]

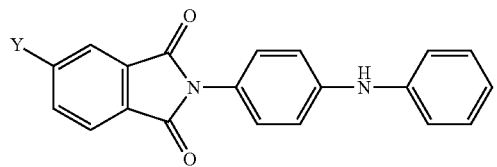

(b)

wherein Y has the same meaning as in the formula (a); and subsequently, in a second stage, the substituent (Y) present at the 4-position of the phthalimide structure is allowed to react with a compound having a hydroxyl group, a carboxyl group, an amino group or the like, or with a naphthol compound or the like in a solution, and thereby the desired compound can easily be produced. Particularly, when Y is —C(=O)—OH, an esterification reaction can be carried out relatively easily by using a catalyst such as N,N-dimethyl-4-aminopyridine.

Furthermore, when there is a need to use 4-aminodiphenylamine having a substituent in the first stage, as in the case of producing the compound 8, it is preferable to produce 4-aminodiphenylamine having a substituent by, for example, employing a method of subjecting an aryl halide and a substituted aniline to a cross-coupling reaction in the presence of copper(II) oxide.

3. Production Method in the Case where the Diarylamine Compound Represented by Formula (I) is a Phthalimide Group-Containing Diarylamine Compound Having an Ester Group at the 4-Position When it is intended to produce a phthalimide group-containing diarylamine compound having an ester group at the 4-position, in which Y in the formula (b) is —C(=O)—OR$^0$ (wherein R$^0$ simply means any organic group), application of a method of producing a phthalimide compound having an ester group at the 4-position can be conceived.

Specifically, Japanese Examined Patent Application (JP-B) No. 5-53789 discloses a method for production in three processes using trimellitic anhydride and an aniline derivative as starting raw materials, as represented by the following reaction scheme (P1):

[Chemical Formula 36]

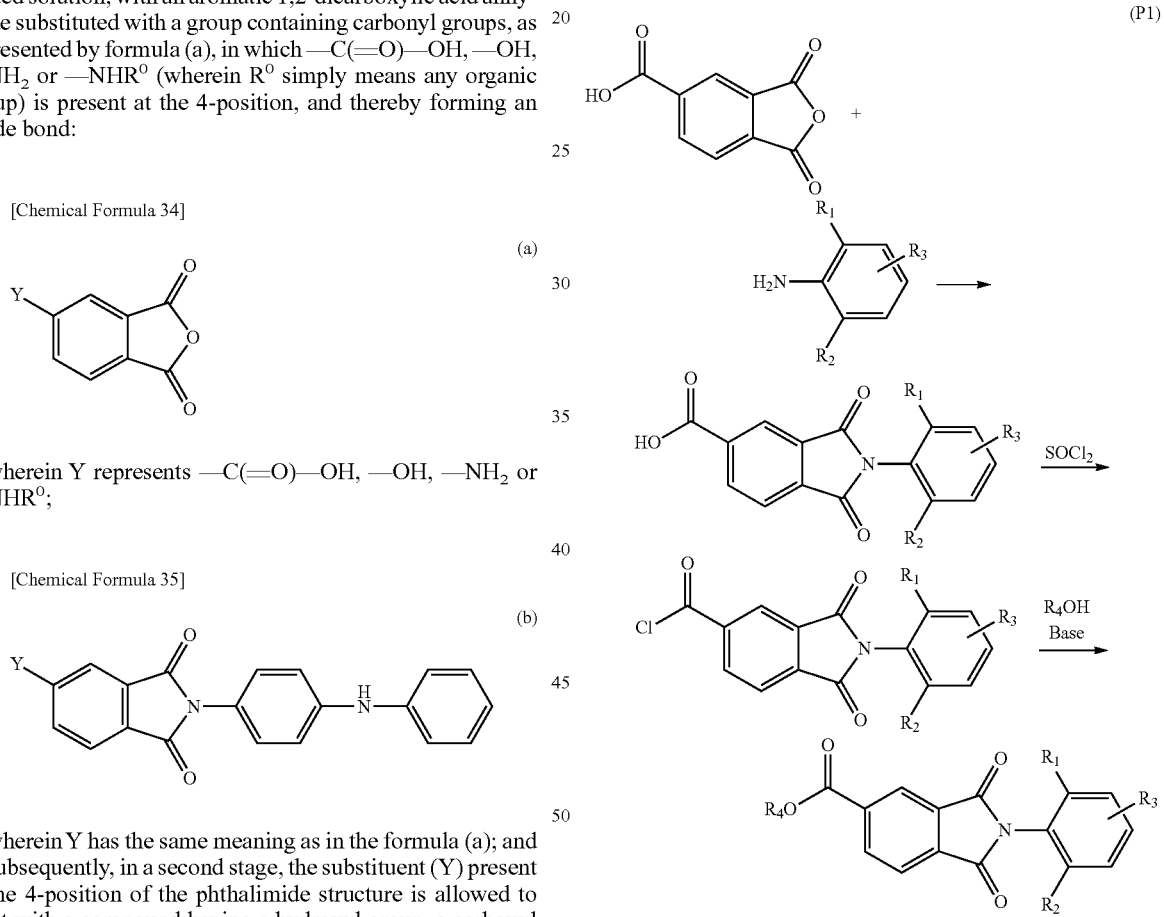

wherein in the reaction scheme (P1),

R$_1$ and R$_2$ each independently represent a lower alkyl group or a lower alkenyl group;

R$_3$ represents a hydrogen atom, a halogen atom, or a lower alkyl group; and

R$_4$ represents an alkyl group, a lower alkenyl group, a lower alkynyl group, a cycloalkyl group which may be substituted with a lower alkyl group, an aralkyl group which may have a substituent, a phenyl group which may have a substituent, a di-lower alkylamino group, a 5-membered ring or 6-membered ring heterocyclic group containing an N atom and/or an O atom.

In the production method employing the reaction scheme (P1), different solvents are used in the respective processes, and there is a need to perform purification of the product at each process, making the process complicated. Furthermore, in this production method, it is necessary to use thionyl chloride in order to convert the carboxyl group at the 4-position of the phthalimide group into an acid chloride group. Thionyl chloride is a chlorinating agent with high reactivity, and when use is made of an aniline derivative in which a substituent having active hydrogen, such as an amine or an alcohol, has been introduced as $R_3$, thionyl chloride also reacts with such a substituent. For this reason, the production method is limited in terms of the raw materials to be used.

Disclosed in Bioorganic & Medicinal Chemistry Letters, Vol. 19, No. 3, p. 878-881 (2009) is a method of allowing a phthalimide compound having a carboxyl group at the 4-position and a compound containing a hydroxyl group (ROH) to react in the presence of a condensing agent by the following reaction scheme (P2):

[Chemical Formula 37]

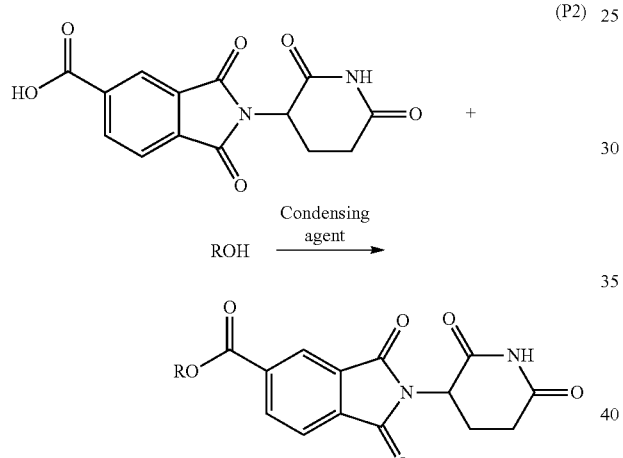

(P2)

and thereby esterifying the carboxyl group. According to this method, a phthalimide compound having an ester group at the 4-position, can be produced by a one-stage reaction. Representative examples of the condensing agent include N,N'-dicyclohexylcarbodiimide (DCC), and 1-ethyl-3-(3-dimethylaminopropyl)carbodiimide hydrochloride (WSC).

However, when DCC is used as the condensing agent, dicyclohexylurea, which is a side product, is insoluble in organic solvents, and therefore, purification by crystallization or recrystallization of the target compound obtained by the reaction is difficult. On the other hand, because WSC is a highly expensive reagent, the method is not an industrially advantageous production method in view of production cost.

As another method of producing a phthalimide compound having an ester group at the 4-position, a method of using trimellitic anhydride chloride as a starting raw material can be considered. Disclosed in JP-A No. 63-172154 is a method of allowing trimellitic anhydride and a compound containing a hydroxyl group (ROH) in the presence of a base according to the following reaction scheme (P3):

[Chemical Formula 38]

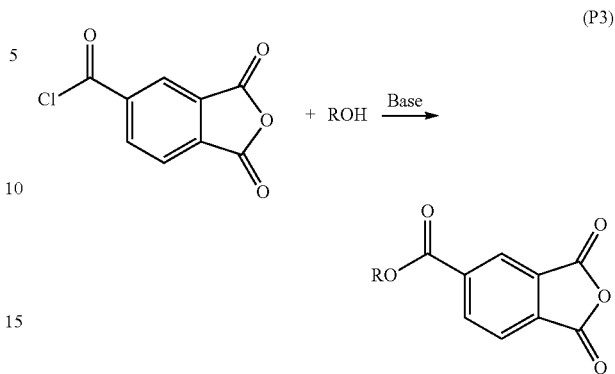

(P3)

and thereby converting the carboxyl group at the 4-position of trimellitic anhydride to an ester group.

Furthermore, disclosed in JP-A No. 60-237064 is a method of allowing a trimellitic anhydride derivative in which the carboxyl group at the 4-position of trimellitic anhydride has been converted to an ester group, to react with aniline according to the following reaction scheme (P4):

[Chemical Formula 39]

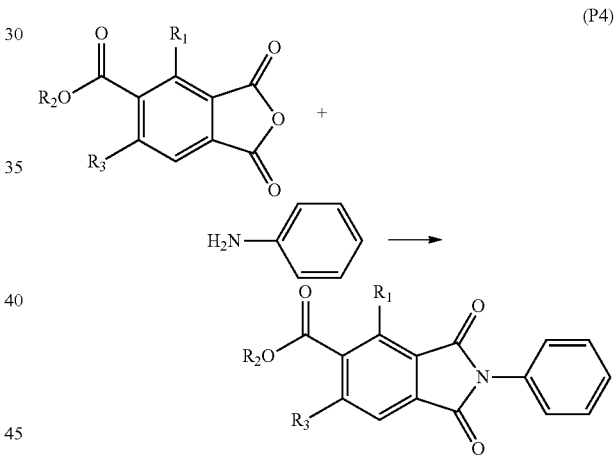

(P4)

(wherein $R_1$, $R_2$ and $R_3$ each represent an alkyl group), and thereby producing a phthalimide compound having an ester group at the 4-position.

However, the method which combines the reaction schemes (P3) and (P4) is not industrially advantageous as a method of producing a phthalimide compound having an ester group at the 4-position, because the types of the solvents used in the various processes are different, large amounts of solvents are used, and purification in the various processes is troublesome.

The inventors of the present invention found a method of producing a phthalimide group-containing diarylamine compound having an ester group at the 4-position, for example, N-(4-phenylaminophenyl)-phthalimide compound, with high efficiency and with a high yield.

That is, a production method including three processes, such as Process 1 of first allowing a trimellitic anhydride halide compound to react with a hydroxyl group-containing compound in an organic solvent in the presence of a base and thereby producing a trimellitic anhydride ester compound having an ester group at the 4-position; Process 2 of allowing the trimellitic anhydride ester compound to react with an amino group-containing diarylamine compound in an organic solvent, and thereby producing an amide acid compound; and Process 3 of heating the reaction solution containing the amide acid compound to imidate the amide acid compound, can be applied.

Next, the inventors found a method in which those three processes are combined in the above-described order, and thereby, the esterification, amide oxidation, and imidation of a trimellitic anhydride halide compound can be carried out in a one-pot process using the same organic solvent in the same reactor. Furthermore, the inventors also found that when this method is used, there is no need to perform complicated purification processes at each process, and after completion of the reaction, a phthalimide group-containing diarylamine compound having an ester group at the 4-position can be recovered with a high yield as crystals of high purity, through filtration of the reaction solution that has been cooled.

According to this production method of the present invention, a phthalimide group-containing diarylamine compound having an ester group at the 4-position, which is represented by N-(4-phenylaminophenyl)-phthalimide compound having an ester group at the 4-position, and is useful as an aging inhibitor (oxidation inhibitor) for polymers, can be obtained with high efficiency and with a high yield.

Therefore, according to the present invention, there is provided a method of producing a phthalimide group-containing diarylamine compound having an ester group at the 4-position, which is represented by the following formula (VII):

[Chemical Formula 46]

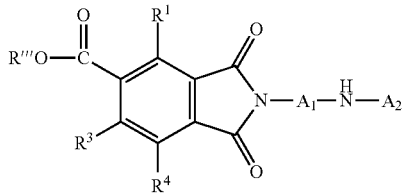

(VII)

and has at least one signal attributable to the hydrogen of the N—H moiety at 8.30 ppm to 9.00 ppm when a deuterated dimethyl sulfoxide solution of the diarylamine compound is analyzed by $^1$H-NMR, the method including three processes, such as Process 1 of allowing a trimellitic anhydride halide compound represented by the following formula (IV):

[Chemical Formula 40]

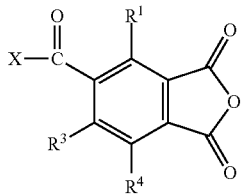

(IV)

wherein in the formula (IV), $R^1$, $R^3$ and $R^4$ each independently represent a hydrogen atom, a halogen atom, an alkyl group having 1 to 10 carbon atoms which may have a substituent, a cyano group, a nitro group, —OR, —O—C(=O)—R, —C(=O)—OR, —O—C(=O)—OR, —NR'—C(=O)—R, —C(=O)—NRR⁰, or —O—C(=O)—NRR⁰;

R and R⁰ each independently represent a hydrogen atom, or an organic group having 1 to 30 carbon atoms which may have a substituent;

the relevant organic group may be an organic group which is interrupted by at least one linking group selected from the group consisting of —O—, —S—, —O—C(=O)—, —C(=O)—O—, —O—C(=O)—O—, —NR"—C(=O)—, —C(=O)—NR"—, —NR"—, and —C(=O)—, but organic groups which are interrupted by two or more contiguous —O— or —S— moieties are excluded;

R' and R" each independently represent a hydrogen atom, or an alkyl group having 1 to 6 carbon atoms;

the relevant substituent includes a halogen atom, a cyano group, or a nitro group; and X represents a halogen atom, to react with a hydroxyl group-containing compound represented by the following formula (V):

[Chemical Formula 41]

$$R'''OH \qquad (V)$$

wherein in the formula (V),

R''' represents an alkyl group having 1 to 10 carbon atoms which may have a substituent, or an aromatic group having 4 to 30 carbon atoms which may have a substituent;

the relevant substituents are each independently a halogen atom, an alkyl group having 1 to 10 carbon atoms, an aralkyl group having 1 to 20 carbon atoms, an aromatic group having 6 to 30 carbon atoms, a cyano group, a nitro group, a sulfo group, —OR$^a$, —O—C(=O)—R$^a$, —C(=O)—OR$^a$, —O—C(=O)—OR$^a$, NR$^c$—C(=O)—R$^a$, —C(=O)—NR$^a$R$^b$, —O—C(=O)—NR$^a$R$^b$, —SR$^a$, —S(=O)—R$^a$, or —S(=O)$_2$—R$^a$; and R$^a$, R$^b$ and R$^c$ each independently represent a hydrogen atom, an alkyl group having 1 to 8 carbon atoms, or a phenyl group, in an organic solvent in the presence of a base, and thereby producing a trimellitic anhydride ester compound by the following reaction scheme (1):

[Chemical Formula 42]

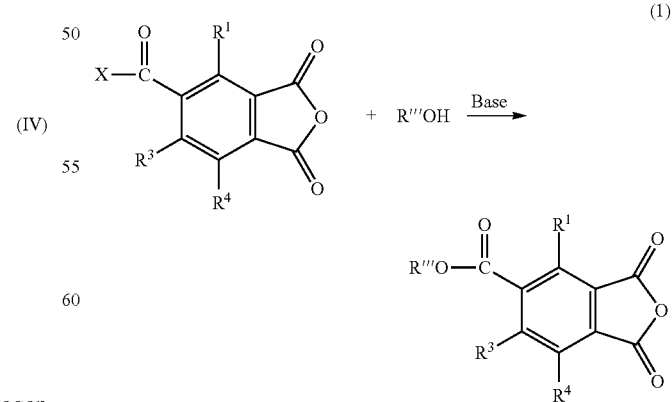

wherein the symbols used in the reaction scheme (1) respectively have the same meanings as defined above;

Process 2 of allowing the trimellitic anhydride ester compound produced in Process 1, to react with an amino group-containing diarylamine compound represented by the following formula (VI):

[Chemical Formula 43]

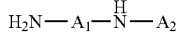
(VI)

wherein in the formula (VI), $A_1$ and $A_2$ each independently represent an aromatic group having 6 to 30 carbon atoms which may have a substituent; and the relevant substituents are each independently an alkyl group having 1 to 10 carbon atoms, a halogen-substituted alkyl group having 1 to 10 carbon atoms, a halogen atom, a cyano group, or a nitro group, in an organic solvent, and thereby producing an amide acid compound by the following reaction scheme (2):

[Chemical Formula 44]

(2)

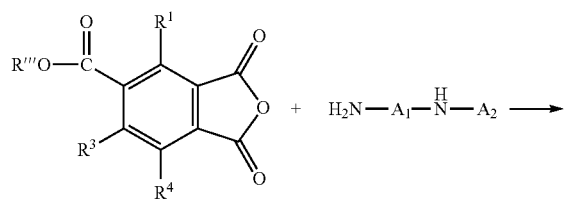

and/or

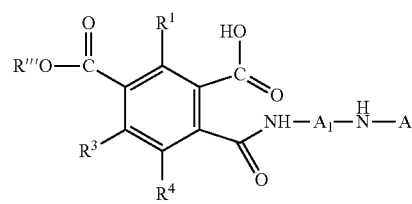

wherein the symbols used in the reaction scheme (2) respectively have the same meanings as defined above; and Process 3 of heating the reaction solution containing the amide acid compound produced in Process 2, and thereby imidating the amide acid compound by the following reaction scheme (3):

[Chemical Formula 45]

(3)

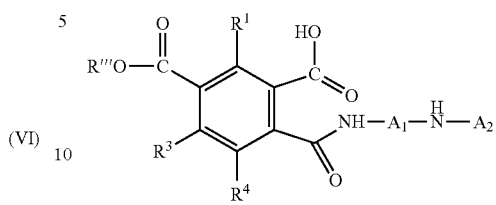

and/or

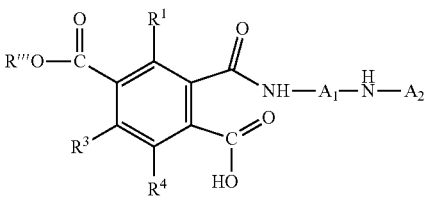

Heating
Imidation

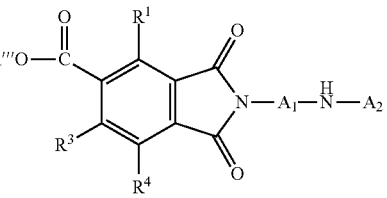

wherein the symbols used in the reaction formula (3) respectively have the same meanings as defined above, wherein these three processes are carried out in a one-pot process in the presence of an organic solvent.

In regard to the respective processes, the organic solvent is preferably at least one organic solvent selected from the group consisting of aprotic polar solvents and non-polar solvents. The organic solvent is more preferably a solvent mixture of an aprotic polar solvent and a non-polar solvent, even more preferably a solvent mixture of a nitrogen-containing aprotic polar solvent and an aromatic hydrocarbon-based non-polar solvent, and particularly preferably a solvent mixture of N,N-dimethylformamide and xylene.

According to the method of the present invention for producing a phthalimide group-containing diarylamine compound having an ester group at the 4-position, since three processes can be carried out in a one-pot process (a process for performing reactions in the same reactor), after completion of the reactions, the desired compound can be isolated simply through filtration of the reaction solution. For this reason, the method of the present invention for producing a phthalimide group-containing diarylamine compound having an ester group at the 4-position is such that the operation in the entire process is simple, the reaction time can be shortened, and an intended compound can be obtained with high efficiency and with a high yield. Therefore, the method of the present invention for producing a phthalimide group-containing diarylamine compound having an ester group at the 4-position exhibits high productivity, and is appropriate for industrial implementation.

Hereinafter, the method of the present invention for producing a phthalimide group-containing diarylamine compound having an ester group at the 4-position will be described in detail.

The method of the present invention for producing a phthalimide group-containing diarylamine compound having an ester group at the 4-position is a production method of carrying out three processes such as: (1) Process 1 of allowing a trimellitic anhydride halide compound to react with a hydroxyl group-containing compound in an organic solvent in the presence of a base, and thereby producing a trimellitic anhydride ester compound having an ester group at the 4-position; (2) Process 2 of allowing the trimellitic anhydride ester compound to react with an amino group-containing diarylamine compound in an organic solvent, and thereby producing an amide acid compound; and (3) Process 3 of heating the reaction solution containing the amide acid compound, and thereby imidating the amide acid compound; in an organic solvent in a one-pot process.

This Process 1 is a process of allowing a trimellitic acid anhydride compound and a hydroxyl group-containing compound to react according to the following reaction scheme (1):

[Chemical Formula 47]

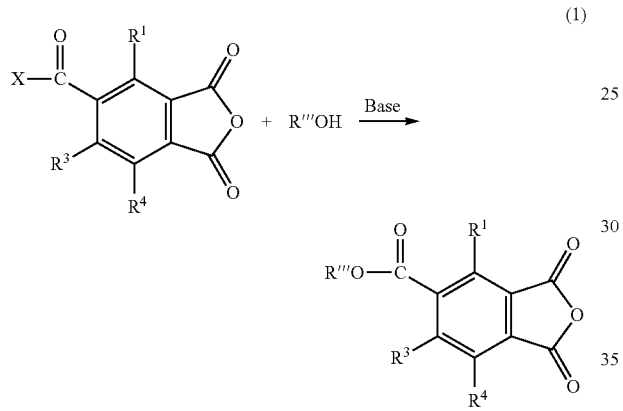

and thereby producing a trimellitic anhydride ester compound.

The trimellitic anhydride halide compound used as a starting raw material is a compound represented by the following formula (IV):

[Chemical Formula 48]

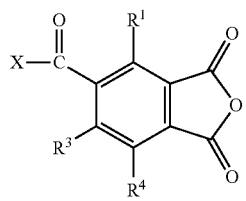

In the formula (IV), $R^1$, $R^3$ and $R^4$ each independently represent a hydrogen atom, a halogen atom, an alkyl group having 1 to 10 carbon atoms which may have a substituent, a cyano group, a nitro group, —OR, —O—C(=O)—R, —C(=O)—OR, —O—C(=O)—OR, —NR'—C(=O)—R, —C(=O)—NRR$^0$, or —O—C(=O)—NRR$^0$. Among these, from the viewpoint of the ease of synthesis, a hydrogen atom, or an alkyl group having 1 to 10 carbon atoms which may have a substituent is preferred, and a hydrogen atom is more preferred.

R and R$^0$ each independently represent a hydrogen atom, or an organic group having 1 to 30 carbon atoms which may have a substituent.

The relevant organic group may be an organic group which is interrupted by at least one linking group selected from the group consisting of —O—, —S—, —O—C(=O)—, —C(=O)—O—, —O—C(=O)—O—, —NR"—C(=O)—, —C(=O)—NR"—, —NR"— and —C(=O)—, but organic groups which are interrupted by two or more contiguous —O— or —S— moieties are excluded.

R' and R" each represent a hydrogen atom, or an alkyl group having 1 to 6 carbon atoms.

The relevant substituent includes a halogen atom, a cyano group, or a nitro group.

X represents a halogen atom (a fluorine atom, a chlorine atom, a bromine atom, an iodine atom, or the like). X is preferably a chlorine atom.

The trimellitic anhydride halide compound is preferably a compound of the following formula (IV-a):

[Chemical Formula 49]

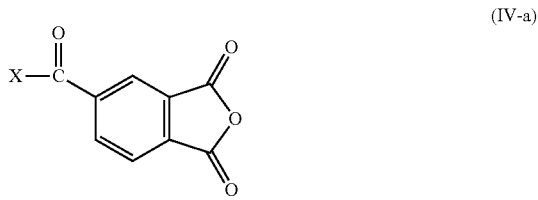

wherein in the formula (IV-a), X represents a halogen atom, and is more preferably a trimellitic anhydride chloride represented by the following formula (IV-b):

[Chemical Formula 50]

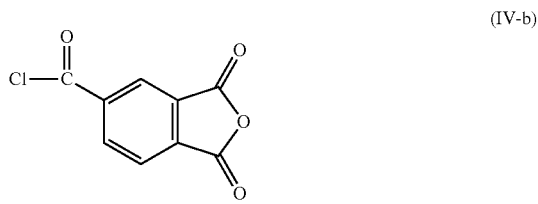

The hydroxyl group-containing compound of the other starting raw material is a compound represented by the following formula (V):

[Chemical Formula 51]

In the formula (V),

R'" represents an alkyl group having 1 to 10 carbon atoms which may have a substituent, or an aromatic group having 4 to 30 carbon atoms which may have a substituent. Examples of the aromatic group include benzene-based aromatic groups such as a phenyl group, a naphthyl group, an indanyl group, and an anthracenyl group; non-benzene-based aromatic groups such as an azulenyl group, and a pentalenyl group; and heteroaromatic groups such as a pyrrolyl group, a pyridinyl group, a furyl group, and a pyranyl group.

The relevant substituent is a halogen atom, an alkyl group having 1 to 10 carbon atoms, an aralkyl group having 1 to 20 carbon atoms, an aromatic group having 6 to 30 carbon atoms, a cyano group, a nitro group, a sulfo group, —OR$^a$, —O—C(=O)—R$^a$, —C(=O)—OR$^a$, —O—C(=O)—OR$^a$, —NR$^c$—C(=O)—R$^a$, —C(=O)—NR$^a$R$^b$, —O—C(=O)—NR$^a$R$^b$, —SR$^a$, —S(=O)—R$^a$, or —S(=O)$_2$—R$^a$.

R$^a$, R$^b$ and R$^c$ each independently represent a hydrogen atom, an alkyl group having 1 to 8 carbon atoms, or a phenyl group.

R''' in the above formula (V) is preferably an aromatic group having 4 to 30 carbon atoms which may have a substituent, and is more preferably a phenyl group having 6 to 25 carbon atoms which may have a substituent, or a naphthyl group having 10 to 30 carbon atoms which may have a substituent. The number of carbon atoms in such an aromatic group in the case where the aromatic group has a substituent, includes the number of carbon atoms of the substituent.

Among the substituents, preferred examples include a halogen atom, an alkyl group having 1 to 10 carbon atoms, an aralkyl group having 1 to 20 carbon atoms, an aromatic group having 6 to 30 carbon atoms, a cyano group, a nitro group, and —NR$^a$R$^b$. More preferred examples include an alkyl group having 1 to 10 carbon atoms, an aralkyl group having 1 to 20 carbon atoms, and an aromatic group having 6 to 30 carbon atoms, and an aromatic group having 6 to 30 carbon atoms is even more preferred. Among aromatic groups having 6 to 30 carbon atoms, a phenyl group is particularly preferred.

Specific preferred examples of the hydroxyl group-containing compound represented by the above formula (V) (R'''OH) include aromatic compounds having a phenolic hydroxyl group as represented by the following formulas (V-a) to (V-g):

[Chemical Formula 52]

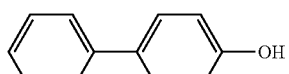
(V-a)

[Chemical Formula 53]

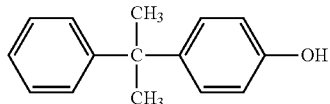
(V-b)

[Chemical Formula 54]

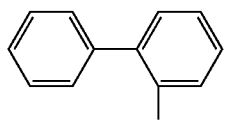
(V-c)

[Chemical Formula 55]

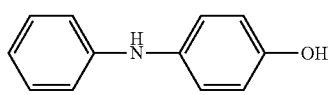
(V-d)

[Chemical Formula 56]

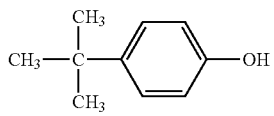
(V-e)

[Chemical Formula 57]

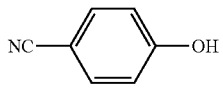
(V-f)

[Chemical Formula 58]

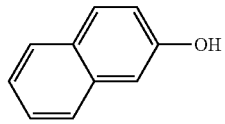
(V-g)

Examples of the base that is used in the reaction according to the reaction scheme (1) described above include, but are not limited to, tertiary amines such as triethylamine, diisopropylethylamine, and N-methylmorpholine; pyridines such as pyridine, picoline, lutidine, and 4-(dimethylamino)pyridine; and inorganic bases such as sodium hydroxide, potassium hydroxide, and potassium carbonate. Among these, triethylamine, diisopropylethylamine, and pyridine are preferred. The use amount of the base is preferably 1.0 to 2.0 equivalents, and more preferably 1.1 to 1.2 equivalents, based on the trimellitic anhydride halide compound.

Examples of the operation of this reaction include: (1) a method of adding R'''OH dropwise to a reaction system containing a trimellitic anhydride halide compound, a base and an organic solvent; (2) a method of adding a base dropwise to a reaction system containing a trimellitic anhydride halide compound, R'''OH and an organic solvent; and (3) a method of adding a liquid mixture of R'''OH, a base and an organic solvent dropwise to a reaction system containing a trimellitic anhydride halide compound and an organic solvent. Among these, a method of adding a base dropwise to a reaction system containing a trimellitic anhydride halide compound, R'''OH and an organic solvent is preferred from the viewpoint that the reaction heat can be suppressed.

The reaction temperature of this reaction is preferably between −30° C. and +40° C., and more preferably between 0° C. and +30° C. The reaction time is usually between tens of minutes and several hours.

In Process 2 as described above, the trimellitic anhydride ester compound produced in the Process 1 is allowed to react with an amino group-containing diarylamine compound represented by the following formula (VI):

[Chemical Formula 59]

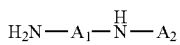
(VI)

wherein in the formula (VI),

A$_1$ and A$_2$ each independently represent an aromatic group having 6 to 30 carbon atoms which may have a substituent; and the relevant substituents each independently represent an alkyl group having 1 to 10 carbon atoms, a halogen-substituted alkyl group having 1 to 10 carbon atoms, a halogen atom, a cyano group, or a nitro group, in an organic solvent, and thereby an amide acid compound is produced by the following reaction scheme (2):

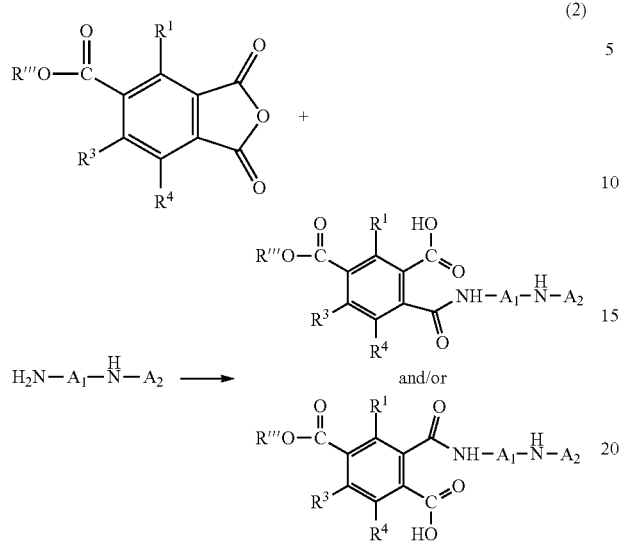

(2)

Examples of the alkyl group having 1 to 10 carbon atoms include a methyl group, an ethyl group, and a propyl group. Examples of the halogen atom include a fluorine atom, a chlorine atom, a bromine atom, and an iodine atom.

The amino group-containing diarylamine compound represented by the formula (VI) is preferably an amino group-containing diphenylamine compound represented by the following formula (VI-a) (identical with formula (VIII)):

[Chemical Formula 61]

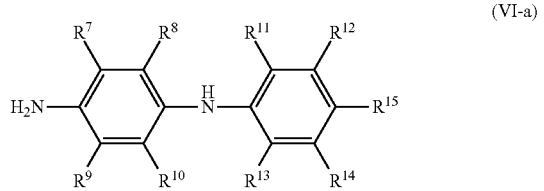

(VI-a)

wherein in the formula (VI-a),

R$^7$ to R$^{15}$ each independently represent a hydrogen atom, an alkyl group having 1 to 10 carbon atoms, a halogen-substituted alkyl group having 1 to 10 carbon atoms, a halogen atom, a cyano group, or a nitro group.

Furthermore, the amino group-containing diarylamine compound represented by the formula (VI) is more preferably an amino group-containing diphenylamine compound represented by the following formula (VI-b) (identical with formula (X)):

[Chemical Formula 62]

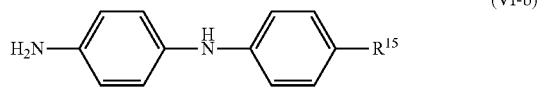

(VI-b)

wherein in the formula (VI-b),

R$^{15}$ represents a hydrogen atom, an alkyl group having 1 to 10 carbon atoms, a halogen-substituted alkyl group having 1 to 10 carbon atoms, a halogen atom, a cyano group, or a nitro group.

Specific examples of the amino group-containing diarylamine compound represented by the formula (VI), more particularly by the formula (VI-b) (formula (X)), include 4-aminodiphenylamine represented by the following formula (VI-c):

[Chemical Formula 63]

(VI-c)

and 4-amino-4'-trifluoromethyldiphenylamine represented by the following formula (VI-d):

[Chemical Formula 64]

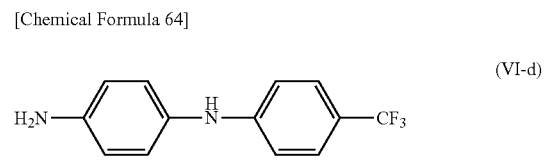

(VI-d)

Process 2 as expressed by the reaction scheme (2) is a process of allowing the trimellitic anhydride ester compound produced in the Process 1 to react with an amino group-containing diarylamine compound in an organic solvent, and thereby producing an amide acid compound. In this Process 2, the amino group-containing diarylamine compound is added to the reaction solution obtained in the Process 1, and thus an amide acid compound is synthesized. The reaction temperature of this reaction is preferably between −30° C. and +60° C., and more preferably between 0° C. and +40° C. The reaction time is usually between several minutes and several hours.

In Process 3, the reaction solution containing the amide acid compound produced in the Process 2 is heated, and thereby the amide acid compound is imidated by the following reaction scheme (3):

[Chemical Formula 65]

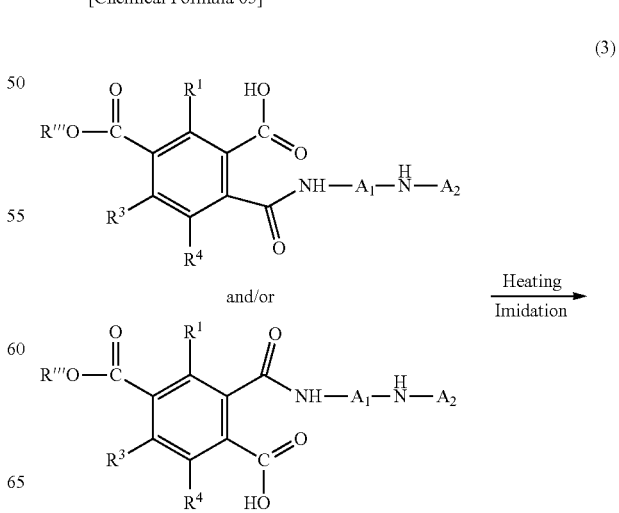

(3)

-continued

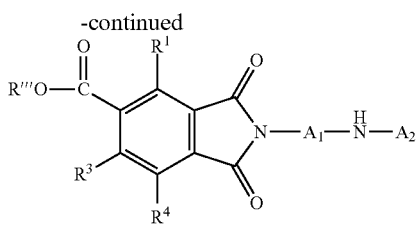

Through the imidation in the Process 3, a phthalimide group-containing diarylamine compound having an ester group at the 4-position can be synthesized.

The reaction temperature in the Process 3 is preferably 80° C. to 250° C., and more preferably 120° C. to 160° C. The reaction time is usually several hours. It is desirable that the imidation reaction be carried out by a method of heating the reaction solution to reflux.

This imidation reaction is usually carried out in the presence of an acid catalyst or a base catalyst. Examples of the acid that may be used as the acid catalyst include, but are not limited to, inorganic acids such as hydrochloric acid, sulfuric acid, and phosphoric acid; and organic acids such as p-toluenesulfonic acid, 10-camphorsulfonic acid, and acetic acid. Examples of the base that may be used as the base catalyst include, but are not limited to, tertiary amines such as triethylamine, diisopropylethylamine, and N-methylmorpholine; pyridines such as pyridine, picoline, lutidine, and 4-(dimethylamino)pyridine; and inorganic bases such as sodium hydroxide, potassium hydroxide, and potassium carbonate. Among these, base catalysts are preferred, and among the base catalysts, triethylamine, diisopropylethylamine, and pyridine are more preferred.

The use amount of the acid catalyst used in the imidation reaction is in the range of [[equivalent of the base used in Process 1-1]+0.5 to 1.5] equivalents. The use amount of the base catalyst is preferably 0.05 to 1.5 equivalents, and more preferably 0.1 to 0.5 equivalents, based on the trimellitic anhydride halide used as a raw material in Process 1.

The base catalyst used in the imidation reaction is preferably the same base as that used in the Process 1. It is preferable to employ a method in which an excess amount of a base is used in Process 1, and no base is further added in Process 3. That is, it is desirable to make the excess amount of base which does not participate in the reaction of Process 1, to act as an imidation catalyst in Process 3.

The method of the present invention for producing a phthalimide group-containing diarylamine compound having an ester group at the 4-position is characterized by including the three processes described above, and carrying out these three processes in a one-pot process in the presence of an organic solvent. Examples of the organic solvent used in these three processes include non-polar solvents, including ether-based non-polar solvents such as 1,2-dimethoxyethane, 1,4-dioxane, and tetrahydrofuran (THF); aromatic hydrocarbon-based non-polar solvents such as benzene, toluene, and xylene; and aprotic polar solvents, including nitrogen-containing aprotic polar solvents such as N,N-dimethylformamide (DMF), N,N-dimethylacetamide, hexamethylphosphoric acid triamide, and N-methylpyrrolidone (NMP); ketone-based aprotic polar solvents such as acetone, methyl ethyl ketone (MEK), and methyl isobutyl ketone (MIBK); and ester-based aprotic polar solvents such as ethyl acetate and butyl acetate. However, the solvent is preferably a solvent mixture including two or more kinds of these. Among these, a solvent mixture of an aprotic polar solvent and a non-polar solvent is more preferred, and a solvent mixture of a nitrogen-containing aprotic polar solvent and an aromatic hydrocarbon-based non-polar solvent is even more preferred, while a solvent mixture of N,N-dimethylformamide and xylene is particularly preferred.

The use amount of the organic solvent is usually 50 to 2000 parts by weight, and preferably 1000 to 1200 parts by weight, relative to 100 parts by weight of the trimellitic anhydride halide compound used as a raw material in Process 1.

The solvent mixture of a nitrogen-containing aprotic polar solvent and an aromatic hydrocarbon-based non-polar solvent, such as a solvent mixture of N,N-dimethylformamide and xylene, is preferably such that the mixing ratio (volume ratio) of the two solvents is preferably such that nitrogen-containing aprotic polar solvent:aromatic hydrocarbon-based non-polar solvent=5:95 to 50:50, and more preferably 5:95 to 20:80. In many cases, when a solvent mixture of N,N-dimethylformamide:xylene=5:95 to 20:80 is used, particularly satisfactory results can be obtained.

In the Process 3, as the imidation reaction proceeds, the target compound is precipitated in the reaction solution. It is desirable that, after completion of the reaction, the reaction solution be cooled, a poor solvent which does not dissolve the target compound be added, and the target compound completely be precipitated. The poor solvent is preferably a lower alcohol having 1 to 5 carbon atoms, such as methanol.

When a lower alcohol such as methanol is used as the poor solvent, the addition amount is usually 100 to 1000 parts by weight, and preferably 200 to 300 parts by weight, relative to 100 parts by weight of the trimellitic anhydride halide compound used in Process 1. The temperature of the reaction solution at the time of adding the alcohol is usually 0° C. to 70° C., and preferably 40° C. to 60° C.

The method of adding the alcohol may be a method of continuously adding the alcohol in small amounts while stirring the reaction solution; or a method of adding the alcohol in divided certain portions while stirring the reaction solution.

When a poor solvent such as methanol is added to the reaction solution obtained in the Process 3, salts as side products are completely dissolved, and only the target compound will be precipitated. For this reason, the desired compound can be isolated with a high yield only by a simple operation such as filtration of the reaction solution. The structure of the desired compound can be identified by a spectroscopic analysis such as NMR spectroscopy, IR spectroscopy or mass spectroscopy, and/or by an elemental analysis.

According to the method of the present invention for producing a phthalimide group-containing diarylamine compound having an ester group at the 4-position, a phthalimide group-containing diarylamine compound having an ester group at the 4-position can be obtained with high efficiency and with a high yield through a one-pot process. The one-pot process means a method of carrying out the reactions of respective processes in the same reactor; however, even for the organic solvent used for the reactions, it is preferable to use substantially the same organic solvent in the various processes.

The production method of the present invention includes the three processes which are based on the reaction scheme (1) to the reaction scheme (3). The production method of the present invention preferably includes three processes based on the following reaction scheme (1a):

[Chemical Formula 66]
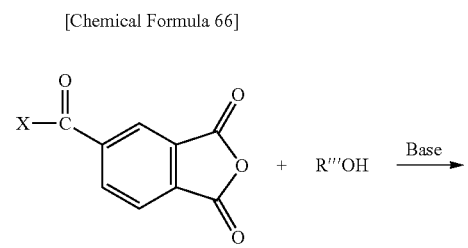
+ R''''OH →(Base) 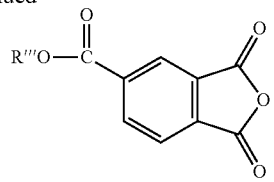
(1a)
wherein symbol R'''' in the reaction scheme (1a) has the same meaning as defined above,
the following reaction scheme (2a):
[Chemical Formula 67]
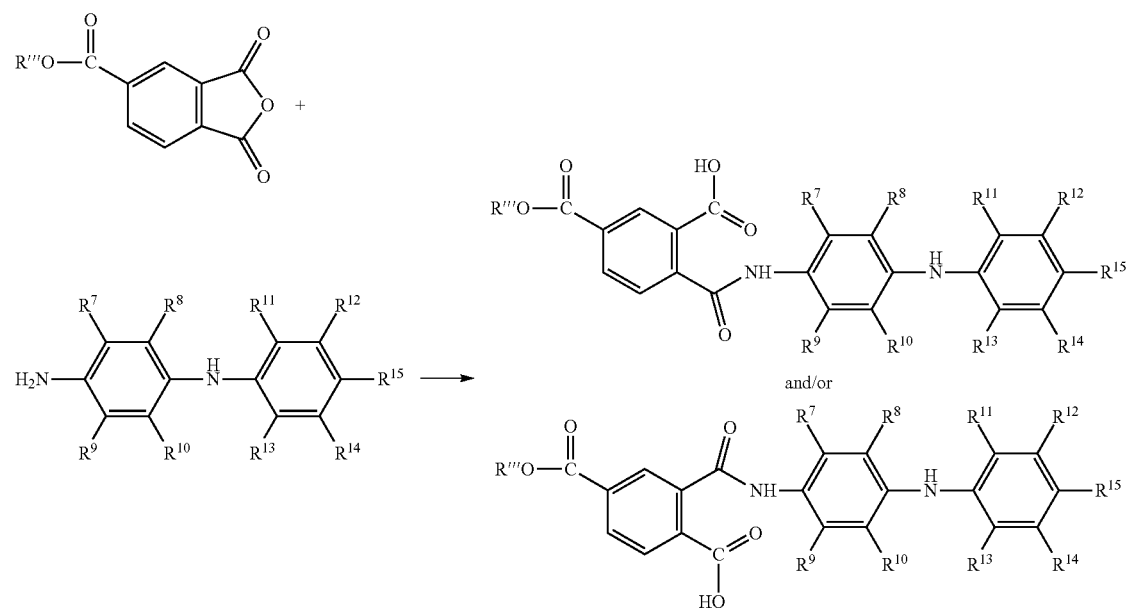
(2a)
wherein the symbols used in the reaction scheme (2a) respectively have the same meanings as defined above, and
the following reaction scheme (3a):
[Chemical Formula 68]
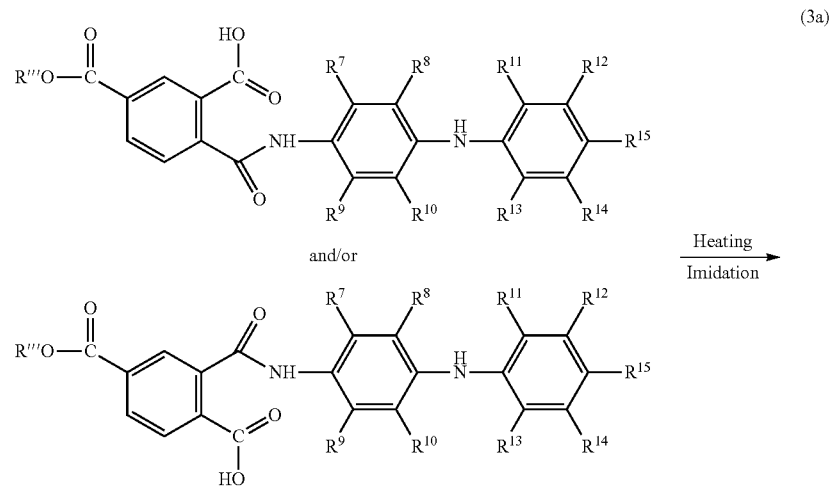
(3a)

-continued

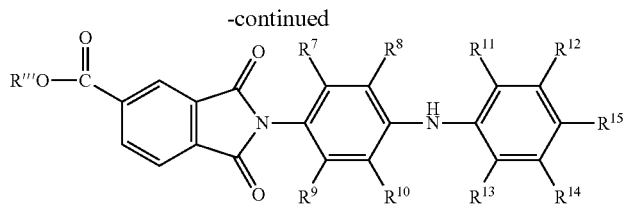

10 wherein the symbols used in the reaction scheme (3a) respectively have the same meanings as defined above.

A representative production method of the present invention includes three processes based on the following reaction scheme (1b):

[Chemical formula 69]

(1b)

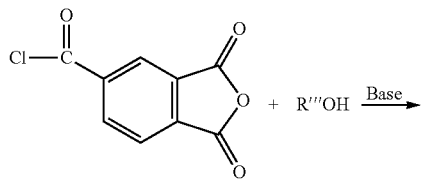

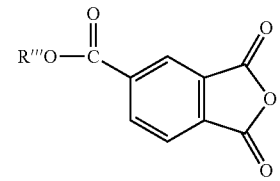

wherein symbol R''' in the reaction scheme (1b) has the same meaning as defined above, the following reaction scheme (2b):

[Chemical Formula 70]

(2b)

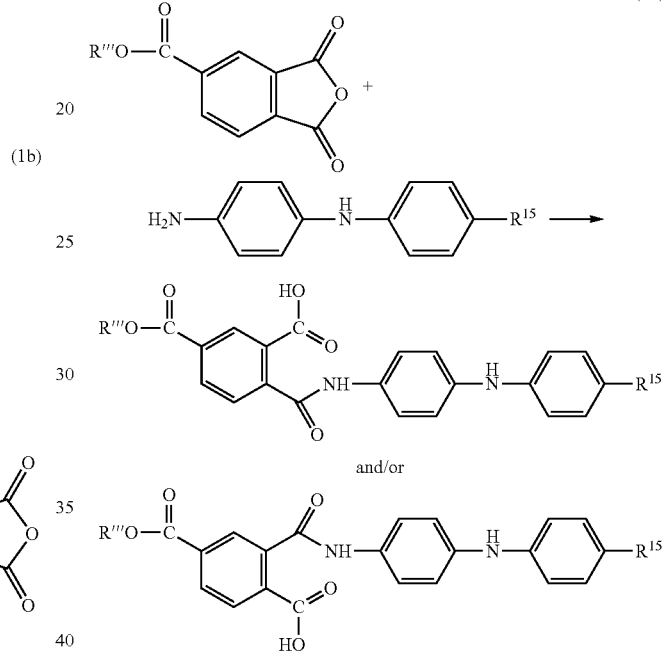

wherein the symbols used in the reaction scheme (2b) respectively have the same meanings as defined above, and the following reaction scheme (3b):

[Chemical Formula 71]

(3b)

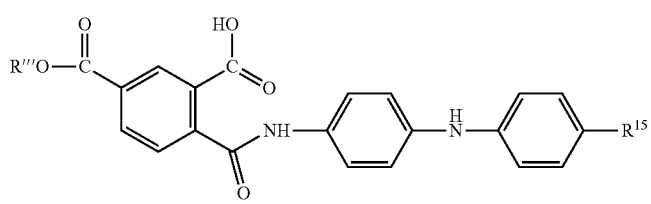

and/or

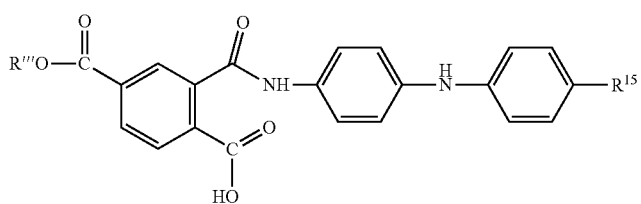

Heating
Imidation

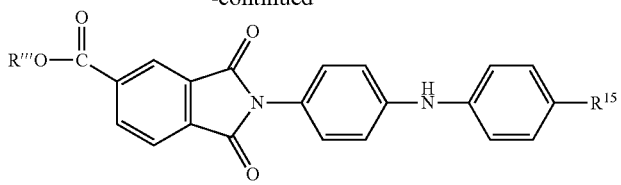

wherein the symbols used in the reaction scheme (3b) respectively have the same meanings as defined above.

The phthalimide group-containing diarylamine compound having an ester group at the 4-position, which is obtained by the production method of the present invention, is a compound represented by the following formula (VII):

[Chemical Formula 72]

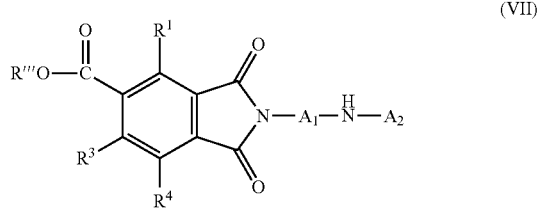

(VII)

wherein the symbols used in the formula (VII) respectively have the same meanings as defined above.

The phthalimide group-containing diarylamine compound having an ester group at the 4-position is preferably a phthalimide group-containing diphenylamine compound having an ester group at the 4-position, as represented by the following formula (IX):

[Chemical Formula 73]

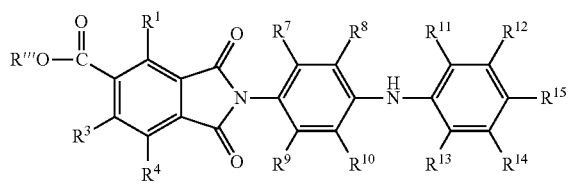

(IX)

wherein the symbols used in the formula (IX) respectively have the same meanings as defined above.

The phthalimide group-containing diarylamine compound having an ester group at the 4-position is more preferably a phthalimide group-containing diphenylamine compound having an ester group at the 4-position, as represented the following formula (XI):

[Chemical Formula 74]

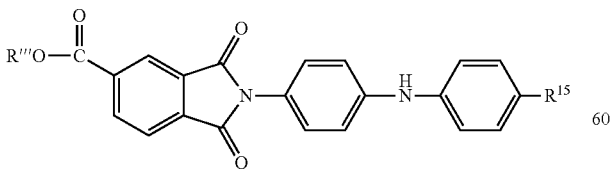

(XI)

wherein the symbols used in the formula (XI) respectively have the same meanings as defined above.

Suitable specific examples of the phthalimide group-containing diarylamine compound having an ester group at the 4-position include the compound 1 to compound 8 mentioned in connection with the explanation of the formula (I).

4. Diarylamine Compound Represented by Formula (II)

The diarylamine compound of the present invention represented by formula (II), which has at least one signal attributable to the hydrogen of the N—H moiety at 8.30 ppm to 9.00 ppm when a deuterated dimethyl sulfoxide solution of the diarylamine compound is analyzed by $^1$H-NMR, is a diarylamine compound represented by:

[Chemical Formula 75]

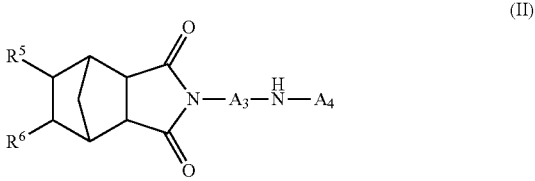

(II)

wherein in the formula (II), $A_3$ and $A_4$ each independently represent an aromatic group which may have a substituent having 1 to 30 carbon atoms;

$R^5$ and $R^6$ each independently represent a hydrogen atom, a halogen atom, an alkyl group having 1 to 10 carbon atoms which may have a substituent, a cyano group, a nitro group, —OR, —O—C(=O)—R, —C(=O)—OR, —O—C(=O)—OR, —NR'—C(=O)—R, —C(=O)—NRR$^0$, or —O—C(=O)—NRR$^0$;

R and R$^0$ each independently represent a hydrogen atom, or an organic group having 1 to 30 carbon atoms which may have a substituent;

the relevant organic group may be an organic group which is interrupted by at least one linking group selected from the group consisting of —O—, —S—, —O—C(=O)—, —C(=O)—O—, —O—C(=O)—O—, —NR"—C(=O)—, —C(=O)—NR"—, —NR"—, and —C(=O)—, but organic groups which are interrupted by two or more contiguous —O— or —S— moieties are excluded; and R' and R" each independently represent a hydrogen atom, or an alkyl group having 1 to 6 carbon atoms.

Preferably, a diarylamine compound represented by the formula (II), wherein:

$A_3$ represents a phenylene group which may have a substituent having 1 to 30 carbon atoms;

$A_4$ represents a phenyl group which may have a substituent having 1 to 30 carbon atoms;

$R^5$ and $R^6$ each independently represent a hydrogen atom, —O—C(=O)—R, —C(=O)—OR, —NR'—C(=O)—R, —C(=O)—NRR$^0$, or —O—C(=O)—NRR$^0$;

R and R$^0$ each represent an organic group having 1 to 30 carbon atoms which may have a substituent;

the relevant organic group may be an organic group which is interrupted by at least one linking group selected from the group consisting of —O—, —S—, —O—C(=O)—, —C(=O)—O—, —O—C(=O)—O—, —NR"—C(=O)—, —C(=O)—NR"—, —NR"—, and —C(=O)—, but organic groups which are interrupted by two or more contiguous —O— or —S— moieties are excluded; and R' and R" each independently represent a hydrogen atom, or an alkyl group having 1 to 6 carbon atoms.

More preferably, a diarylamine compound represented by the formula (II), in which $R^5$ and $R^6$ are both hydrogen atoms, can be selected.

The diarylamine compound represented by the formula (II), which can be used in the aging inhibitor of the present invention, is not particularly limited as long as the compound satisfies the formula (II), but from the viewpoint of providing an excellent effect of enhancing heat resistance, a particularly preferred compound is compound 9 shown below.

Compound 9

[Chemical Formula 76]

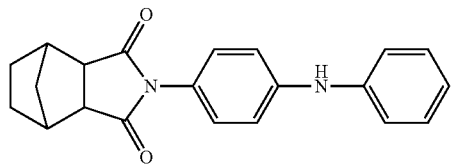

5. Method of Producing Diarylamine Compound Represented by Formula (II)

The method of the present invention for producing the diarylamine compound represented by the formula (II), which has at least one signal attributable to the hydrogen of the N—H moiety at 8.30 ppm to 9.00 ppm when a deuterated dimethyl sulfoxide solution is analyzed by $^1$H-NMR, is not particularly limited. However, the diarylamine compound represented by the formula (II) can be simply produced by, for example, a method of allowing, in a first stage, 4-aminodiphenylamine to react with 5-norbornene-2,3-dicarboxylic acid anhydride in a solution, and thereby producing an Intermediate in which diphenylamine and a norbornene-based compound are conjugated by an imide bond; and subsequently, in a second stage, hydrogenating the C=C bond in the norbornene, and thereby producing a target compound as a norbornane.

6. Diarylamine Compound Represented by Formula (III)

The diarylamine compound of the present invention represented by formula (III), which has at least one signal attributable to the hydrogen of the N—H moiety at 8.30 ppm to 9.00 ppm when a deuterated dimethyl sulfoxide solution of the diarylamine compound is analyzed by $^1$H-NMR, is a diarylamine compound represented by formula (III):

[Chemical Formula 77]

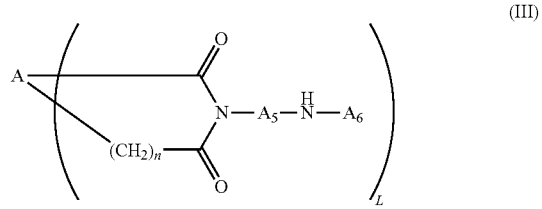

wherein in the formula (III),
A represents an aromatic group having 6 to 30 carbon atoms which may have a substituent, or a cyclic aliphatic group having 4 to 30 carbon atoms which may have a substituent;
L represents 1 or 2, and n represents 0 or 1;
the following formula (iii-1) corresponds to the following formula (iii-2):
Formula (iii-1)

[Chemical Formula 78]

Formula (iii-2)

[Chemical Formula 79]

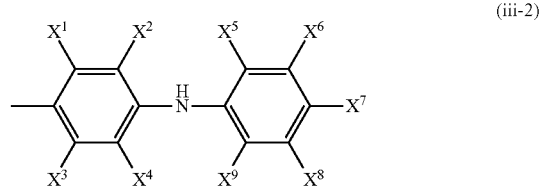

$X^1$ to $X^9$ each independently represent a hydrogen atom, a halogen atom, an alkyl group having 1 to 10 carbon atoms which may have a substituent, a cyano group, a nitro group, —OR, —O—C(=O)—R, —C(=O)—OR, —O—C(=O)—OR, —NW—C(=O)—R, —C(=O)—NRR$^0$, or —O—C(=O)—NRR$^0$;
R and R$^0$ each independently represent a hydrogen atom, or an organic group having 1 to 30 carbon atoms which may have a substituent;
the relevant organic group may be an organic group which is interrupted by at least one linking group selected from the group consisting of —O—, —S—, —O—C(=O)—, —C(=O)—O—, —O—C(=O)—O—, —NR"—C(=O)—, —C(=O)—NR"—, —NR"—, and —C(=O)—, but organic groups which are interrupted by two or more contiguous —O— or —S— moieties are excluded; and
R' and R" each independently represent a hydrogen atom, or an alkyl group having 1 to 6 carbon atoms.

As the diarylamine compound represented by the formula (III), preferably, a diarylamine compound in which the A is one selected from the group consisting of a phenyl group which may have a substituent, a 5-membered ring cyclic aliphatic group which may have a substituent, a 6-membered ring cyclic aliphatic group which may have a substituent, and a bicyclo[2.2.1]heptyl group which may have a substituent, can be selected.

Here, as the substituent for the moiety A, a hydrogen atom, a halogen atom, an alkyl group having 1 to 20 carbon atoms, a cycloalkyl group having 1 to 20 carbon atoms, an alkenyl group having 1 to 20 carbon atoms, an aralkyl group having 1 to 20 carbon atoms, a cyano group, a nitro group, —$OR^x$, —O—C(=O)—$R^x$, —C(=O)—$OR^x$, —O—C(=O)—$OR^x$, —$NR^y$—C(=O)—$R^x$, —C(=O)—$NR^xR^w$, or —O—C(=O)—$NR^xR^w$ is selected with preference. Here, $R^x$ and $R^w$ each represent a hydrogen atom, or an organic group having 1 to 30 carbon atoms which may have a substituent. The relevant organic group may be an organic group which is interrupted by at least one linking group selected from the group consisting of —O—, —S—, —O—C(=O)—, —C(=O)—O—, —O—C(=O)—O—, —$NR^z$—C(=O)—$NR^z$—, —$NR^z$—, and —C(=O)—, but organic groups which are interrupted by two or more contiguous —O— or —S— moieties are excluded. Meanwhile, $R^y$ and $R^z$ each represent a hydrogen atom, or an alkyl group having 1 to 6 carbon atoms.

More preferred examples of the substituent for the moiety A include a hydrogen atom, a halogen atom, an alkyl group having 1 to 20 carbon atoms, a cycloalkyl group having 1 to 20 carbon atoms, an alkenyl group having 1 to 20 carbon atoms, an aralkyl group having 1 to 20 carbon atoms, a cyano group, a nitro group, —$OR^x$, —O—C(=O)—$R^x$, and —C(=O)—$OR^x$. Here, $R^x$ represents a hydrogen atom, or an organic group having 1 to 20 carbon atoms which may have a substituent.

The substituent for the moiety A is more preferably a hydrogen atom, a halogen atom, an alkyl group having 1 to 20 carbon atoms, a cycloalkyl group having 1 to 20 carbon atoms, an aralkyl group having 1 to 20 carbon atoms, or —C(=O)—$OR^x$. Here, $R^x$ represents a hydrogen atom, or an aromatic group having 1 to 20 carbon atoms which may have a substituent.

Among them, when the moiety A in the diarylamine compound represented by the formula (III) is a phenyl group which may have a substituent, the relevant substituent is preferably linked to the phenyl through —O—C(=O)—, —C(=O)—NH—, or —C(=O)—.

Moreover, in regard to the compound represented by the formula (III), it is preferable that $X^1$ to $X^9$ in the formula (iii-2) be each independently a hydrogen atom, a halogen atom, or an alkyl halide having 1 to 3 carbon atoms.

In regard to the diarylamine compound represented by the formula (III) of the present invention, compounds that are more preferred from the viewpoint of providing an excellent effect of enhancing heat resistance include the following compounds 10 to 26. Meanwhile, some of these compounds may overlap with the diarylamine compound represented by the formula (I) or (II) of the present invention.

Compound 10

[Chemical Formula 80]

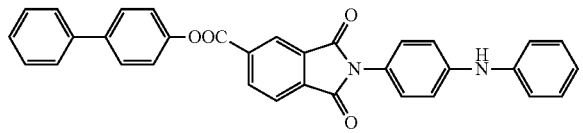

Compound 11

[Chemical Formula 81]

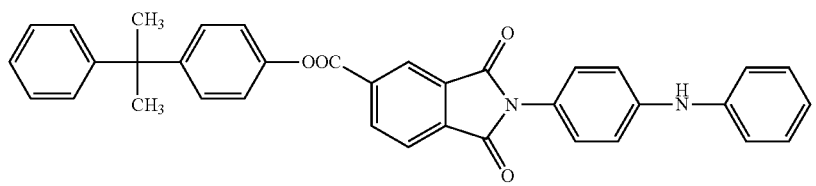

Compound 12

[Chemical Formula 82]

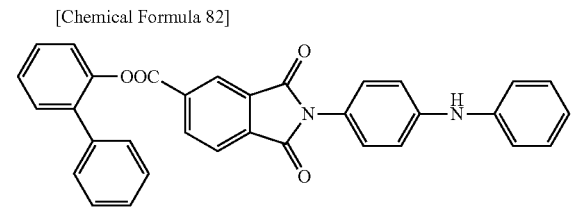

Compound 13

[Chemical Formula 83]

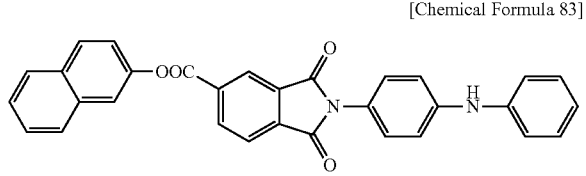

Compound 14

[Chemical Formula 84]

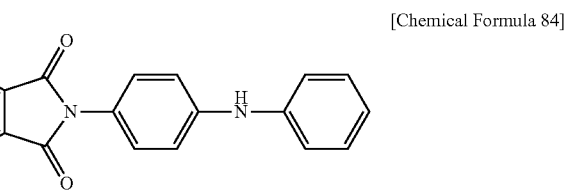

Compound 15
[Chemical Formula 85]
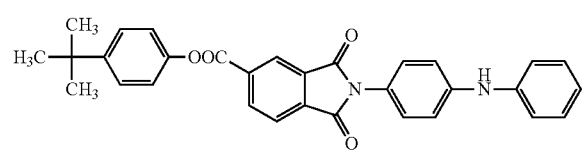
Compound 16
[Chemical Formula 86]
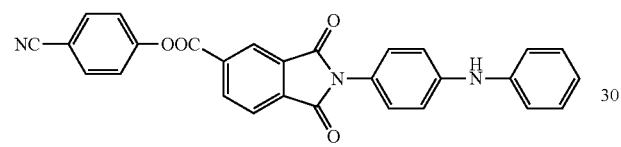
Compound 17
[Chemical Formula 87]
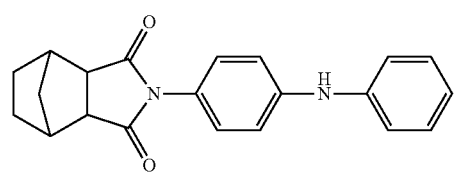
Compound 18
[Chemical Formula 88]
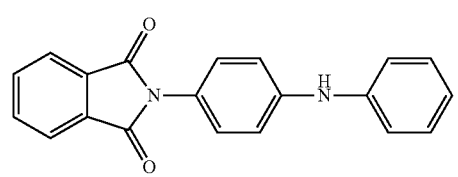
Compound 19
[Chemical Formula 89]
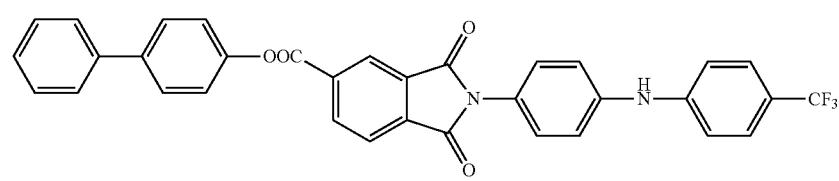
Compound 20
[Chemical Formula 90]
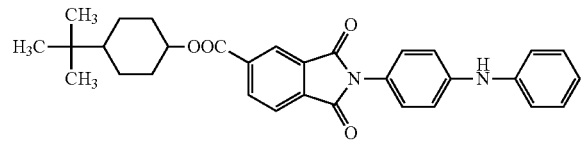
Compound 21
[Chemical Formula 91]
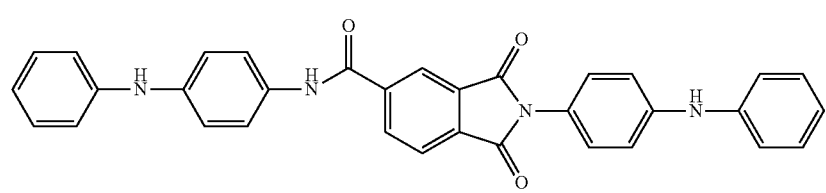
Compound 22
[Chemical Formula 92]
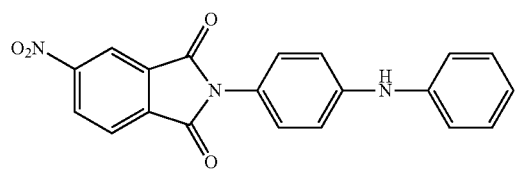
Compound 23
[Chemical Formula 93]
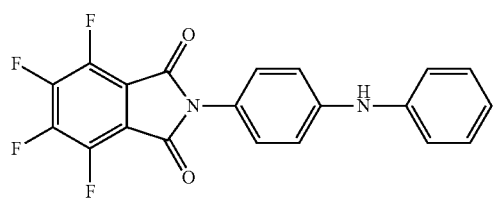

Compound 24

[Chemical Formula 94]

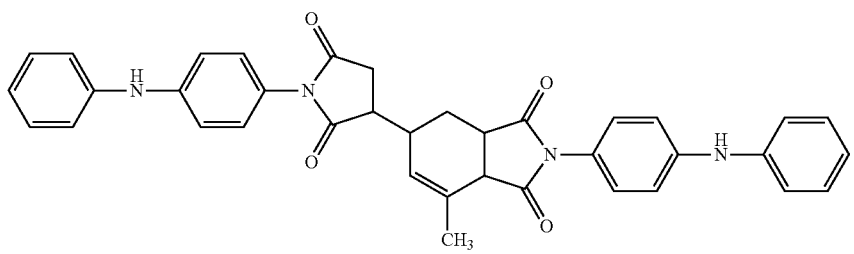

Compound 25

[Chemical Formula 95]

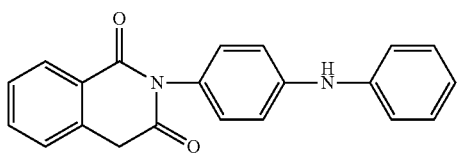

Compound 26

[Chemical Formula 96]

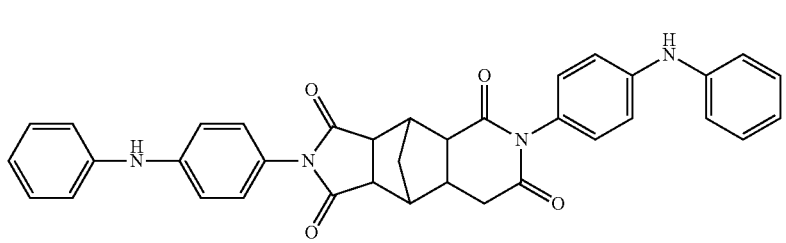

Among these, a particularly preferred compound is the following compound 10.
Compound 10

[Chemical Formula 97]

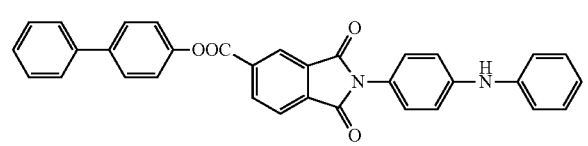

The molecular weights of these compounds that are appropriate for an aging inhibitor, and the values of the signals attributable to the hydrogen of the N—H moiety are presented in Table 1-1. Furthermore, also for the diphenylamine-based compounds that are conventionally known as aging inhibitors, the molecular weights and the values of the signals attributable to the hydrogen of the N—H moiety are presented in Table 1-2.

TABLE 1-1

| Aging inhibitor | Chemical structure | Molecular weight | N—H shift value in ¹H-NMR DMSO-d6, TMS, δ ppm) |
|---|---|---|---|
| Compound 10 | 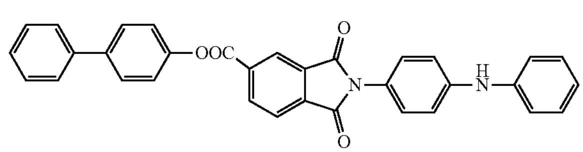 | 510.6 | 8.44 |

TABLE 1-1-continued

| Aging inhibitor | Chemical structure | Molecular weight | N—H shift value in $^1$H-NMR DMSO-d6, TMS, δ ppm) |
|---|---|---|---|
| Compound 11 | 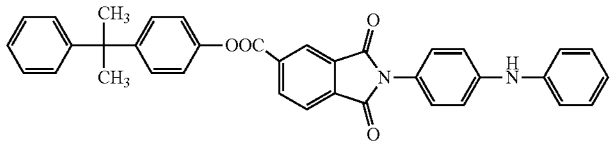 | 552.7 | 8.43 |
| Compound 12 | 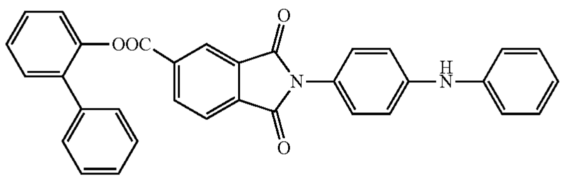 | 510.6 | 8.42 |
| Compound 13 | 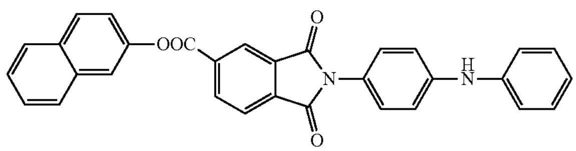 | 484.5 | 8.44 |
| Compound 14 | 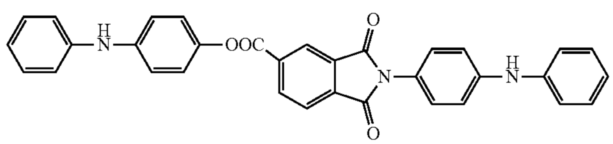 | 525.6 | 8.43/8.27 |
| Compound 15 | 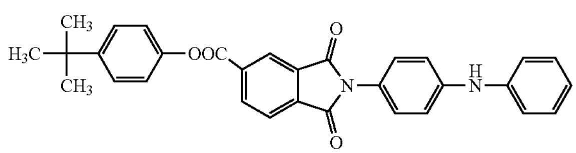 | 490.6 | 8.43 |
| Compound 16 | 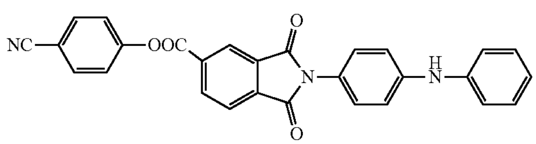 | 459.5 | 8.43 |
| Compound 17 | 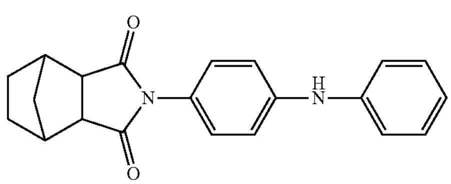 [SMILES: O=C1C2C3CCC(C3)C2C(=O)N1c1ccc(Nc2ccccc2)cc1] | 332.4 | 8.38 |
| Compound 18 | 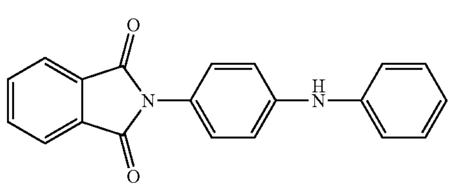 [SMILES: O=C1c2ccccc2C(=O)N1c1ccc(Nc2ccccc2)cc1] | 314.4 | 8.40 |
| Compound 19 | 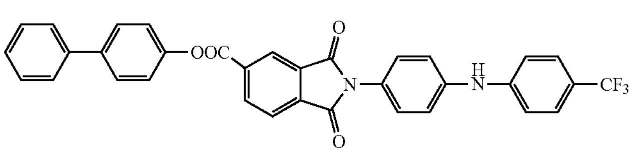 | 578.6 | 8.94 |

TABLE 1-1-continued

| Aging inhibitor | Chemical structure | Molecular weight | N—H shift value in $^1$H-NMR DMSO-d6, TMS, δ ppm) |
|---|---|---|---|
| Compound 20 | 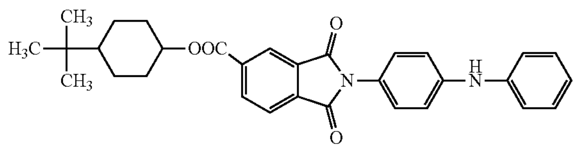 | 496.7 | 8.43 |
| Compound 21 | 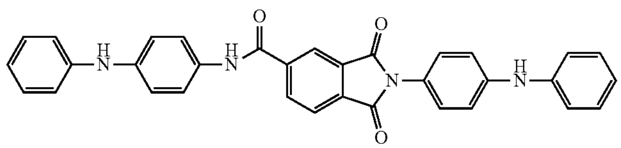 [SMILES: O=C(Nc1ccc(Nc2ccccc2)cc1)c1ccc2c(c1)C(=O)N(c1ccc(Nc3ccccc3)cc1)C2=O] | 524.6 | 8.43/8.16 |
| Compound 22 | 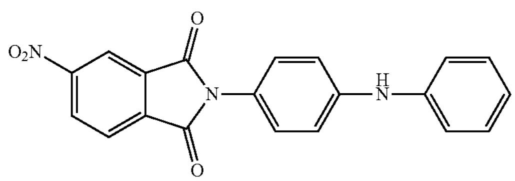 [SMILES: O=C1c2ccc([N+](=O)[O-])cc2C(=O)N1c1ccc(Nc2ccccc2)cc1] | 359.4 | 8.44 |
| Compound 23 | 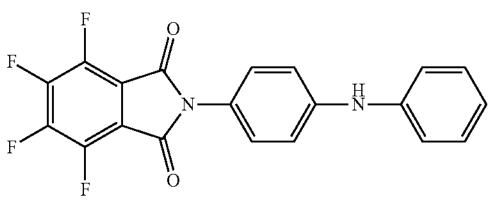 [SMILES: O=C1c2c(F)c(F)c(F)c(F)c2C(=O)N1c1ccc(Nc2ccccc2)cc1] | 386.3 | 8.45 |
| Compound 24 | 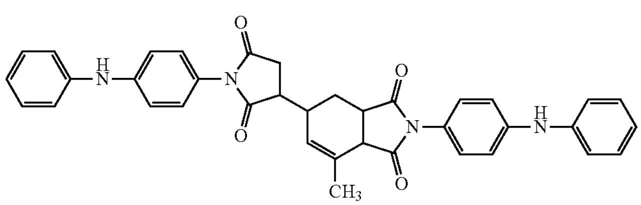 [SMILES: CC1=CC(C2CC(=O)N(c3ccc(Nc4ccccc4)cc3)C2=O)CC2C(=O)N(c3ccc(Nc4ccccc4)cc3)C(=O)C12] | 596.7 | 8.36/8.35 |
| Compound 25 | 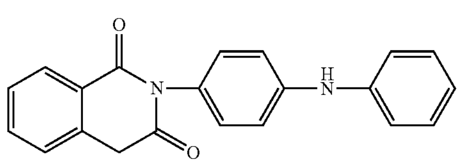 [SMILES: O=C1Cc2ccccc2C(=O)N1c1ccc(Nc2ccccc2)cc1] | 328.4 | 8.31 |

TABLE 1-2

Conventional diphenylamine-based compounds

| Aging inhibitor | Chemical Structure | Molecular weight | N—H shift value in $^1$H-NMR (DMSO-d6, TMS, δ ppm) |
|---|---|---|---|
| Diphenylamine | 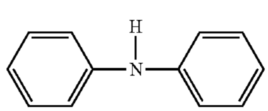 [SMILES: c1ccc(Nc2ccccc2)cc1] | 169.2 | 8.14 |

TABLE 1-2-continued

Conventional diphenylamine-based compounds

| Aging inhibitor | Chemical Structure | Molecular weight | N—H shift value in ¹H-NMR (DMSO-d6, TMS, δ ppm) |
|---|---|---|---|
| STEARER-STAR (manufactured by Seiko Chemical Co., Ltd.) | [structure] | 281.5 | 7.90 |
| NONFLEX LAS-P (manufactured by Seiko Chemical Co., Ltd.) | [structure] 28.6%:71.4% mixture | 303.2 (Average molecular weight) | 7.85/8.04 |
| NOCRAC WHITE (manufactured by Ouchi Shinko Chemical Industrial Co., Ltd.) | [structure] | 360.5 | 8.23 |
| NOCRAC DP (manufactured by Ouchi Shinko Chemical Industrial Co., Ltd.) | [structure] | 260.4 | 7.88 |
| NOCRAC AD-F (manufactured by Ouchi Shinko Chemical Industrial Co., Ltd.) | [structure] | 393.7 | 7.87 |
| NAUGARD 445 (manufactured by Shiraishi Calcium Kaisha, Ltd.) | [structure] | 405.6 | 7.97 |

7. Method of Producing Diarylamine Compound Represented by Formula (III)

The method of the present invention for producing a diarylamine compound represented by the formula (III), which has at least one signal attributable to the hydrogen of the N—H moiety at 8.30 ppm to 9.00 ppm when a deuterated dimethyl sulfoxide solution of the diarylamine compound is analyzed by ¹H-NMR, is not particularly limited. However, for example, the target compound can be easily produced by dissolving 4-aminodiphenylamine which may have a substituent and a dicarboxylic acid anhydride in acetic acid, and subjecting the solution to a reaction of allowing the compounds to react while heating the compounds to reflux, and thereby forming an imide ring.

8. Aging Inhibitor

The novel diarylamine compound of the present invention can be used as an aging inhibitor for organic materials such as polymers. The diarylamine compound of the present invention is a compound which is used with preference as an aging inhibitor for polymers. There are no particular limitations on the polymer materials that are applicable, and the diarylamine compound can be applied to those polymer materials that have been used for the applications where heat resistance is required, such as rubbers, polyolefins, polystyrene-based resins, polyesters, polycarbonates, and polyamides. Among them, rubbers and polyolefins, for which there has been in recent years a demand for higher heat resistance than ever before, are suitably usable.

When the compound of the present invention is used as an aging inhibitor for polymers, the method of mixing the compound of the present invention into a polymer is not particularly limited, and the compound may be incorporated by adding the compound into a polymer latex or into a polymer solution and then coagulating the latex or the solution, or the compound may be incorporated at any stage in the course of production step of final products. Specifically, the incorporation may be carried out at the stage of polymer pellet production, at the stage of kneading, or at the stage of feeding into a molding machine. In short, the time for incorporation may be selected so that the compound of the present invention can be sufficiently uniformly dispersed in the polymer.

When the compound of the present invention is used as an aging inhibitor for polymers, the incorporation amount of the compound of the present invention may be 0.5 to 100 mmol, preferably 1 to 50 mmol, and particularly preferably 2 to 30 mmol, relative to 100 g of the polymer. If the incorporation amount of the compound of the present invention is less than 0.5 mmol, the effect as an aging inhibitor is not exhibited. If the incorporation amount is greater than 100 mmol, an enhancement of the effect as an aging inhibitor cannot be obtained, and on the other hand, there is a possibility that bleed-out or discoloration of molded articles may occur, which is not preferable. Furthermore, the compound of the present invention may be used singly, or two or more kinds may be used in combination. Furthermore, the compound of the present invention can be used in combination with conventionally used aging inhibitors to the extent that the effects of the invention are not impaired.

9. Polyolefin

The diarylamine compound of the present invention, particularly the diarylamine compound represented by formula (I) or formula (II), is such that when the compound is incorporated into a polyolefin as an aging inhibitor, the compound can enable the polyolefin at a higher temperature than in conventional cases.

The polyolefin may be a polyolefin that is used in the field where heat resistance is required, and is selected from polyethylene, polypropylene, polybutene, and cycloolefin polymers. Particularly, when a cycloolefin polymer that is known as a heat resistant material and is used in the fields of surface mounted components for semiconductors and the like, automobile parts, and members for construction use, is applied, the aging inhibitor can be used in a higher temperature environment than in conventional cases.

Among them, a cycloolefin polymer has a ring structure formed from carbon atoms in the molecule, and is obtained by polymerizing a cycloolefin monomer having a carbon-carbon double bond in the ring. Thus, the aging inhibitor according to the present invention can be used with preference.

Examples of the cycloolefin monomer include monocyclic cycloolefin monomers and norbornene-based monomers, and a norbornene-based monomer is preferred. The norbornene-based monomer is a cycloolefin monomer having a norbornene ring structure in the molecule. This may be substituted with a hydrocarbon group such as an alkyl group, an alkenyl group, an alkylidene group, or an aryl group, or with a polar group. Furthermore, the norbornene-based monomer may also have a double bond in addition to the double bond of the norbornene ring.

Examples of the monocyclic cycloolefin monomers include cyclobutene, cyclopentene, cyclooctene, cyclododecene, and 1,5-cyclooctadiene.

Specific examples of the norbornene-based monomers include dicyclopentadienes such as dicyclopentadiene and methyldicyclopentadiene; tetracyclododecenes such as tetracyclo[$6.2.1.1^{3,6}.0^{2,7}$]dodec-4-ene, 9-ethylidenetetracyclo[$6.2.1.1^{3,6}.0^{2,7}$]dodec-4-ene, 9-phenyltetracyclo[$6.2.1.1^{3,6}.0^{2,7}$]dodec-4-ene, tetracyclo[$6.2.1.1^{3,6}.0^{2,7}$]dodec-9-ene-4-carboxylic acid, and tetracyclo[$6.2.1.1^{3,6}.0^{2,7}$]dodec-9-ene-4,5-dicarboxylic acid anhydride; norbornenes such as 2-norbornene, 5-ethylidene-2-norbornene, 5-vinyl-2-norbornene, 5-phenyl-2-norbornene, 5-norbornen-2-yl acrylate, 5-norbornen-2-yl methacrylate, 5-norbornene-2-carboxylic acid, 5-norbornene-2,3-dicarboxylic acid, and 5-norbornene-2,3-dicarboxylic acid anhydride; oxanorbornenes such as 7-oxa-2-norbornene, and 5-ethylidene-7-oxa-2-norbornene; and tetracyclic or higher-cyclic cycloolefins such as tetracyclo[$9.2.1.0^{2,10}.0^{3,8}$]tetradeca-3,5,7,12-tetraene (also called 1,4-methano-1,4,4a,9a-tetrahydro-9H-fluorene), pentacyclo[$6.5.1.13,6.0^{2,7}.0^{9,13}$]pentadeca-4,10-diene, and pentacyclo[$9.2.1.0^{2,10}.0^{3,8}$]pentadeca-5,12-diene.

The method of polymerizing a cycloolefin polymer may be bulk polymerization or solution polymerization; however, it is preferable to subject a cycloolefin monomer to bulk ring-opening polymerization using a metathesis catalyst.

10. Rubber

There are no particular limitations on the rubber to which the diarylamine compound of the present invention can be applied, but examples include natural rubber; rubbers containing conjugated diene units, such as isoprene rubber, butadiene rubber, butyl rubber, chloroprene rubber, styrene-butadiene copolymer rubber, acrylonitrile-butadiene copolymer rubber (nitrile rubber), styrene-butadiene-isoprene copolymer rubber, butadiene-isoprene copolymer rubber, and acrylonitrile-styrene-butadiene copolymer rubber; an acrylic rubber; a hydrine rubber, and an ethylene-propylene rubber. These rubbers may have a hydroxyl group, a carboxyl group, an alkoxysilyl group, an amino group, an epoxy group, and the like. Furthermore, these rubbers may be hydrogenated, and for example, hydrogenation products of acrylonitrile-butadiene copolymer rubber (hydrogenated nitrile rubbers) may be mentioned. These rubbers may be used singly, or two or more kinds may be used in combination. Among these, it is particularly preferable to apply the present invention to acrylic rubber or hydrogenated nitrile rubber, which are both required to have high heat resistance, from the viewpoint of the effect of improving heat resistance.

(Acrylic Rubber)

The acrylic rubber that is used in the present invention has 50% to 100% by weight of a (meth)acrylic acid ester monomer unit, 10% to 0% by weight of a crosslinkable monomer unit, and optionally, 50% to 0% by weight of another monomer unit which is copolymerizable with the monomers which form these monomer units. Meanwhile, (meth)acrylic acid as used in the present invention indicates acrylic acid and methacrylic acid (hereinafter, the same).

There are no particular limitations on the (meth)acrylic acid ester monomer that forms the (meth)acrylic acid ester monomer unit, which is a main component of the acrylic rubber; however, preferred examples include a (meth)acrylic acid alkyl ester monomer, and a (meth)acrylic acid alkoxyalkyl ester monomer.

There are no particular limitations on the (meth)acrylic acid alkyl ester monomer; however, esters of alkanols having 1 to 8 carbon atoms and (meth)acrylic acid are preferred, and specific examples include methyl (meth)acrylate, ethyl (meth)acrylate, n-propyl (meth)acrylate, n-butyl (meth)acrylate, isopropyl (meth)acrylate, isobutyl (meth)acrylate, n-hexyl (meth)acrylate, 2-ethylhexyl (meth)acrylate, and cyclohexyl (meth)acrylate. Among these, ethyl (meth)acrylate, and n-butyl (meth)acrylate are preferred, and ethyl acrylate and n-butyl acrylate are particularly preferred. These can be used singly, or two or more kinds can be used in combination.

There are no particular limitations on the (meth)acrylic acid alkoxyalkyl ester monomer; however, esters of alkoxyalkyl alcohols having 2 to 8 carbon atoms and (meth)acrylic acid are preferred, and specific examples include methoxymethyl (meth)acrylate, ethoxymethyl (meth)acrylate, 2-methoxyethyl (meth)acrylate, 2-ethoxyethyl (meth)acrylate, 2-propoxyethyl (meth)acrylate, 2-butoxyethyl (meth)acrylate, 3-methoxypropyl (meth)acrylate, and 4-methoxybutyl (meth)acrylate. Among these, 2-ethoxyethyl (meth)acrylate and 2-methoxyethyl (meth)acrylate are preferred, and 2-ethoxyethyl acrylate and 2-methoxyethyl acrylate are particularly preferred. These can be used singly, or two or more kinds can be used in combination.

The content of the (meth)acrylic acid ester monomer unit in the acrylic rubber is preferably 50% to 100% by weight, more preferably 60% to 95% by weight, and even more preferably 70% to 95% by weight. If the content of the (meth) acrylic acid ester monomer unit is too small, there is a risk that the weather resistance, heat resistance and oil resistance of the crosslinked rubber product may be decreased.

The contents of the (meth)acrylic acid ester monomer units are preferably 30% to 100% by weight of the (meth)acrylic acid alkyl ester monomer unit, and 70% to 0% by weight of the (meth)acrylic acid alkoxyalkyl ester monomer unit.

There are no particular limitations on the crosslinkable monomer that forms a crosslinkable monomer unit, but examples include an $\alpha,\beta$-ethylenically unsaturated carboxylic acid monomer; a monomer having a halogen atom; a monomer having an epoxy group; and a diene monomer. There are no particular limitations on the $\alpha,\beta$-ethylnically unsaturated carboxylic acid monomer, but examples include an $\alpha,\beta$-ethylnically unsaturated monocarboxylic acid having 3 to 12 carbon atoms, an $\alpha,\beta$-ethylenically unsaturated dicarboxylic acid having 4 to 12 carbon atoms, and a monoester of an $\alpha,\beta$-ethylenically unsaturated dicarboxylic acid having 3 to 11 carbon atoms and an alkanol having 1 to 8 carbon atoms.

Examples of the $\alpha,\beta$-ethylenically unsaturated monocarboxylic acid having 3 to 12 carbon atoms include acrylic acid, methacrylic acid, $\alpha$-ethylacrylic acid, crotonic acid, and cinnamic acid. Examples of the $\alpha,\beta$-ethylenically unsaturated dicarboxylic acid having 4 to 12 carbon atoms include a butenedioic acid such as fumaric acid or maleic acid, itaconic acid, citraconic acid, and chloromaleic acid. Examples of the monoester of an $\alpha,\beta$-ethylenically unsaturated dicarboxylic acid having 3 to 11 carbon atoms and an alkanol having 1 to 8 carbon atoms include butenedioic acid mono-linear alkyl esters such as monomethyl fumarate, monoethyl fumarate, monobutyl fumarate, monomethyl maleate, monoethyl maleate, and monobutyl maleate; butenedioic acid monoesters having an alicyclic structure, such as monocyclopentyl fumarate, monocyclohexyl fumarate, monocyclohexenyl fumarate, monocyclopentyl maleate, monocyclohexyl maleate, and monocyclohexenyl maleate; itaconic acid monoesters such as monomethyl itaconate, monoethyl itaconate, monobutyl itaconate, and monocyclohexyl itaconate; and mono-2-hydroxyethyl fumarate.

Among these, butenedioic acid mono-linear alkyl esters, or butenedioic acid monoesters having an alicyclic structure are preferred, and monobutyl fumarate, monobutyl maleate, monocyclohexyl fumarate, and monocyclohexyl maleate are more preferred.

These $\alpha,\beta$-ethylenically unsaturated carboxylic acid monomers can be used singly, or in combination of two or more kinds. Among the monomers described above, dicarboxylic acids are intended to include compounds that are in the form of anhydride.

There are no particular limitations on the monomer having a halogen atom, but examples include an unsaturated alcohol ester of a halogen-containing saturated carboxylic acid, a (meth)acrylic acid haloalkyl ester, a (meth)acrylic acid haloacyloxyalkyl ester, a (meth)acrylic acid (haloacetylcarbamoyloxy)alkyl ester, a halogen-containing unsaturated ether, a halogen-containing unsaturated ketone, a halomethyl group-containing aromatic vinyl compound, and a haloacetyl group-containing unsaturated monomer.

Examples of the unsaturated alcohol ester of a halogen-containing saturated carboxylic acid include vinyl chloroacetate, vinyl 2-chloropropionate, and allyl chloroacetate.

Examples of the (meth)acrylic acid haloalkyl ester include chloromethyl (meth)acrylate, 1-chloroethyl (meth)acrylate, 2-chloroethyl (meth)acrylate, 1,2-dichloroethyl (meth)acrylate, 2-chloropropyl (meth)acrylate, 3-chloropropyl (meth)acrylate, and 2,3-dichloropropyl (meth)acrylate.

Examples of the (meth)acrylic acid haloacyloxyalkyl ester include 2-(chloroacetoxy)ethyl (meth)acrylate, 2-(chloroacetoxy)propyl (meth)acrylate, 3-(chloroacetoxy)propyl (meth)acrylate, 3-(hydroxychloroacetoxy)propyl (meth) acrylate.

Examples of the (meth)acrylic acid (haloacetylcarbamoyloxy)alkyl ester include 2-(chloroacetylcarbamoyloxy)ethyl (meth)acrylate, and 3-(chloroacetylcarbamoyloxy)propyl (meth)acrylate.

Examples of the halogen-containing unsaturated ether include chloromethyl vinyl ether, 2-chloroethyl vinyl ether, 3-chloropropyl vinyl ether, 2-chloroethyl allyl ether, and 3-chloropropyl allyl ether.

Examples of the halogen-containing unsaturated ketone include 2-chloroethyl vinyl ketone, 3-chloropropyl vinyl ketone, and 2-chloroethyl allyl ketone.

Examples of the halomethyl group-containing aromatic vinyl compound include p-chloromethylstyrene, m-chloromethylstyrene, o-chloromethylstyrene, p-chloromethyl-$\alpha$-methylstyrene, and p-bis(chloromethyl)styrene.

Examples of a halogen-containing unsaturated amide include N-chloromethyl(meth)acrylamide.

Examples of the haloacetyl group-containing unsaturated monomer include 3-(hydroxychloroacetoxy)propyl allyl ether, and p-vinylbenzyl chloroacetic acid ester.

There are no particular limitations on the monomer having an epoxy group, but examples include an epoxy group-containing (meth)acrylic acid ester, and an epoxy group-containing ether.

Examples of the epoxy group-containing (meth)acrylic acid ester include glycidyl (meth)acrylate. Examples of the epoxy group-containing ether include allyl glycidyl ether.

Examples of the diene monomer include a conjugated diene monomer and a non-conjugated diene monomer.

Examples of the conjugated diene monomer include 1,3-butadiene, isoprene, and piperylene. Examples of the non-conjugated diene monomer include ethylidene norbornene, dicyclopentadiene, dicyclopentadienyl (meth)acrylate, and 2-dicyclopentadienylethyl (meth)acrylate.

These crosslinkable monomers can be used singly, or two or more kinds can be used in combination. The amount of a crosslinkable monomer unit derived from such a crosslinkable monomer in the acrylic rubber is preferably 0% to 10% by weight, more preferably 0.5% to 7% by weight, and even more preferably 1% to 5% by weight. If the amount of such a crosslinkable monomer unit is excessively large, there is a possibility that the elongation of the crosslinked rubber product may decrease, or the compression set may increase. On the contrary, if the amount is too small, there is a risk that crosslinking occurs insufficiently, satisfactory mechanical properties may not be obtained, or the surface texture of the molded article may lack smoothness.

Furthermore, there are no particular limitations on the other monomer that constitutes the other monomer unit described above, but examples include an aromatic vinyl monomer, an α,β-ethylenically unsaturated nitrile monomer, a monomer having two or more acryloyloxy groups (hereinafter, may be referred to as a "polyfunctional acrylic monomer"), an olefin-based monomer, and a vinyl ether compound.

Examples of the aromatic vinyl monomer include styrene, α-methylstyrene, and divinylbenzene. Examples of the α,β-ethylenically unsaturated nitrile monomer include acrylonitrile, and methacrylonitrile. Examples of the polyfunctional acrylic monomer include ethylene glycol di(meth)acrylate, and propylene glycol di(meth)acrylate. Examples of the olefin-based monomer include ethylene, propylene, 1-butene, and 1-octene. Examples of the vinyl ether compound include vinyl acetate, ethyl vinyl ether, and butyl vinyl ether. Among these, styrene, acrylonitrile, and methacrylonitrile are preferred, and acrylonitrile and methacrylonitrile are more preferred.

The other monomers can be used singly, or two or more kinds can be used in combination. The amount of the other monomer unit in the acrylic rubber is preferably 0% to 50% by weight, more preferably 0% to 40% by weight, and even more preferably 0% to 30% by weight.

The acrylic rubber used in the present invention can be obtained by polymerizing monomers (mixture) which include the various monomers described above. In regard to the mode of polymerization reaction, all of an emulsion polymerization method, a suspension polymerization method, a bulk polymerization method, and a solution polymerization method can be used. However, in view of the ease of control of the polymerization reaction or the like, it is preferable to use an emulsion polymerization method under normal pressure, which is generally used as a conventionally known production method for an acrylic rubber.

Emulsion polymerization may be carried out in any of a batch mode, a semi-batch mode, and a continuous mode. The polymerization process is carried out at a temperature in the range of usually 0° C. to 70° C., and preferably 5° C. to 50° C.

The acrylic rubber used in the present invention, which is produced in this manner, has a Mooney viscosity ($ML_{1+4}$, 100° C.) (polymer Mooney) of preferably 10 to 80, more preferably 20 to 70, and particularly preferably 25 to 60.

(Hydrogenated Nitrile Rubber)

The hydrogenated nitrile rubber that can be used in the present invention is a hydrogenation (hydrogen addition reaction) product of a nitrile rubber having an α,β-ethylenically unsaturated nitrile monomer unit, a conjugated diene monomer unit, and as an optionally added monomer unit, a monomer unit derived from another monomer which is copolymerizable with the monomers that form the monomer units described above. Since hydrogenated nitrile rubber is a product obtained by hydrogenating at least a portion of the carbon-carbon unsaturated bonds carried by the conjugated diene monomer, the hydrogenated nitrile rubber is known as a rubber having excellent heat resistance, sour gasoline resistance and ozone resistance, and is known to be a material which is highly functional at high temperatures in applications including seals, hoses, and packing.

There are no particular limitations on the α,β-ethylenically unsaturated nitrile monomer that forms the α,β-ethylenically unsaturated nitrile monomer unit, but examples include acrylonitrile, methacrylonitrile, and α-chloroacrylonitrile. Among them, acrylonitrile is preferred. These compounds may be used singly, but plural kinds may also be used in combination. The content of the α,β-ethylenically unsaturated nitrile monomer unit in the hydrogenated nitrile rubber is preferably 10% to 60% by weight, more preferably 12% to 55% by weight, and even more preferably 15% to 50% by weight. Properties such as oil resistance, cold resistance, heat resistance, sour gasoline resistance, and ozone resistance may vary with the content of the α,β-ethylenically unsaturated nitrile monomer unit, so that the content can be selected from a wide range of properties depending on the use.

There are no particular limitations on the conjugated diene monomer that forms the conjugated diene monomer unit, but examples include 1,3-butadiene, isoprene, 2,3-dimethyl-1,3-butadiene, and 1,3-pentadiene. Among them, 1,3-butadiene is preferred. The content of the conjugated diene monomer unit (also including hydrogenated monomer units) in the hydrogenated nitrile rubber is preferably 40% to 90% by weight, more preferably 45% to 88% by weight, and even more preferably 50% to 85% by weight.

Furthermore, there are no particular limitations on the other monomer described above, but examples include a diene monomer other than conjugated diene monomers, an α-olefin, an α,β-ethylenically unsaturated carboxylic acid ester, an aromatic vinyl monomer, a fluorine-containing vinyl monomer, an α,β-ethylenically unsaturated monocarboxylic acid, an α,β-ethylenically unsaturated dicarboxylic acid, an α,β-ethylenically unsaturated dicarboxylic acid anhydride, and a copolymerizable aging inhibitor. These other copolymerizable monomers may be used singly, or plural kinds may be used in combination.

Examples of the diene monomer other than conjugated diene monomers include 1,4-pentadiene, 1,4-hexadiene, vinylnorbornene, and dicyclopentadiene.

Examples of the α-olefin include ethylene, propylene, 1-butene, 4-methyl-1-pentene, 1-hexene, and 1-octene.

There are no particular limitations on the α,β-ethylenically unsaturated carboxylic acid ester, but examples include acrylates or methacrylates, such as methyl acrylate, ethyl acrylate, n-butyl acrylate, 2-ethylhexyl acrylate, n-dodecyl acrylate, methyl methacrylate, and ethyl methacrylate; alkoxyalkyl acrylates or alkoxyalkyl methacrylates, such as methoxymethyl acrylate, and 2-methoxyethyl methacrylate; cyanoalkyl acrylates or cyanoalkyl methacrylates, such as α-cyanoethyl acrylate, β-cyanoethyl acrylate, and cyanobutyl methacrylate; hydroxyalkyl acrylates such as 2-hydroxyethyl acrylate, and 3-hydroxypropyl acrylate; α,β-ethylenically unsaturated dicarboxylic acid monoalkyl esters or α,β-ethylenically unsaturated dicarboxylic acid dialkyl esters, such as monoethyl maleate, dimethyl maleate, dimethyl fumarate, dimethyl itaconate, diethyl itaconate, and di-n-butyl itaconate; amino group-containing α,β-ethylenically unsaturated carboxylic acid ester-based monomers, such as dimethylaminomethyl acrylate, and diethylaminoethyl acrylate; acrylates or methacrylates having a fluoroalkyl group, such as trifluoroethyl acrylate, and tetrafluoropropyl methacrylate; and fluorine-substituted benzyl acrylates or fluorine-substituted benzyl methacrylates, such as fluorobenzyl acrylate, and fluorobenzyl methacrylate.

There are no particular limitations on the aromatic vinyl monomer, but examples include styrene, α-methylstyrene, and vinylpyridine. There are no particular limitations on the fluorine-containing vinyl-based monomer, but examples include fluoroethyl vinyl ether, fluoropropyl vinyl ether, o-(trifluoro)methylstyrene, vinyl pentafluorobenzoate, difluoroethylene, and tetrafluoroethylene.

There are no particular limitations on the α,β-ethylenically unsaturated monocarboxylic acid, but examples include acrylic acid, and methacrylic acid. There are no particular limitations on the α,β-ethylenically unsaturated dicarboxylic acid, but examples include itaconic acid, fumaric acid, and maleic acid. There are no particular limitations on the α,β-ethylenically unsaturated dicarboxylic acid anhydride, but examples include maleic anhydride. Among them, acrylic acid or methacrylic acid is preferred.

There are no particular limitations on the copolymerizable aging inhibitors, but examples include N-(4-anilinophenyl)acrylamide, N-(4-anilinophenyl)methacrylamide, N-(4-anilinophenyl)cinnamide, N-(4-anilinophenyl)crotonamide, N-phenyl-4-(3-vinylbenzyloxy)aniline, and N-phenyl-4-(4-vinylbenzyloxy)aniline.

The content of the monomer unit derived from the other monomers in the hydrogenated nitrile rubber is preferably 0% to 30% by weight, more preferably 0% to 10% by weight, and even more preferably 0% to 5% by weight.

The method of producing the nitrile rubber is not particularly limited. Generally, a method of copolymerizing an α,β-ethylenically unsaturated nitrile monomer, a conjugated diene monomer, and another monomer which is optionally added and is copolymerizable with the foregoing monomers, is convenient and preferable. As the polymerization method, any of known emulsion polymerization methods, suspension polymerization methods, bulk polymerization methods and solution polymerization methods can be used; however, from the viewpoint of the ease of control of the polymerization reaction, an emulsion polymerization method is preferred.

When the nitrile rubber thus produced is hydrogenated to obtain a hydrogenated nitrile rubber, heat resistance, sour gasoline resistance and ozone resistance are further enhanced. The method of performing hydrogenation (hydrogen addition reaction) is not particularly limited, and any known method may be employed. There are no particular limitations on the iodine value of the hydrogenated nitrile-based rubber (measured according to JIS K6235), and the iodine value is preferably 120 or less, more preferably 60 or less, and even more preferably 30 or less. If the iodine value is too high, heat resistance is poor. The Mooney viscosity [$ML_{1+4}$ (100° C.)] (polymer Mooney) of the hydrogenated nitrile rubber is preferably 15 to 200, more preferably 30 to 150, and particularly preferably 45 to 120. If the Mooney viscosity of the hydrogenated nitrile rubber is too low, there is a risk that the mechanical characteristics of the crosslinked rubber product may deteriorate. On the contrary, if the Mooney viscosity is too high, there is a possibility that processability may deteriorate.

11. Polymer Composition and Rubber Composition

The polymer composition of the present invention is a polymer composition containing the diarylamine compound represented by any one of the formulas (I) to (III), and a polymer. According to the present invention, a polymer composition in which the polymer is a rubber, that is, a rubber composition is provided. Particularly, a rubber composition in which the rubber is an acrylic rubber or a hydrogenated nitrile rubber is provided. The rubber composition of the present invention contains a rubber, particularly the acrylic rubber or hydrogenated nitrile rubber described above, as well as a compound represented by one of the formulas (I) to (III), and a crosslinking agent.

The rubber composition of the present invention will be described by taking an example of a rubber composition in which the rubber is an acrylic rubber, that is, an acrylic rubber composition; however, the same explanation can also be given for a hydrogenated nitrile rubber. The rubber composition contains, as an aging inhibitor, a compound represented by any one of the formulas (I) to (III) of the present invention in an amount of 0.1 to 50 parts by weight, preferably 0.3 to 25 parts by weight, and particularly preferably 0.5 to 15 parts by weight, relative to 100 parts by weight of the acrylic rubber. Furthermore, on a molar basis, the rubber composition contains, as an aging inhibitor, the compound represented by any one of the formulas (I) to (III) of the present invention in an amount of 0.5 to 100 mmol, preferably 1 to 50 mmol, and particularly preferably 2 to 30 mmol, relative to 100 g of the acrylic rubber. If the content of the compound represented by any one of the formulas (I) to (III) of the present invention is less than the range described above, an effect as an aging inhibitor is not obtained. On the other hand, if the content is larger than the range described above, there is a possibility of the occurrence of bleed-out or discoloration of molded articles, which is not preferable. The compounds represented by the formulas (I) to (III) of the present invention may be used singly, or two or more kinds may be used in combination. Furthermore, the compounds can be used in combination with a conventionally used aging inhibitor, to an extent that the effect of the present invention is not impaired.

There are no particular limitations on the method of incorporating, into the acrylic rubber, the compound of the present invention represented by any one of the formulas (I) to (III) of the present invention, which has at least one signal attributable to the hydrogen of the N—H moiety at 8.30 ppm to 9.00 ppm when a deuterated dimethyl sulfoxide solution of the compound is analyzed by $^1$H-NMR. For example, the compound may be incorporated by adding the compound into a polymer latex or a polymer solution, and then coagulating the latex or solution, or the compound may be incorporated at any stage in the course of production step of final products. Specifically, the incorporation may be carried out at the stage of polymer pellet production, at the stage of kneading, or at the stage of feeding into a molding machine. In short, the time for incorporation may be selected so that the compound of the present invention can sufficiently uniformly be dispersed in the polymer.

The acrylic rubber composition of the present invention contains a crosslinking agent in an amount of preferably 0.05 to 20 parts by weight, more preferably 0.1 to 15 parts by weight, and particularly preferably 0.3 to 12 parts by weight, relative to 100 parts by weight of the acrylic rubber. If the content of the crosslinking agent is too small, crosslinking is not sufficiently achieved, and therefore, shape retention of the crosslinked rubber product thus obtained is difficult. If the content is too large, the crosslinked rubber product thus obtained may become excessively hard.

A particularly preferred composition is an acrylic rubber composition containing 100 parts by weight of an acrylic rubber, 0.1 to 50 parts by weight of a compound represented by the following formula (XII), which belongs to the compound represented by the formula (I) of the present invention:

[Chemical Formula 98]

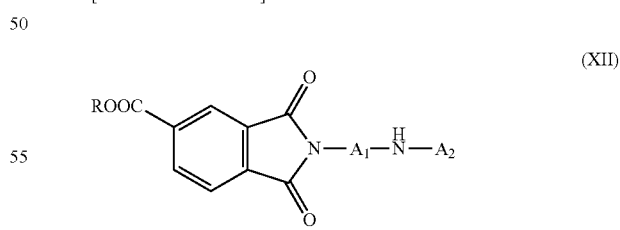

(XII)

wherein in the formula (XII), $A_1$ and $A_2$ each independently represent an aromatic group which may have a substituent having 1 to 30 carbon atoms; and R represents an organic group having 1 to 30 carbon atoms which may have a substituent, or a compound represented by the following formula (XIII), which, likewise, belongs to the compound represented by the formula (II) of the present invention:

[Chemical formula 99]

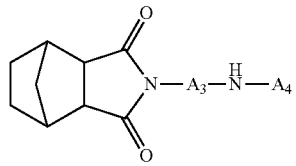

(XIII)

wherein in the formula (XIII), $A_3$ and $A_4$ each independently represent an aromatic group which may have a substituent having 1 to 30 carbon atoms, and 0.05 to 20 parts by weight of a crosslinking agent.

The acrylic rubber composition may contain additives that are conventionally used in the rubber processing field, in addition to the acrylic rubber, the aging inhibitor and the crosslinking agent. Examples of such additives include a reinforcing filler such as carbon black or silica; a non-reinforcing filler material such as calcium carbonate or clay; a light stabilizer, an anti-scorching agent, a plasticizer, a processing aid, a lubricating agent, a tacky adhesive, a lubricant, a flame retardant, an antimicrobial agent, an antistatic agent, a colorant, a silane coupling agent, a crosslinking accelerating agent, and a crosslinking delaying agent. The incorporation amount of these additives is not particularly limited as long as the incorporation amount is limited to the extent that it does not impair the purpose or effect of the present invention, and the additives can be appropriately incorporated in an amount selected in accordance with the purpose of incorporation.

The acrylic rubber composition may further contain a rubber other than the acrylic rubber used in the present invention, an elastomer, a resin or the like, to the extent that the effect of the present invention is not impaired. For example, rubbers such as natural rubber, a polybutadiene rubber, a polyisoprene rubber, a styrene-butadiene rubber, an acrylonitrile-butadiene rubber, a silicone rubber, and a fluororubber; elastomers such as an olefin-based elastomer, a styrene-based elastomer, a vinyl chloride-based elastomer, a polyester-based elastomer, a polyamide-based elastomer, a polyurethane-based elastomer, and a polysiloxane-based elastomer; and resins such as a polyolefin-based resin, a polystyrene-based resin, a polyacrylic-based resin, a polyphenylene ether-based resin, a polyester-based resin, a polycarbonate-based resin, a polyamide resin, and a fluororesin, can be incorporated. In addition, the total incorporation amount of the rubber, elastomer and resin is preferably 50 parts by weight or less, more preferably 10 parts by weight or less, and particularly preferably 1 part by weight or less, relative to 100 parts by weight of the acrylic rubber used in the present invention.

At the time of the preparation of the acrylic rubber composition, it is preferable that an acrylic rubber, an aging inhibitor, a crosslinking agent, and other additives be mixed and kneaded in a Banbury mixer, a kneader or the like, and then the mixture be further kneaded using a kneading roller. The order of incorporation of the various components is not particularly limited, but it is preferable to sufficiently mix those components that do not easily undergo reaction or decomposition under heat, prior to mixing a crosslinking agent and the like which are components that easily undergo reaction or decomposition under heat, into the mixture in a short time at a temperature at which reaction or decomposition does not occur. The method of incorporating an aging inhibitor into the acrylic rubber composition is not particularly limited as described above.

The Mooney viscosity ($ML_{1+4}$, 100° C.) (compound Mooney) of the acrylic rubber composition of the present invention is preferably 10 to 100, more preferably 20 to 90, and particularly preferably 25 to 80.

12. Crosslinked Rubber Product

The crosslinked rubber product of the present invention is formed by crosslinking the rubber composition described above.

The crosslinked rubber product of the present invention can be obtained by performing molding by means of a molding machine corresponding to a desired shape, for example, an extruder, an injection molding machine, a compression molding machine, or a roller, and fixing the shape as the crosslinked rubber product through a crosslinking reaction. At that time, the crosslinking may be carried out after molding has been conducted, or simultaneously with molding. The molding temperature is usually 10° C. to 200° C., and preferably 25° C. to 120° C. The crosslinking temperature is usually 130° C. to 220° C., and preferably 150° C. to 190° C., and the crosslinking time is usually two minutes to two hours, and preferably three minutes to an hour. As the heating method, a method that is used in the crosslinking of rubber, such as press heating, vapor heating, oven heating, or hot air heating, may appropriately be selected.

Furthermore, depending on various shapes, sizes and the like of the crosslinked rubber product, in some occasion, the surface is crosslinked, but crosslinking is not sufficiently achieved down to the interior. Therefore, the crosslinked rubber product may further be heated to perform secondary crosslinking. Secondary crosslinking time may vary depending on the heating method, crosslinking temperature, shape and the like, but it is preferably for 1 to 48 hours. The heating method and the heating temperature may be appropriately selected.

Since the crosslinked rubber product obtained in this manner is a crosslinked product obtained by using the rubber composition of the present invention, particularly the acrylic rubber composition, the crosslinked rubber product has excellent heat resistance.

13. Extrusion Molded Article and Sealing Member

The crosslinked rubber product obtained by using the rubber composition of the present invention, particularly the acrylic rubber composition, is suitably used, while appropriately making the best of the characteristics, for various seals such as O-rings, packing, diaphragms, oil seals, shaft seals, bearing seals, mechanical seals, wellhead seals, seals for electric/electronic equipment, and seals for pneumatic equipment; various gaskets such as cylinder head gaskets that are mounted in the connection part between a cylinder block and a cylinder head, rocker cover gaskets that are mounted in the connection part between a rocker cover and a cylinder head, oil pan gaskets that are mounted in the connection part between an oil pan and a cylinder block or a transmission case, fuel cell separator gaskets that are mounted in between a pair of housings which sandwich a unit cell including a positive electrode, an electrolyte plate and a negative electrode, and top cover gaskets for hard disk drives; various belts; various hoses such as fuel hoses, turbo air hoses, oil hoses, radiator hoses, heater hoses, water hoses, vacuum brake hoses, control hoses, air conditioner hoses, brake hoses, power steering hoses, air hoses, marine hoses, risers, and flow lines; various boots such as CVJ boots, propeller shaft boots, constant velocity join boots, and rack and pinion boots; and damping material rubber components such as cushion materials, dynamic dampers, rubber couplings, air springs, and vibration absorbing materials. Particularly, the crosslinked rubber product of the present invention is suitably used in the applications such as extrusion molded articles such as hoses that are used under severe high-temperature conditions, and sealing members such as gaskets and seals.

EXAMPLES

Hereinafter, the present invention will more specifically be described by way of Production Examples (synthesis method) of the diarylamine compounds of the present invention represented by the formulas (I) to (III), which respectively have at least one signal attributable to the hydrogen of the N—H moiety at 8.30 ppm to 9.00 ppm when a deuterated dimethyl sulfoxide solution of the compound is analyzed by $^1$H-NMR, as well as Examples and Comparative Examples. However, the present invention is not intended to be limited to these Production Examples and Examples.

1. Production Example of Diarylamine Compound Represented by Formula (I)

Production Example 1

(Method of Synthesizing Compound 1)
Compound 1

[Chemical Formula 100]

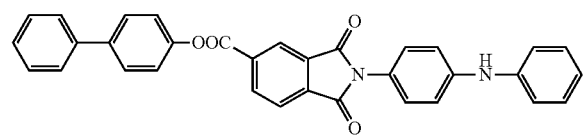

Step 1: Synthesis of Intermediate A
Intermediate A

[Chemical Formula 101]

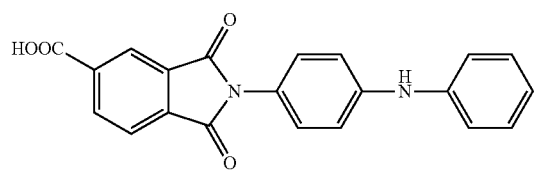

In a four-necked reactor equipped with a cooler and a thermometer, 80 g (0.42 mol) of trimellitic anhydride and 76.7 g (0.42 mol) of 4-aminodiphenylamine were dissolved in a liter of acetic acid under a nitrogen gas stream. This solution was heated to reflux in an oil bath for 10 hours, and was thus subjected to a reaction. After completion of the reaction, the reaction liquid was poured into two liters of water, and a solid was precipitated. Thereafter, the precipitated solid was suction filtered. The resulting filter cake was washed sequentially with water and methanol, and then was dried in a vacuum dryer. Thus, 138.5 g of a yellow-green solid was obtained (yield: 92%). The structure was identified by $^1$H-NMR. $^1$H-NMR (500 MHz, THF-d8, TMS, δ ppm): 6.97 (t, 1H, J=7.0 Hz), 7.24-7.28 (m, 4H), 7.33-7.36 (m, 2H), 7.40-7.42 (m, 2H), 7.68 (s, 1H), 8.11 (d, 1H, J=8.5 Hz), 8.56-8.58 (m, 2H), 12.20 (bs, 1H).

Step 2: Synthesis of Compound 1

In a four-necked reactor equipped with a cooler, a thermometer and a dropping funnel, 10 g (0.028 mol) of the Intermediate A, 5.7 g (0.033 mol) of 4-hydroxybiphenyl, and 400 mg (0.0033 mol) of N,N-dimethyl-4-aminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for 14 hours at room temperature. After completion of the reaction, the reaction liquid was poured into water, and thus a solid was precipitated. The precipitated solid was suction filtered and the filter cake was washed with methanol. The solid thus obtained was dissolved again in 100 ml of N-methylpyrrolidone, and the solution was slowly poured into a liter of methanol to precipitate a solid. The precipitated solid was suction filtered, and the resulting filter cake was washed with methanol. The filter cake thus obtained was dried in a vacuum dryer, and thus 12.1 g of a yellow solid was obtained (yield: 85%). The structure was identified by $^1$H-NMR. $^1$H-NMR (500 MHz, DMF-d7, TMS, δ ppm): 6.92 (t, 1H, J=7.5 Hz), 7.25 (d, 2H, J=7.5 Hz), 7.29-7.33 (m, 4H), 7.41-7.44 (m, 3H), 7.52 (t, 2H, J=8.0 Hz), 7.57 (d, 2H, J=9.0 Hz), 7.77 (dd, 2H, J=1.0 Hz, 8.5 Hz), 7.87 (d, 2H, J=11.5 Hz), 8.22 (d, 1H, J=13.5 Hz), 8.49 (s, 1H), 8.58-8.59 (m, 1H), 8.71 (dd, 1H, J=1.5 Hz, 7.5 Hz).

(Method of Synthesizing Compound 2)
Compound 2

[Chemical Formula 102]

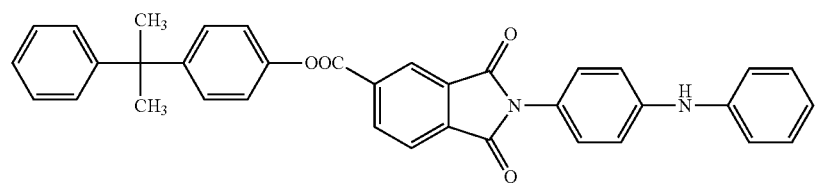

Synthesis was carried out in the same manner as in the synthesis of Compound 1, except that 4-hydroxybiphenyl used in Step 2 was replaced with 7.1 g (0.033 mol) of 4-α-cumylphenol, and thus a yellow-green solid was obtained (yield: 81%). The structure was identified by $^1$H-NMR. $^1$H-NMR (500 MHz, CDCl$_3$, TMS, δ ppm): 1.71 (s, 6H), 7.00 (t, 1H, J=7.0 Hz), 7.12-7.33 (m, 18H), 8.07 (dd, 1H, J=0.5 Hz, 8.0 Hz), 8.60 (dd, 1H, J=1.5 Hz, 8.0 Hz), 8.72-8.73 (m, 1H).

(Method of Synthesizing Compound 3)
Compound 3

[Chemical Formula 103]

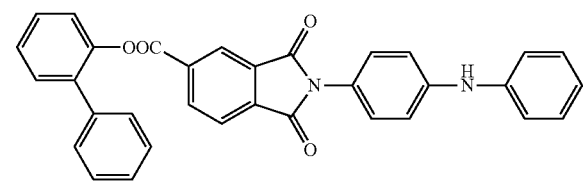

Step 1: The Intermediate A was Synthesized in the Same Manner as in Step 1 of the Synthesis of Compound 1.
Step 2: Synthesis of Compound 3

In a four-necked reactor equipped with a cooler, a thermometer and a dropping funnel, 10 g (0.028 mol) of the Intermediate A, 5.7 g (0.033 mol) of 2-phenylphenol, and 400 mg (0.0033 mol) of N,N-dimethyl-4-aminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for 12 hours at room temperature. After completion of the reaction, the reaction liquid was poured into a solvent mixture of water/methanol=1:1, and thus a solid was precipitated. The precipitated solid was suction filtered. The solid thus obtained was purified by silica gel column chromatography (toluene:ethyl acetate=9:1), and thus 10.7 g of an orange-colored solid was obtained (yield: 75%). The structure was identified by $^1$H-NMR. $^1$H-NMR (500 MHz, DMF-d7, TMS, δ ppm): 5.88 (s, 1H), 6.99 (t, 1H, J=7.5 Hz), 7.13-7.15 (m, 4H), 7.25-7.50 (m, 13H), 7.98 (d, 1H, J=8.0 Hz), 8.40 (dd, 1H, J=1.5 Hz, 7.5 Hz), 8.54-8.55 (m, 1H).

(Method of Synthesizing Compound 4)
Compound 4

[Chemical Formula 104]

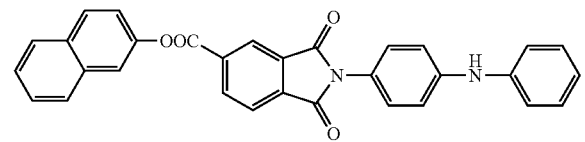

Step 1: The Intermediate A was Synthesized in the Same Manner as in Step 1 of the Synthesis of Compound 1
Step 2: Synthesis of Compound 4

In a four-necked reactor equipped with a cooler, a thermometer and a dropping funnel, 10 g (0.028 mol) of the Intermediate A, 4.8 g (0.033 mol) of 2-naphthol, and 400 mg (0.0033 mol) of N,N-dimethyl-4-aminopyridine were dissolved in 150 ml of N-methylpyrrolidone. 6.4 g (0.033 mol) of 1-ethyl-3-(3-dimethylaminopropyl)carbodiimide hydrochloride (WSC) was added to the solution at room temperature. Thereafter, the mixture was allowed to react for 12 hours at room temperature. After completion of the reaction, the reaction liquid was poured into methanol, and a solid was precipitated. The precipitated solid was suction filtered. The solid thus obtained was purified by silica gel column chromatography (toluene:ethyl acetate=9:1), and thus 7.4 g of a green solid was obtained (yield: 55%). The structure was identified by $^1$H-NMR. $^1$H-NMR (500 MHz, DMF-d7, TMS, δ ppm): 6.93 (t, 1H, J=7.0 Hz) 7.24-7.33 (m, 6H), 7.43 (d, 2H, J=8.5 Hz), 7.58-7.66 (m, 3H), 8.01-8.07 (m, 3H), 8.13 (d, 1H, J=9.0 Hz), 8.24 (d, 1H, J=8.0 Hz), 8.49 (s, 1H), 8.62 (d, 1H, J=1.0 Hz), 8.74 (dd, 1H, J=1.5 Hz, 8.0 Hz).

(Method of Synthesizing Compound 5)
Compound 5

Synthesis was carried out in the same manner as in the synthesis of Compound 4, except that 2-naphthol used in Step 2 was replaced with 6.2 g (0.033 mol) of 4-hydroxydiphenylamine, and thus a yellow-green solid was obtained (yield: 45%). The structure was identified by $^1$H-NMR. $^1$H-NMR (500 MHz, DMF-d7, TMS, δ ppm): 6.84 (t, 1H, J=7.0 Hz), 6.93 (t, 1H, J=7.0 Hz), 7.21 (d, 2H, J=7.0 Hz), 7.24-7.34 (m, 12H), 7.42 (d, 2H, J=7.0 Hz), 8.21 (d, 1H, J=8.0 Hz), 8.32 (s, 1H), 8.49 (s, 1H), 8.55 (s, 1H), 8.67 (dd, 1H, J=1.0 Hz, 7.5 Hz).

(Method of Synthesizing Compound 6)
Compound 6

[Chemical Formula 106]

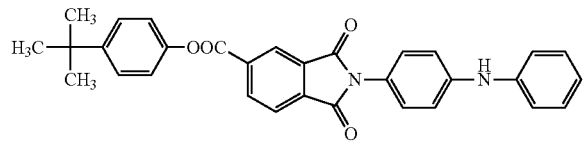

Step 1: The Intermediate A was Synthesized in the Same Manner as in Step 1 of the Synthesis of Compound 1.
Step 2: Synthesis of Compound 6

In a four-necked reactor equipped with a cooler, a thermometer and a dropping funnel, 10 g (0.028 mol) of the Intermediate A, 5.0 g (0.033 mol) of 4-tert-butylphenol, and 400 mg (0.0033 mol) of N,N-dimethyl-4-aminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for 20 hours at room temperature. After completion of the reaction, the reaction liquid was poured into a solvent mixture of water:methanol=1:1, and thus a solid was precipitated. The precipitated solid was suction filtered. The solid thus obtained was dissolved again in 100 ml of N-methylpyrrolidone, and the solution was slowly poured into a solvent mixture of water:methanol=1:1 to precipitate a solid. The precipitated solid was suction filtered, and the resulting filter cake was washed with methanol. The solid thus obtained was purified by silica gel column chromatography (toluene:ethyl acetate=9:1), and thus 5.9 g of a yellow-green solid was obtained (yield: 43%). The structure was identified by $^1$H-NMR. $^1$H-NMR (500 MHz, DMSO-d6, TMS, δ ppm): 1.30 (s, 9H), 6.89 (t, J=7.5 Hz), 7.15-7.19 (m, 4H), 7.28-7.31 (m, 6H), 7.51 (d, 2H, J=9.0 Hz), 8.16 (d, 1H, J=7.5 Hz), 8.44 (s, 1H), 8.47 (s, 1H), 8.58 (dd, 1H, J=1.0 Hz, 7.5 Hz).

[Chemical Formula 105]

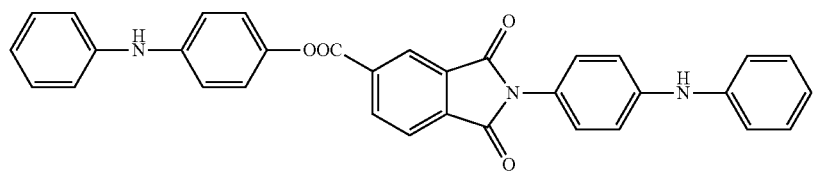

(Method of Synthesizing Compound 7)
Compound 7

[Chemical Formula 107]

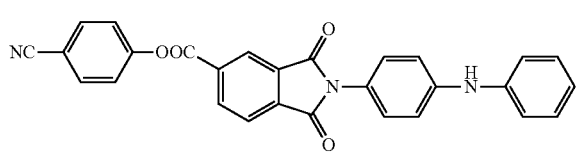

Step 1: The Intermediate A was Synthesized in the Same Manner as in Step 1 of the Synthesis of Compound 1.
Step 2: Synthesis of Compound 7

In a four-necked reactor equipped with a cooler, a thermometer and a dropping funnel, 10 g (0.028 mol) of the Intermediate A, 3.9 g (0.033 mol) of 4-cyanophenol, and 400 mg (0.0033 mol) of N,N-dimethyl-4-aminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for 18 hours at room temperature. After completion of the reaction, the reaction liquid was poured into 1.5 liters of methanol, and a solid was precipitated. The precipitated solid was suction filtered. The solid thus obtained was dissolved again in 100 ml of N-methylpyrrolidone, and the solution was slowly poured again into a liter of methanol to precipitate a solid. The precipitated solid was suction filtered, and thus the resulting filter cake was washed with methanol. The solid thus obtained was purified by silica gel column chromatography (toluene:ethyl acetate=9:1), and thus 9.9 g of an orange-colored solid was obtained (yield: 77%). The structure was identified by $^1$H-NMR. $^1$H-NMR (500 MHz, DMSO-d6, TMS, δ ppm): 6.89 (t, 1H, J=7.5 Hz), 7.14-7.19 (m, 4H), 7.27-7.31 (m, 4H), 7.66 (d, 2H, J=9.0 Hz), 8.03 (d, 2H, J=9.0 Hz), 8.17 (d, 1H, J=8.0 Hz), 8.43 (s, 1H), 8.51 (d, 1H, J=1.0 Hz), 8.60 (dd, 1H, J=1.0 Hz, 7.5 Hz).

(Method of Synthesizing Compound 8)
Compound 8

[Chemical Formula 108]

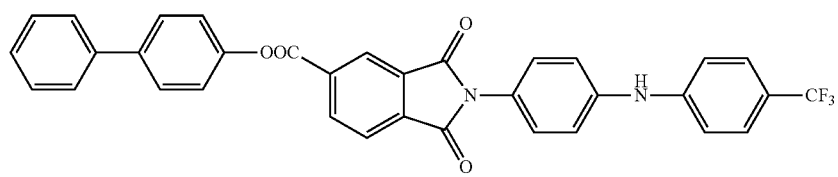

Step 1: Synthesis of Intermediate B
Intermediate B

[Chemical Formula 109]

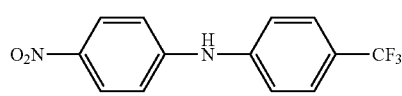

In a two-necked reactor, 40.00 g (147.1 mmol) of 4-iodobenzotrifluoride and 30.47 g (220.6 mmol) of 4-nitroaniline were dissolved in 150 ml of dimethyl sulfoxide under a nitrogen gas stream. 11.70 g (147.1 mmol) of copper(II) oxide and 12.38 g (220.6 mmol) of potassium hydroxide were added to the solution, and the mixture was allowed to react for 8 hours at 110° C. Thereafter, the reaction liquid was returned to room temperature, 1000 ml of distilled water and 500 ml of saturated brine were added thereto, and the mixture was extracted with 500 ml of ethyl acetate. The organic layer was dried over sodium sulfate, concentrated in a rotary evaporator, and then purified by silica gel column chromatography (toluene:tetrahydrofuran=9:1). Thus, 18.20 g of an Intermediate B was obtained (yield 44%). The structure was identified by $^1$H-NMR. $^1$H-NMR (500 MHz, CDCl$_3$, TMS, δ ppm): 6.47 (s, 1H), 7.09 (d, 2H, J=9.0 Hz), 7.27 (d, 2H, J=8.5 Hz), 7.62 (d, 2H, J=8.5 Hz), 8.18 (d, 2H, J=9.0 Hz).

Step 2: Synthesis of Intermediate C
Intermediate C

[Chemical Formula 110]

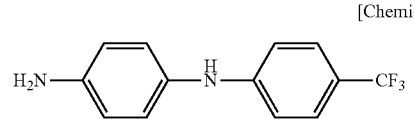

In a three-necked reactor, 17.15 g (60.76 mmol) of the Intermediate B was introduced, and was dissolved in 600 ml of methanol. 3.77 g of 5% palladium-carbon (STD product, water-containing product, manufactured by N.E. Chemcat Corp.) was added to the solution, and the mixture was allowed to react for 5 hours under slight hydrogen pressure. Thereafter, the reaction liquid was filtered using a Kiriyama funnel covered with a filtering aid. The filtrate was concentrated in a rotary evaporator, and the solid thus obtained was purified by silica gel column chromatography (toluene:ethyl acetate=4:1). Thus, 13.84 g of an Intermediate C was obtained (yield 90%). The structure was identified by $^1$H-NMR. $^1$H-NMR (500 MHz, CDCl$_3$, TMS, δ ppm): 3.63 (s, 2H), 5.65 (s, 1H), 6.69 (d, 2H, J=9.0 Hz), 6.79 (d, 2H, J=8.5 Hz), 6.99 (d, 2H, J=9.0 Hz), 7.38 (d, 2H, J=8.5 Hz).

Step 3: Synthesis of Intermediate D
Intermediate D

[Chemical Formula 111]

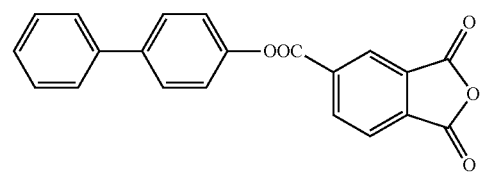

In a three-necked reactor equipped with a thermometer, 16.17 g (94.98 mmol) of 4-phenylphenol, and 7.51 g (94.98 mmol) of pyridine were dissolved in 200 ml of tetrahydrofuran under a nitrogen gas stream. Thereafter, 20 g (94.98 mmol) of trimellitic anhydride chloride was slowly added thereto such that the temperature of the reaction liquid would not rise to 40° C. or higher. The reaction liquid was allowed to react for two hours at room temperature, and 800 ml of methanol was added thereto to precipitate crystals. Crystals thus precipitated were filtered and rinsed with methanol. The crystals thus obtained were dried in a vacuum, and thereby 21.18 g of an Intermediate D was obtained as a white solid (yield 65%). The structure was identified by $^1$H-NMR. $^1$H-NMR (500 MHz, DMSO-d6, TMS, δ ppm): 7.40 (t, 1H, J=7.5 Hz), 7.47-7.51 (m, 4H), 7.70-7.73 (m, 2H), 7.80 (d, 2H, J=9.0 Hz), 8.30 (dd, 1H, J=1.5 Hz, 8.0 Hz), 8.64 (m, 1H), 8.67 (dd, 1H, J=1.5 Hz, 8.0 Hz).

Step 4: Synthesis of Compound 8

In a two-necked reactor, 8.0 g (31.47 mmol) of the Intermediate C, and 13.0 g (37.76 mmol) of the Intermediate D were dissolved in 250 ml of acetic acid under a nitrogen gas stream. The solution was allowed to react for an hour at room temperature, and for another 3 hours under overheating and reflux conditions. Subsequently, the reaction liquid was returned to room temperature, and 500 ml of methanol was added thereto. Precipitated crystals were filtered, and the crystals thus obtained were added to 200 g of 1-methyl-2-pyrrolidone. The mixture was heated to 100° C. to completely dissolve the crystals. To that homogeneous solution, 400 g of a solvent mixture of methanol:ethyl acetate=1:1 was added, and crystals thus precipitated were filtered and dried in a vacuum. Thus, 18.35 g of Compound 8 was obtained as a pale yellow solid (yield 86%). The structure was identified by $^1$H-NMR. $^1$H-NMR (500 MHz, DMSO-d6, TMS, δ ppm): 7.25 (d, 2H, J=8.5 Hz), 7.32 (d, 2H, J=8.5 Hz), 7.38-7.43 m, 3H), 7.48-7.52 (m, 4H), 7.57 (d, 2H, J=9.0 Hz), 7.72 (d, 2H, J=7.0 Hz), 7.80 (d, 2H, J=8.5 Hz), 8.19 (dd, 1H, J=1.0 Hz, 8.0 Hz), 8.53 (dd, 1H, J=1.0 Hz, 1.5 Hz), 8.63 (dd, 1H, J=1.5 Hz, 8.0 Hz), 8.94 (s, 1H).

Production Example 2

Synthesis of Compound 1 According to One-Pot Method

Compound 1, which is a phthalimide group-containing diphenylamine compound having an ester group at the 4-position, was synthesized by Synthesis Examples 1 to 3 that are based on a one-pot method, according to the following reaction scheme (4):

[Chemical Formula 112]

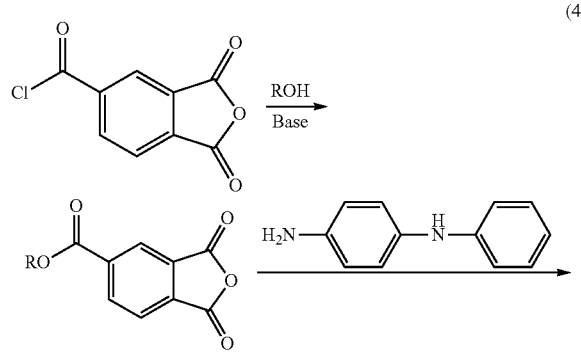

(4)

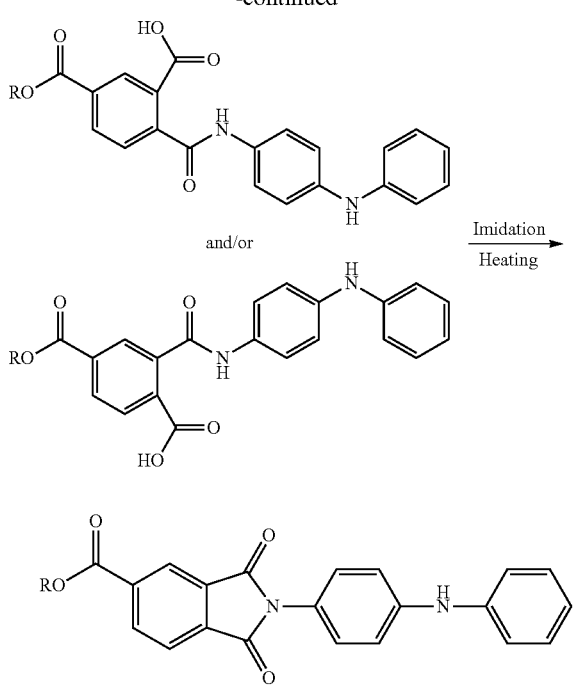

by a one-pot method using the same organic solvent.

As Reference Example 1, reactions were carried out by a two-pot method, while changing the types of the organic solvents used in the respective processes. Furthermore, as Reference Examples 2 and 3, reactions were carried out according to the following reaction scheme (5):

Reaction scheme (5)

[Chemical Formula 113]

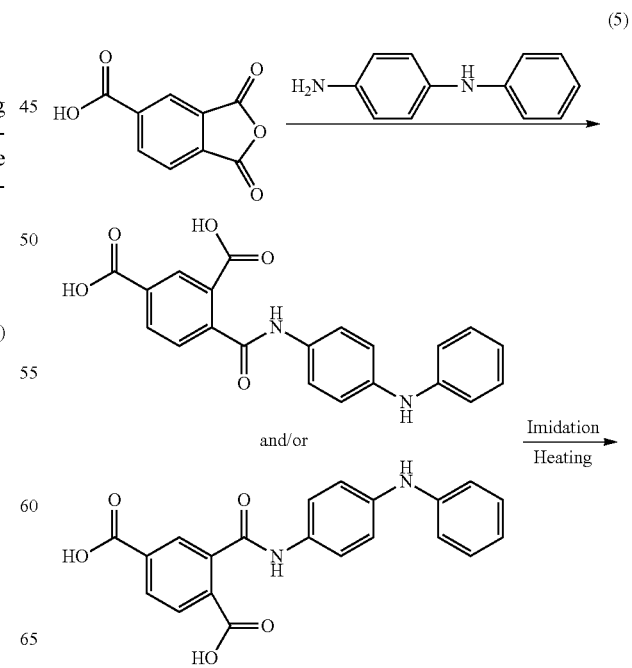

(5)

-continued

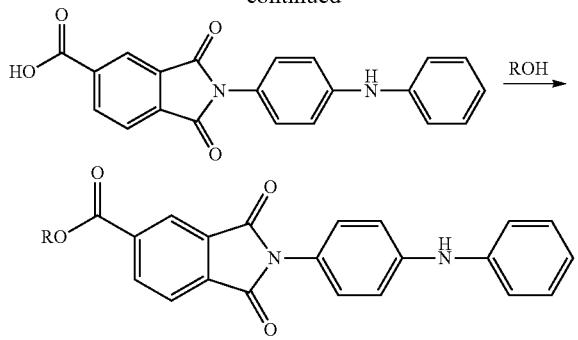

Synthesis Example 1 for Compound 1

Synthesis Example 1 for the Compound 1 is a synthesis example for the following phthalimide group-containing diphenylamine compound having an ester group at the 4-position, which is represented by the formula in the reaction scheme (4) with R=biphenyl:
Compound 1

[Chemical Formula 114]

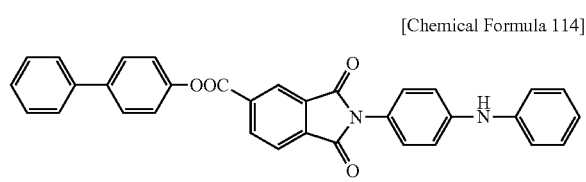

based on a one-pot method.

In a four-necked reactor equipped with a cooler, a thermometer and a dropping funnel, 80 g of N,N-dimethylformamide and 720 g of o-xylene were introduced and stirred under a nitrogen gas stream. 64.8 g (380 mmol) of 4-phenylphenol and 80.0 g (380 mmol) of trimellitic anhydride chloride were sequentially added to the solvent mixture (mixing ratio=10:90), and subsequently, 42.3 g (418 mmol) of triethylamine was slowly added dropwise thereto such that the internal temperature of the reaction solution would not exceed 30° C. After completion of the dropwise addition, the reaction solution was further allowed to react for two hours at an internal temperature of 30'C to 35° C. Subsequently, 70 g (380 mmol) of 4-aminodiphenylamine was added to the reaction solution, and the mixture was allowed to react for three hours under heating and reflux conditions.

After completion of the reaction, the reaction solution was cooled to 55° C., and at that time point, 200 g of methanol was added thereto to precipitate the reaction product. The reaction product as a precipitated solid was suction filtered, and then the filter cake was washed with 80 g of methanol. The filter cake thus obtained was dried in a vacuum dryer, and 162.9 g of a yellow solid was obtained (yield=84%). The chemical structure of the reaction product was identified by $^1$H-NMR.

$^1$H-NMR (500 MHz, DMF-d7, TMS, δ ppm): 6.92 (t, 1H, J=7.5 Hz), 7.25 (d, 2H, J=7.5 Hz), 7.29-7.33 (m, 4H), 7.41-7.44 (m, 3H), 7.52 (t, 2H, J=8.0 Hz), 7.57 (d, 2H, J=9.0 Hz), 7.77 (dd, 2H, J=1.0 Hz, 8.5 Hz), 7.87 (d, 2H, J=11.5 Hz), 8.22 (d, 1H, J=13.5 Hz), 8.49 (s, 1H), 8.58-8.59 (m, 1H), 8.71 (dd, 1H, J=1.5 Hz, 7.5 Hz).

Synthesis Example 2 for Compound 1

The phthalimide group-containing diphenylamine compound having an ester group at the 4-position (Compound 1), which is represented by the formula in the reaction scheme (4) with R=biphenyl, was synthesized according to the one-pot method, by the same operation as that used in Synthesis Example 1, except that the solvent mixture of N,N-dimethylformamide and o-xylene as the reaction solvent was replaced with a single solvent of o-xylene.

Synthesis Example 3 for Compound 1

The phthalimide group-containing diphenylamine compound having an ester group at the 4-position (Compound 1), which is represented by the formula in the reaction scheme (4) with R=biphenyl, was synthesized according to the one-pot method, by the same operation as that used in Synthesis Example 1, except that the solvent mixture of N,N-dimethylformamide and o-xylene as the reaction solvent was replaced with methyl isobutyl ketone.

Reference Example 1

The phthalimide group-containing diphenylamine compound having an ester group at the 4-position shown above (Compound 1), which is represented by the formula in the reaction scheme (4) with R=biphenyl, was synthesized by the following two-pot method.
Step 1:

200 ml of tetrahydrofuran was introduced into a three-necked reactor equipped with a thermometer under a nitrogen gas stream, and then 16.17 g (94.98 mmol) of 4-phenylphenol and 7.51 g (94.98 mmol) of pyridine were added thereto while stirred, and were dissolved in the tetrahydrofuran. Subsequently, 20 g (94.98 mmol) of trimellitic anhydride chloride was added slowly to the solution such that the temperature of the reaction solution would not rise to 40° C. or higher. Thereafter, the mixture was allowed to react for two hours at room temperature.

After completion of the reaction, 800 ml of methanol was added to the reaction solution, and thereby, a reaction product was precipitated. Subsequently, the precipitated crystals were filtered and rinsed with methanol. The crystals thus obtained were dried in a vacuum, and 21.18 g of an Intermediate E was obtained as a white solid (yield in Step 1: 65%). This Intermediate E is a phthalic anhydride derivative having an ester group at the 4-position, as represented by the following formula (6):
Intermediate E (Formula (6))

[Chemical Formula 115]

(6)

The chemical structure of the Intermediate E was identified by $^1$H-NMR.

$^1$H-NMR (500 MHz, DMSO-d6, TMS, δ ppm): 7.40 (t, 1H, J=7.5 Hz), 7.47-7.51 (m, 4H), 7.70-7.73 (m, 2H), 7.80 (d, 2H, J=9.0 Hz), 8.30 (dd, 1H, J=1.5 Hz, 8.0 Hz), 8.64 (m, 1H), 8.67 (dd, 1H, J=1.5 Hz, 8.0 Hz).
Step 2:

In a two-necked reactor, 8.0 g (31.47 mmol) of 4-aminodiphenylamine and 13.0 g (37.76 mmol) of the Intermediate E were dissolved in 250 ml of acetic acid under a nitrogen gas stream. The solution was allowed to react for an hour at room temperature, and for another 3 hours under heating and reflux conditions. After completion of the reaction, the reaction solution was returned to room temperature, and 500 ml of methanol was added thereto. Precipitated crystals were filtered. The crystals thus obtained were added to 200 g of N-methyl-2-pyrrolidone, and the mixture was heated to 100° C. and was thereby completely dissolved. 400 g of a solvent mixture of methanol:ethyl acetate=1:1 was added to the uniform solution thus obtained, and thus, crystals were precipitated. The crystals thus precipitated were filtered and dried in a vacuum, and thereby, 18.35 g of a product was obtained as a pale yellow solid (yield in Step 2: 86%). This product was a phthalimide group-containing diphenylamine compound having an ester group at the 3-position, with R=biphenyl. The total yield of the compound obtained after Step 1 and Step 2 was 56%.

Reference Example 2

The phthalimide group-containing diphenylamine compound having an ester group at the 4-position (IV-c), which is represented by the formula in the reaction scheme (5) with R=biphenyl, was synthesized by the following two-pot method.
Step 1:
In a four-necked reactor equipped with a cooler and a thermometer, 80 g (0.42 mol) of trimellitic anhydride and 76.7 g (0.42 mol) of 4-aminodiphenylamine were dissolved in a liter of acetic acid under a nitrogen gas stream. This solution was allowed to react while heated to reflux for 10 hours in an oil bath. After completion of the reaction, the reaction liquid was poured into two liters of water, and a reaction product was precipitated. Thereafter, the reaction product as a precipitated solid was suction filtered. The filter cake was washed sequentially with water and methanol, and then was dried in a vacuum dryer. Thus, 138.5 g of a purified reaction product was obtained as a yellow-green solid (yield in Step 1: 92%). In this manner, an Intermediate F formed from an N-(4-phenylaminophenyl)-phthalimide compound having a carboxyl group at the 4-position, as represented by the following formula (7):
Formula (7)

[Chemical Formula 116]

(7)

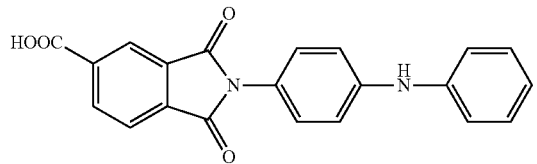

was synthesized. The chemical structure of the Intermediate F was identified by $^1$H-NMR.
$^1$H-NMR (500 MHz, THF-d8, TMS, δ ppm): 6.97 (t, 1H, J=7.0 Hz), 7.24-7.28 (m, 4H), 7.33-7.36 (m, 2H), 7.40-7.42 (m, 2H), 7.68 (s, 1H), 8.11 (d, 1H, J=8.5 Hz), 8.56-8.58 (m, 2H), 12.20 (bs, 1H).
Step 2:
In a four-necked reactor equipped with a cooler and a thermometer, 10 g (0.028 mol) of the Intermediate F, 5.7 g (0.033 mol) of 4-hydroxybiphenyl, and 400 mg (0.0033 mol) of N,N-dimethylaminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) as a condensing agent was added to the solution at room temperature. Thereafter, the mixture was allowed to react for 14 hours at room temperature.

After completion of the reaction, the reaction solution was poured into water, and thereby a reaction product was precipitated. The reaction product as a precipitated solid was suction filtered. The solid thus obtained was dissolved again in 100 ml of N-methyl-2-pyrrolidone. The solution thus obtained was slowly poured into a liter of methanol, and thus a solid was precipitated. The precipitated solid was suction filtered, and the filter cake was washed with methanol. Furthermore, the solid thus obtained was dissolved again in 100 ml of N-methyl-2-pyrrolidone, and then the solution was slowly poured into a liter of methanol to precipitate the solid. The solid thus precipitated was suction filtered, and the filter cake was washed with methanol. The filter cake thus obtained was dried in a vacuum dryer, and thus 12.1 g of a purified reaction product (Compound 1) was obtained (yield at Step 2: 85%). The total yield of the Compound 1 obtained after Step 1 and Step 2 was 78%.

Reference Example 3

The phthalimide group-containing diphenylamine compound having an ester group at the 4-position, which is represented by the formula in the reaction scheme (5) with R=biphenyl, was synthesized by the following two-pot method.
Step 1:
An Intermediate F represented by the formula (7) was synthesized in the same manner as in Reference Example 2.
Step 2:
In a four-necked reactor equipped with a cooler, a thermometer and a dropping funnel, 10 g (0.028 mol) of the Intermediate F was dissolved in 150 ml of N-methyl-2-pyrrolidone under a nitrogen gas stream. 5.59 g (0.029 mol) of p-toluenesulfonyl chloride was added to the solution at room temperature, and 3.1 g (0.031 mol) of triethylamine was slowly added dropwise thereto. Subsequently, the mixture was allowed to react for two hours. Thereafter, 3.8 g (0.023 mol) of 2-phenylphenol, 2.8 g (0.00.028 mol) of triethylamine, and 340 mg (0.0028 mol) of N,N-dimethylaminopyridine were sequentially added to the reaction solution, and then the resulting mixture was allowed to react for two hours at room temperature.

After completion of the reaction, 4.5 g (0.14 mol) of methanol was added to the reaction solution, and the mixture was stirred for an hour. Subsequently, the reaction solution was poured into 300 g of a solvent mixture of methanol:ethyl acetate=1:2 (volume ratio), and thus a solid was precipitated. The precipitated solid was suction filtered, and the filter cake was washed with methanol. Furthermore, the solid thus obtained was dissolved again in 100 ml of N-methyl-2-pyrrolidone. This solution was slowly poured into a liter of methanol, and thereby, a solid was precipitated. The precipitated solid was suction filtered, and the filter cake was washed with methanol. The filter cake thus obtained was dried in a vacuum dryer, and thus 11.5 g of a purified compound (Compound 1) was obtained (yield at Step 2: 81%). The total yield of the Compound 1 obtained after Step 1 and Step 2 was 75%.

The results of Synthesis Examples 1 to 3 and Reference Examples 1 to 3 are summarized in Table 2 (in Table 2, the "Synthesis Example" is simply indicated as "Example"). The purity of the compound was measured by high performance liquid chromatography.

(Conditions for High Performance Liquid Chromatography)

The analysis by high performance liquid chromatography was carried out under the following conditions.

Apparatus: 1100 series manufactured by Agilent Technologies, Inc.

Eluent: acetonitrile:THF:water (buffer: potassium dihydrogen phosphate 5 mM)=65:15:20 (volume ratio)

Column: ZERBAX ECLIPSE XDB-C18 (registered trademark) (4.6 mmϕ×250 mm in length) manufactured by Agilent Technologies, Inc.

Temperature: 40° C.
Flow rate: 1 ml/min
Detection UV: 254 nm

TABLE 2

| | Claim 1 | | Yield | Purity | Reaction reagent · solvent |
|---|---|---|---|---|---|
| | Synthesis route | Reaction solvent | (%) | (%) | cost |
| Example 1 | Esterification → amidation → imidation One-pot method | N,N-dimethylformamide/ o-xylene = 1/9 | 84 | 97.5 | A |
| Example 2 | Esterification → amidation → imidation One-pot method | o-xylene | 80 | 97.4 | A |
| Example 3 | Esterification → amidation → imidation One-pot method | Methyl isobutyl ketone | 83 | 97.2 | A |
| Reference Example 1 | Esterification → amidation → imidation Two-pot method | THF → acetic acid | 56 | 98.0 | B |
| Reference Example 2 | Amidation → imidation → esterification Two-pot method | Acetic acid → NMP | 78 | 98.4 | B |
| Reference Example 3 | Amidation → imidation → esterification Two-pot method | Acetic acid → NMP | 75 | 97.8 | B |

Footnote:
The reaction reagent/solvent cost was evaluated by the following criteria, based on the price of the reaction reagent used and the use amount of the organic solvent.
A: Cost is relatively low.
B: Use of expensive reaction reagents and/or large amounts of organic solvents are/is needed.

In Reference Example 1, since the purification loss in the post-treatment after the esterification reaction is large, the yield is deteriorated. In Reference Examples 2 and 3, a method of esterification is employed after trimellitic anhydride is subjected to imidation using trimellitic anhydride as a raw material. In this method, the solubility of the Intermediate obtainable by the imidation in an organic solvent is poor, and therefore, it is necessary to use a large amount of N-methyl-2-pyrrolidone (NMP) as an organic solvent in the second reaction. As a result, not only the solvent cost increases, but also the number of purification processes increases. Thus, the two-pot method is not adequate for an industrial production method.

On the contrary, in Synthesis Examples 1 to 3, the target product can conveniently be isolated with high purity only by filtration, after completion of the reaction. Furthermore, since the reaction can be carried out in a one-pot process, the time required for the reaction process is shortened to a large extent, and an intended compound can be produced with high productivity at low cost.

Synthesis Example 4 of Compound 4

Compound 4, which is represented by the formula in the reaction scheme (4) with R in R'''OH=naphthyl:

[Chemical Formula 117]

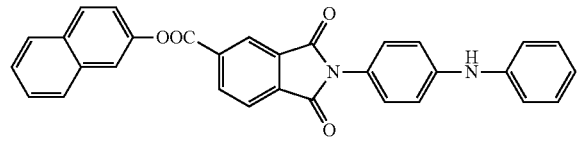

was synthesized according to a one-pot method.

The same procedure as that used in Synthesis Example 1 was carried out, except that 64.8 g of 4-phenylphenol was replaced with 54.8 g (380 mmol) of 2-naphthol, and thus a yellow-green solid was obtained (yield: 75%). The yellow-green solid was a phthalimide group-containing diphenylamine compound 4 (IV-f) having an ester group at the 4-position. The chemical structure of the reaction product was identified by $^1$H-NMR.

$^1$H-NMR (500 MHz, DMF-d7, TMS, δ ppm): 6.93 (t, 1H, J=7.0 Hz) 7.24-7.33 (m, 6H), 7.43 (d, 2H, J=8.5 Hz), 7.58-7.66 (m, 3H), 8.01-8.07 (m, 3H), 8.13 (d, 1H, J=9.0 Hz), 8.24 (d, 1H, J=8.0 Hz), 8.49 (s, 1H), 8.62 (d, 1H, J=1.0 Hz), 8.74 (dd, 1H, J=1.5 Hz, 8.0 Hz).

Synthesis Example 5 of Compound 7

The following compound 7, which is represented by the formula in the reaction scheme (4) with R of R'''OH=4-cyanobenzene:

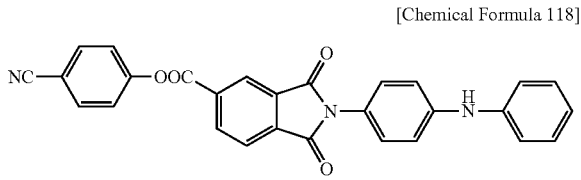

[Chemical Formula 118]

was synthesized according to a one-pot method.

Synthesis was carried out in the same manner as in Synthesis Example 1, except that 64.8 g of 4-phenylphenol was replaced with 45.3 g (380 mmol) of 4-cyanophenol, and thus a yellow-green solid was obtained (yield: 78%). This yellow-green solid was a phtahlimide group-containing diphenylamine compound 7 (IV-i) having an ester group at the 4-position. The chemical structure of the reaction product was identified by $^1$H-NMR.

$^1$H-NMR (500 MHz, DMSO-d6, TMS, δ ppm): 6.89 (t, 1H, J=7.5 Hz), 7.14-7.19 (m, 4H), 7.27-7.31 (m, 4H), 7.66 (d, 2H, J=9.0 Hz), 8.03 (d, 2H, J=9.0 Hz), 8.17 (d, 1H, J=8.0 Hz), 8.43 (s, 1H), 8.51 (d, 1H, J=1.0 Hz), 8.60 (dd, 1H, J=1.0 Hz, 7.5 Hz).

2. Production Example of Diarylamine Compound Represented by Formula (II)

Synthesis Method

Production Example (Method of Synthesizing Compound 9)
Compound 9

[Chemical Formula 119]

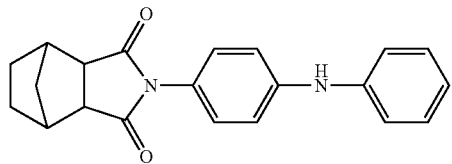

Step 1: Synthesis of Intermediate G
Intermediate G

[Chemical Formula 120]

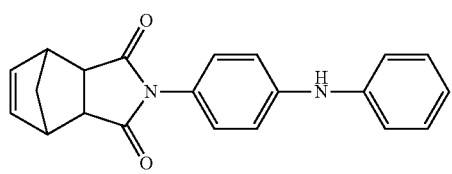

In a four-necked reactor equipped with a cooler and a thermometer, 10 g (0.061 mol) of 5-norbornene-2,3-dicarboxylic acid anhydride and 11.2 g (0.061 mol) of 4-aminodiphenylamine were dissolved in 500 ml of acetic acid under a nitrogen gas stream. This solution was allowed to react while heated to reflux for six hours in an oil bath. After completion of the reaction, the reaction liquid was poured into a liter of water, and thereby a solid was precipitated. Thereafter, the precipitated solid was suction filtered. The filter cake was washed with water, and then the solid of the filter cake thus obtained, and 250 ml of methanol were introduced into a three-necked reactor equipped with a cooler and a thermometer. The mixture was heated to reflux for an hour under a nitrogen gas stream, subsequently 125 ml of water was added thereto, and the mixture was cooled to 0° C. to precipitate crystals. The crystals thus precipitated were suction filtered. Thereafter, the crystals as the filter cake were rinsed with a solvent mixture of methanol/water=2/1. The crystals thus obtained were dried in a vacuum dryer, and 18.3 g of a colorless solid was obtained (yield: 91%). The structure was identified by $^1$H-NMR. $^1$H-NMR (500 MHz, DMSO-d6, TMS, δ ppm): 1.57-1.61 (m, 2H), 3.31-3.33 (m, 2H), 3.45 (dd, 2H, J=1.8 Hz, 2.5 Hz), 6.26 (t, 2H, J=1.8 Hz), 6.86 (t, 1H, J=7.5 Hz), 6.92 (d, 2H, J=9.0 Hz), 7.07 (d, 2H, J=9.0 Hz), 7.09 (d, 2H, J=8.5 Hz), 7.24 (dd, 2H, J=7.5 Hz, 8.5 Hz), 8.35 (s, 1H).

Step 2: Synthesis of Compound 9

In a four-necked reactor equipped with a cooler and a thermometer, 10.0 g (0.03 mol) of the Intermediate G and 1 g of 5% palladium-carbon (STD product, water-containing product, manufactured by N.E. Chemcat Corp.) were added to 300 ml of a solvent mixture of tetrahydrofuran/methanol=2/1 under a nitrogen gas stream, and the mixture was allowed to react for 16 hours at room temperature under a slight hydrogen pressure. After completion of the reaction, the reaction liquid was suction filtered with a Kiriyama funnel covered with a filtering aid. The solvent of the filtrate thus obtained was distilled off in a rotary evaporator. The solid thus obtained was purified by silica gel column chromatography (hexane:tetrahydrofuran=3:2), and thus a pale yellow solid was obtained. Furthermore, the pale yellow solid thus obtained was subjected to recrystallization from toluene, and thus 7.3 g of colorless crystals were obtained (yield: 73%). The structure was identified by $^1$H-NMR. $^1$H-NMR (500 MHz, CDCl$_3$, TMS, δ ppm): 1.44-1.48 (m, 2H), 1.64-1.73 (m, 4H), 2.83-2.89 (m, 2H), 3.20-3.25 (m, 2H), 5.88 (s, 1H), 6.98 (t, 1H, J=7.5 Hz), 7.09-7.12 (m, 6H), 7.28 (dd, 2H, J=7.5 Hz, 8.5 Hz).

3. Examples Involving Compounds 1 to 9, and Comparative Examples

The structures and molecular weights of the diarylamine compounds 1 to 9 synthesized in the Production Examples, and the conventional diphenylamine-based compounds used in Comparative Examples are presented in Table 3 and Table 4.

TABLE 3

| Formula | | Chemical structure | Molecular weight |
|---|---|---|---|
| I | Compound 1 | 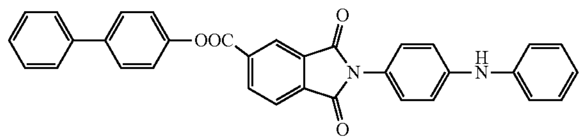 | 510.6 |
| | Compound 2 | | 552.7 |
| | Compound 3 | | 510.6 |
| | Compound 4 | | 484.5 |
| | Compound 5 | | 525.6 |
| | Compound 6 | | 490.6 |
| | Compound 7 | | 459.5 |
| | Compound 8 | | 578.5 |
| II | Compound 9 | 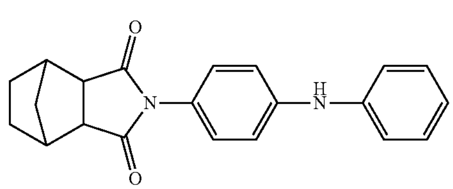 [SMILES: O=C1C2C3CCC(C3)C2C(=O)N1c1ccc(Nc2ccccc2)cc1] | 332.4 |

TABLE 4

| | Conventional diphenylamine-based compounds | |
|---|---|---|
| | Chemical structure | Molecular weight |
| Diphenylamine | 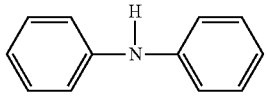 [SMILES: c1ccc(Nc2ccccc2)cc1] | 169.2 |
| STEARER-STAR (manufactured by Seiko Chemical Co., Ltd.) | 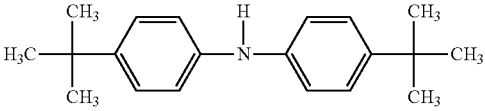 | 281.4 |
| NONFLEX LAS-P (manufactured by Seiko Chemical Co., Ltd.) | 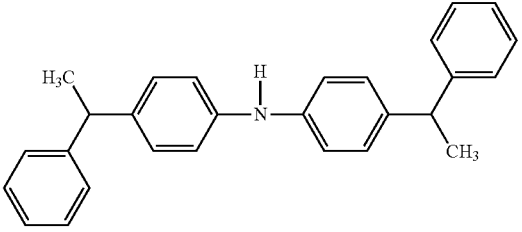 [SMILES: CC(c1ccccc1)c1ccc(Nc2ccc(C(C)c3ccccc3)cc2)cc1] 28.6%:71.4% mixture | 303.2 |
| NOCRAC WHITE (manufactured by Ouchi Shinko Chemical Industrial Co., Ltd.) | 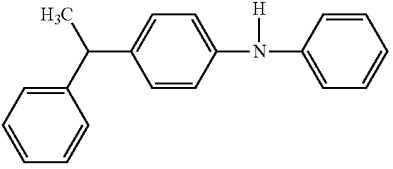 [SMILES: CC(c1ccccc1)c1ccc(Nc2ccccc2)cc1] | 360.5 |
| NOCRAC DP (manufactured by Ouchi Shinko Chemical Industrial Co., Ltd.) | 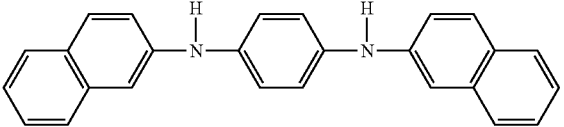 [SMILES: c1ccc2cc(Nc3ccc(Nc4ccc5ccccc5c4)cc3)ccc2c1] | 260.3 |
| NOCRAC AD-F (manufactured by Ouchi Shinko Chemical Industrial Co., Ltd.) | 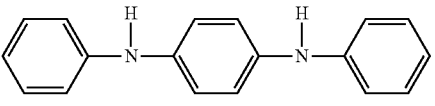 [SMILES: c1ccc(Nc2ccc(Nc3ccccc3)cc2)cc1] | 393.7 |
| NAUGARD 445 (manufactured by Shiraishi Calcium Kaisha, Ltd.) | 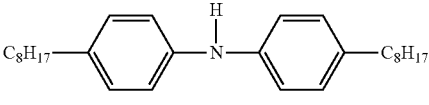 | 405.6 |

EXAMPLES AND COMPARATIVE EXAMPLES

Hereinafter, evaluations of the diarylamine compound of the present invention used as aging inhibitors, as represented by any one of the formula (I) and formula (II), which has at least one signal attributable to the hydrogen of the N—H moiety at 8.30 ppm to 9.00 ppm when a deuterated dimethyl sulfoxide solution of the diarylamine compound is analyzed by $^1$H-NMR, will be described by way of Examples. However, the present invention is not intended to be limited to these Examples. In the following descriptions, the units "parts" and "percent (%)" are on a weight basis unless particularly stated otherwise. The preparation of test specimens and the evaluation of heat resistance are as follows.

(Preparation of Test Specimen)

A rubber composition was molded by pressing at 170° C. for 20 minutes and crosslinked, and thus a sheet having a size of 15 cm×15 cm×2 mm was produced. Furthermore, this sheet was subjected to secondary crosslinking by heating at 170° C. for four hours. A dumbbell-shaped No. 3 test specimen was produced from this sheet.

(Evaluation of Heat Resistance)

The evaluation of heat resistance was carried out by measuring, according to JIS K6251, the respective elongations of test specimens thus produced from an acrylic rubber composition in an environment at 190° C. and test specimens produced from a hydrogenated nitrile rubber composition in an environment at 150° C., before and after a time lapse of 504 hours of standing; and calculating the change ratios (absolute values) of the elongations according to the following calculation formula.

It is considered that as closer to zero the change ratio is, higher heat resistance is obtained, which leads to preferable results.

Calculation formula:

Change ratio (%)=|100×[(elongation before test (%))−(elongation after test (%))]/(elongation before test (%))|.

I. Acrylic Rubber Composition

Examples 1 to 11 and Comparative Examples 1 to 8

(1) Preparation of Rubber Composition 100 parts by weight of an acrylic rubber (manufactured by Zeon Corp., Nipol AR22), 60 parts by weight of carbon black (manufactured by Tokai Carbon Co., Ltd., SEAST SO), 2 parts by weight of stearic acid, and an aging inhibitor, one of Compounds 1 to 9 synthesized in the Production Examples described above in a predetermined amount as indicated in Table 5, were mixed, and the mixture was kneaded for five minutes at 50° C. using a 0.8-liter Banbury mixer. Subsequently, 0.5 parts by weight of hexamethylenediamine carbamate (manufactured by DuPont Dow Elastomers Japan K.K., Diak No. 1) as a crosslinking agent, and 2 parts by weight of di-o-tolylguanidine (manufactured by Ouchi Shinko Chemical Industrial Co., Ltd., NOCCELER DT) as a crosslinking accelerating agent were kneaded with an open roll. Thus, a rubber composition was prepared.

Rubber compositions were prepared, without adding an aging inhibitor in Comparative Example 1, and by adding conventionally known diphenylamine-based aging inhibitors in Comparative Examples 2 to 8.

(2) Evaluation of Heat Resistance

The results of the evaluation of heat resistance are presented in the following Table 5. In Examples 1 to 11 which use the diarylamine compound represented by any one of the formulas (I) and (II) of the present invention as aging inhibitors, even under the severe conditions of standing for 504 hours in an environment at 190° C., smaller changes in the elongation were recognized as compared with Comparative Examples i to 8, and thus it was confirmed that heat resistance was enhanced.

Furthermore, from Examples 1 to 3, it was recognized that heat resistance was further enhanced by increasing the incorporation amount of the compound of the present invention, and thus the effect of incorporating the compound of the present invention as an aging inhibitor was confirmed.

TABLE 5

| Incorporated formulation | | | Ex. 1 | Ex. 2 | Ex. 3 | Ex. 4 | Ex. 5 | Ex. 6 | Ex. 7 |
|---|---|---|---|---|---|---|---|---|---|
| AR22 | | pts. wt.[1*] | 100 | 100 | 100 | 100 | 100 | 100 | 100 |
| SEAST SO | | pts. wt. | 60 | 60 | 60 | 60 | 60 | 60 | 60 |
| Stearic acid | | pts. wt. | 2 | 2 | 2 | 2 | 2 | 2 | 2 |
| Aging inhibitor | Type | | Cpd.[*2] 1 | | | Cpd. 2 | Cpd. 3 | Cpd. 4 | Cpd. 5 |
| | Addition amount relative to 100 parts by weight of rubber | pts. wt. | 2.52 | 5.03 | 7.55 | 2.72 | 2.52 | 2.39 | 1.30 |
| | Addition amount relative to 100 g of rubber | mmol | 4.93 | 9.86 | 14.79 | 4.93 | 4.93 | 4.93 | 2.47 |
| DIAK No. 1 | | pts. wt. | 0.5 | 0.5 | 0.5 | 0.5 | 0.5 | 0.5 | 0.5 |
| NOCCELER DT | | pts. wt. | 2.0 | 2.0 | 2.0 | 2.0 | 2.0 | 2.0 | 2.0 |
| Elongation at break | | % | 260 | 260 | 260 | 250 | 270 | 260 | 250 |
| Elongation change ratio after a lapse of time for 504 hours at 190° C. | | % | 74 | 68 | 65 | 78 | 77 | 79 | 78 |

| Incorporated formulation | | | Ex. 8 | Ex. 9 | Ex. 10 | Ex. 11 | Comp Ex. 1 | Comp. Ex. 2 | Comp. Ex. 3 |
|---|---|---|---|---|---|---|---|---|---|
| AR22 | | pts. wt.[1*] | 100 | 100 | 100 | 100 | 100 | 100 | 100 |
| SEAST SO | | pts. wt. | 60 | 60 | 60 | 60 | 60 | 60 | 60 |
| Stearic acid | | pts. wt. | 2 | 2 | 2 | 2 | 2 | 2 | 2 |
| Aging inhibitor | Type | | Cpd. 6 | Cpd. 7 | Cpd. 8 | Cpd.[*2] 9 | None | Diphenylamine | STEARER-STAR |
| | Addition amount relative to 100 parts by weight of rubber | pts. wt. | 2.42 | 2.27 | 2.85 | 1.64 | 0.00 | 0.84 | 1.39 |
| | Addition amount relative to 100 g of rubber | mmol | 4.93 | 4.93 | 4.93 | 4.93 | 0.00 | 4.93 | 4.93 |
| DIAK No. 1 | | pts. wt. | 0.5 | 0.5 | 0.5 | 0.5 | 0.5 | 0.5 | 0.5 |
| NOCCELER DT | | pts. wt. | 2.0 | 2.0 | 2.0 | 2.0 | 2.0 | 2.0 | 2.0 |
| Elongation at break | | % | 250 | 250 | 260 | 250 | 250 | 260 | 260 |
| Elongation change ratio after a lapse of time for 504 hours at 190° C. | | % | 77 | 76 | 72 | 71 | 90 | 87 | 88 |

TABLE 5-continued

| Incorporated formulation | | | Comp. Ex. 4 | Comp. Ex. 5 | Comp. Ex. 6 | Comp. Ex. 7 | Comp. Ex. 8 |
|---|---|---|---|---|---|---|---|
| AR22 | | pts. wt.[1*] | 100 | 100 | 100 | 100 | 100 |
| SEAST SO | | pts. wt. | 60 | 60 | 60 | 60 | 60 |
| Stearic acid | | pts. wt. | 2 | 2 | 2 | 2 | 2 |
| Aging inhibitor | Type | | NONFLEX LAS-P | NOCRAC WHITE | NOCRAC DP | NOCRAC AD-F | NAUGARD 445 |
| | Addition amount relative to 100 parts by weight of rubber | pts. wt. | 1.50 | 1.78 | 1.28 | 1.94 | 2.00 |
| | Addition amount relative to 100 g of rubber | mmol | 4.93 | 4.93 | 4.93 | 4.93 | 4.93 |
| DIAK No. 1 | | pts. wt. | 0.5 | 0.5 | 0.5 | 0.5 | 0.5 |
| NOCCELER DT | | pts. wt. | 2.0 | 2.0 | 2.0 | 2.0 | 2.0 |
| Elongation at break | | % | 250 | 260 | 270 | 260 | 260 |
| Elongation change ratio after a lapse of time for 504 hours at 190° C. | | % | 85 | 84 | 85 | 83 | 80 |

[1*]pts. wt.: parts by weight
[2*]Cpd.: Compound

II. Hydrogenated Nitrile Rubber Composition

Examples 12 and 13, and Comparative Example 9

(1) Preparation of Rubber Composition 100 parts by weight of a hydrogenated nitrile rubber (manufactured by Zeon Corp., Zetpol 2000L), 40 parts by weight of FEF carbon black (manufactured by Tokai Carbon Co., Ltd., SEAST SO), 1 part by weight of stearic acid, 5 parts by weight of tri(2-ethylhexyl)trimellitate (manufactured by Adeka Corp., ADEKACIZER C-8), 5 parts by weight of zinc oxide (manufactured by Sakai Chemical Industry Co., Ltd., zinc oxide No. 1), a specified amount of an aging inhibitor as indicated in Table 6, and 1.5 parts by weight of a zinc salt of 2-mercaptobenzimidazole (manufactured by Ouchi Shinko Chemical Industrial Co., Ltd., NOCRAC MBZ) were kneaded for five minutes at 50° C. using a 0.8-liter Banbury mixer. Subsequently, 10 parts by weight of 2,2'-bis(tert-butylperoxydiisopropyl)benzene (manufactured by Hercules, Inc., Vul-cup 40KE) as a crosslinking agent was kneaded with an open roll. Thus, rubber compositions to be provided for Examples 12 and 13 were prepared.

In Comparative Example 9, a rubber composition was prepared by adding a conventionally known diphenylamine-based aging inhibitor.

(2) Evaluation of Heat Resistance

The results of the evaluation of heat resistance are presented in Table 6. It can be seen that when the diarylamine compounds represented by any one of the formula (I) and (II) of the present invention are used as aging inhibitors, even under the severe conditions of standing for 504 hours in an environment at 150° C., the changes in the elongation are small, and therefore, heat resistance has been enhanced.

TABLE 6

| Incorporated formulation | | | Example 12 | Example 13 | Comparative Example 9 |
|---|---|---|---|---|---|
| ZP2000L | | parts by weight | 100 | 100 | 100 |
| SEAST SO | | parts by weight | 40 | 40 | 40 |
| ADEKACIZER C-8 | | parts by weight | 5 | 5 | 5 |
| NOCRAC MBZ | | parts by weight | 1.5 | 1.5 | 1.5 |
| Zinc oxide No. 1 | | parts by weight | 5 | 5 | 1 |
| Stearic acid | | parts by weight | 1 | 1 | |
| | Type | | Compound 1 | Compound 1 | NAUGARD 445 |
| Aging inhibitor | Addition amount relative to 100 parts by weight of rubber | parts by weight | 2.04 | 1.23 | 1.50 |
| | Addition amount of relative to 100 g of rubber | mmol | 3.70 | 3.70 | 3.70 |
| VUL-CUP 40KE | | parts by weight | 10.0 | 10.0 | 10.0 |
| Elongation at break | | % | 360 | 360 | 360 |
| Elongation change ratio after a lapse of time for 504 hours at 150° C. | | % | 15 | 19 | 25 |

4. Production Example of Diarylamine Compound Represented by Formula (III)

Synthesis Method

Production Example

Compounds 10 to 25 were produced by the following method. Each of the compounds synthesized in the Production Example was analyzed by $^1$H-NMR using a deuterated dimethyl sulfoxide solvent. If necessary, the signal derived from the N—H moiety was characterized by using a $^{13}$C nucleus, $^1$H—$^{13}$C COSY method. In regard to the Compounds 10 to 25, and conventionally known aging inhibitors, the molecular weights, and the signal attributable to the hydrogen of the N—H moiety at 8.30 ppm to 9.00 ppm when deuterated dimethyl sulfoxide (DMSO-d6) solutions of the compounds are analyzed by $^1$H-NMR, are as summarized in the Table 1-1 and Table 1-2 described above.

(Method of Synthesizing Compound 10)
Compound 10

[Chemical Formula 121]

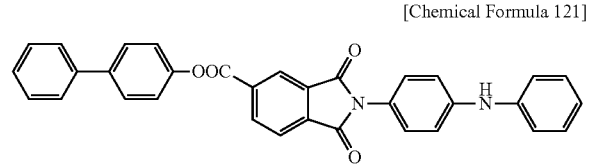

Step 1: Synthesis of Intermediate H
Intermediate H

[Chemical Formula 122]

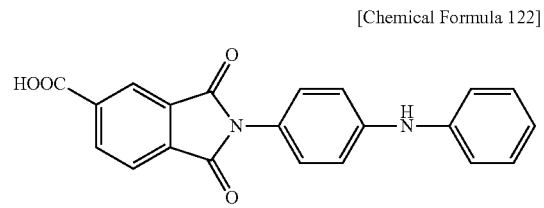 [SMILES: O=C(O)c1ccc2c(c1)C(=O)N(c1ccc(Nc3ccccc3)cc1)C2=O]

In a four-necked reactor equipped with a cooler and a thermometer, 80 g (0.42 mol) of trimellitic anhydride and 76.7 g (0.42 mol) of 4-aminodiphenylamine were dissolved in a liter of acetic acid under a nitrogen gas stream. This solution was allowed to react while heated to reflux for 10 hours in an oil bath. After completion of the reaction, the reaction liquid was poured into two liters of water, and thereby, a solid was precipitated. Thereafter, the precipitated solid was suction filtered. The filter cake was washed sequentially with water and methanol, and then was dried in a vacuum dryer. Thus, 138.5 g of a yellow-green solid was obtained (yield: 92%).

The structure was identified by $^1$H-NMR. $^1$H-NMR (500 MHz, THF-d8, TMS, δ ppm): 6.97 (t, 1H, J=7.0 Hz), 7.24-7.28 (m, 4H), 7.33-7.36 (m, 2H), 7.40-7.42 (m, 2H), 7.68 (s, 1H), 8.11 (d, 1H, J=8.5 Hz), 8.56-8.58 (m, 2H), 12.20 (bs, 1H).

Step 2: Synthesis of Compound 10

In a four-necked reactor equipped with a cooler, a thermometer and a dropping funnel, 10 g (0.028 mol) of the Intermediate H, 5.7 g (0.033 mol) of 4-hydroxybiphenyl, and 400 mg (0.0033 mol) of N,N-dimethylaminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for 14 hours at room temperature. After completion of the reaction, the reaction liquid was poured into 1.5 liters of water, and a solid was precipitated. The precipitated solid was suction filtered. The solid thus obtained was dissolved again in 100 ml of N-methylpyrrolidone, and the solution was slowly poured into a liter of methanol to precipitate a solid. The solid thus precipitated was suction filtered, and the filter cake was washed with methanol. Furthermore, the solid thus obtained was dissolved again in 100 ml of N-methylpyrrolidone, and the solution was slowly poured into a liter of methanol to precipitate a solid. The solid thus precipitated was suction filtered, and the filter cake was washed with methanol. The filter cake thus obtained was dried in a vacuum dryer, and thus 12.1 g of a yellow solid was obtained (yield: 85%). The structure was identified by $^1$H-NMR. $^1$H-NMR (500 MHz, DMF-d7, TMS, δ ppm): 6.92 (t, 1H, J=7.5 Hz), 7.25 (d, 2H, J=7.5 Hz), 7.29-7.33 (m, 4H), 7.41-7.44 (m, 3H), 7.52 (t, 2H, J=8.0 Hz), 7.57 (d, 2H, J=9.0 Hz), 7.77 (dd, 2H, J=1.0 Hz, 8.5 Hz), 7.87 (d, 2H, J=11.5 Hz), 8.22 (d, 1H, J=13.5 Hz), 8.49 (s, 1H), 8.58-8.59 (m, 1H), 8.71 (dd, 1H, J=1.5 Hz, 7.5 Hz).

(Method of Synthesizing Compound 11)
Compound 11

[Chemical Formula 123]

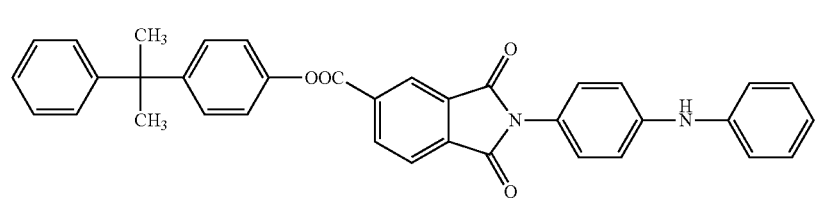

Step 1: Synthesis of Intermediate H
The Intermediate H was synthesized in the same manner as in Step 1 for the Compound 10.
Step 2: Synthesis of Compound 11

Synthesis was carried out in the same manner as in Step 2 of the synthesis of Compound 10, except that 4-hydroxybiphenyl used in the Step 2 was replaced with an equal mole number of 4-α-cumylphenol, and thus a yellow-green solid was obtained (yield: 81%). The structure was identified by $^1$H-NMR. $^1$H-NMR (500 MHz, CDCl$_3$, TMS, δ ppm): 1.71

(s, 6H), 7.00 (t, 1H, J=7.0 Hz), 7.12-7.33 (m, 18H), 8.07 (dd, 1H, J=0.5 Hz, 8.0 Hz), 8.60 (dd, 1H, J=1.5 Hz, 8.0 Hz), 8.72-8.73 (m, 1H).

(Method of Synthesizing Compound 12)
Compound 12

[Chemical Formula 124]

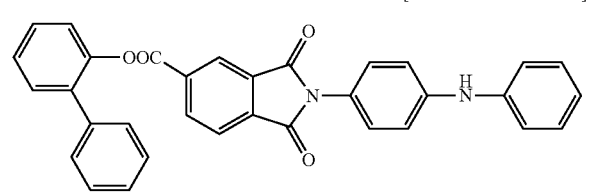

Step 1: Synthesis of Intermediate H
The Intermediate H was synthesized in the same manner as in Step 1 for the Compound 10.

Step 2: Synthesis of Compound 12
In a four-necked reactor equipped with a cooler, a thermometer and a dropping funnel, 10 g (0.028 mol) of the Intermediate H, 5.7 g (0.033 mol) of 2-phenylphenol, and 400 mg (0.0033 mol) of N,N-dimethylaminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for 12 hours at room temperature. After completion of the reaction, the reaction liquid was poured into two liters of a solvent mixture of water/methanol=1:1, and a solid was precipitated. The solid thus precipitated was suction filtered. The solid thus obtained was purified by silica gel column chromatography (toluene:ethyl acetate=9:1), and thus 10.7 g of an orange-colored solid was obtained (yield: 75%). The structure was identified by $^1$H-NMR. $^1$H-NMR (500 MHz, DMF-d7, TMS, δ ppm): 5.88 (s, 1H), 6.99 (t, 1H, J=7.5 Hz) 7.13-7.15 (m, 4H), 7.25-7.50 (m, 13H), 7.98 (d, 1H, J=8.0 Hz), 8.40 (dd, 1H, J=1.5 Hz, 7.5 Hz), 8.54-8.55 (m, 1H).

(Method of Synthesizing Compound 13)
Compound 13

[Chemical Formula 125]

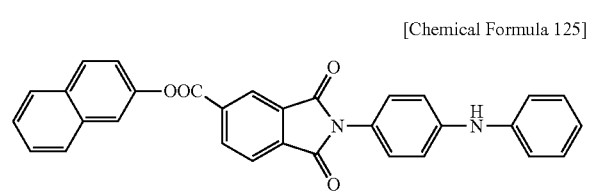

Step 1: Synthesis of Intermediate H
The Intermediate H was synthesized in the same manner as in Step 1 for the Compound 10.

Step 2: Synthesis of Compound 13
In a four-necked reactor equipped with a cooler, a thermometer and a dropping funnel, 10 g (0.028 mol) of the Intermediate H, 4.8 g (0.033 mol) of 2-naphthol, and 400 mg (0.0033 mol) of N,N-dimethylaminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for 12 hours at room temperature. After completion of the reaction, the reaction liquid was poured into 1.5 liters of methanol, and a solid was precipitated. The solid thus precipitated was suction filtered. The solid thus obtained was purified by silica gel column chromatography (toluene:ethyl acetate=9:1), and thus 7.4 g of a green solid was obtained (yield: 55%). The structure was identified by $^1$H-NMR. $^1$H-NMR (500 MHz, DMF-d7, TMS, δ ppm): 6.93 (t, 1H, J=7.0 Hz) 7.24-7.33 (m, 6H), 7.43 (d, 2H, J=8.5 Hz), 7.58-7.66 (m, 3H), 8.01-8.07 (m, 3H), 8.13 (d, 1H, J=9.0 Hz), 8.24 (d, 1H, J=8.0 Hz), 8.49 (s, 1H), 8.62 (d, 1H, J=1.0 Hz), 8.74 (dd, 1H, J=1.5 Hz, 8.0 Hz).

(Method of Synthesizing Compound 14)
Compound 14

[Chemical Formula 126]

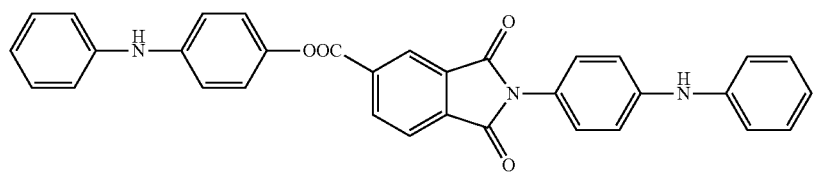

Step 1: Synthesis of Intermediate H
The Intermediate H was synthesized in the same manner as in Step 1 for the Compound 10.

Step 2: Synthesis of Compound 14
Synthesis was carried out in the same manner as in Step 2 of the synthesis of Compound 13, except that 2-naphthol used in the Step 2 was replaced with an equal mole number of 4-hydroxydiphenylamine, and thus a yellow-green solid was obtained (yield: 45%). The structure was identified by $^1$H-NMR. $^1$H-NMR (500 MHz, DMF-d7, TMS, δ ppm): 6.84 (t, 1H, J=7.0 Hz), 6.93 (t, 1H, J=7.0 Hz), 7.21 (d, 2H, J=7.0 Hz), 7.24-7.34 (m, 12H), 7.42 (d, 2H, J=7.0 Hz), 8.21 (d, 1H, J=8.0 Hz), 8.32 (s, 1H), 8.49 (s, 1H), 8.55 (s, 1H), 8.67 (dd, 1H, J=1.0 Hz, 7.5 Hz).

(Method of Synthesizing Compound 15)
Compound 15

[Chemical Formula 127]

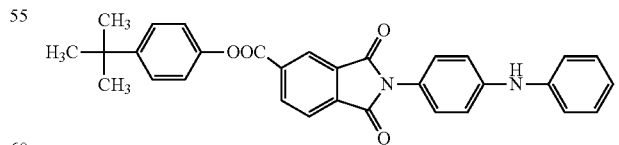

Step 1: Synthesis of Intermediate H
The Intermediate H was synthesized in the same manner as in Step 1 for the Compound 10.

Step 2: Synthesis of Compound 15
In a four-necked reactor equipped with a cooler, a thermometer and a dropping funnel, 10 g (0.028 mol) of the Intermediate H, 5.0 g (0.033 mol) of 4-tertiary-butylphenol, and 400 mg (0.0033 mol) of N,N-dimethylaminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for 20 hours at room temperature. After completion of the reaction, the reaction liquid was poured into two liters of a solvent mixture of water:methanol=1:1, and a solid was precipitated. The solid thus precipitated was suction filtered. The solid thus obtained was dissolved again in 100 ml of N-methylpyrrolidone, and the solution was slowly poured into two liters of a solvent mixture of water:methanol=1:1 to precipitate a solid. The solid thus precipitated was suction filtered, and the filter cake was washed with methanol. The solid thus obtained was purified by silica gel column chromatography (toluene:ethyl acetate=9:1), and thus 5.9 g of a yellow-green solid was obtained (yield: 43%). The structure was identified by $^1$H-NMR. $^1$H-NMR (500 MHz, DMSO-d6, TMS, δ ppm): 1.30 (s, 9H), 6.89 (t, 1H, J=7.5 Hz), 7.15-7.19 (m, 4H), 7.28-7.31 (m, 6H), 7.51 (d, 2H, J=9.0 Hz), 8.16 (d, 1H, J=7.5 Hz), 8.44 (s, 1H), 8.47 (s, 1H), 8.58 (dd, 1H, J=1.0 Hz, 7.5 Hz).

(Method of Synthesizing Compound 16)
Compound 16

[Chemical Formula 128]

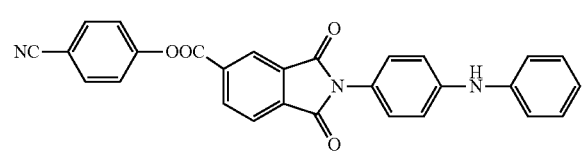

Step 1: Synthesis of Intermediate H

The Intermediate H was synthesized in the same manner as in Step 1 for the Compound 10.

Step 2: Synthesis of Compound 16

In a four-necked reactor equipped with a cooler, a thermometer and a dropping funnel, 10 g (0.028 mol) of the Intermediate H, 3.9 g (0.033 mol) of 4-cyanophenol, and 400 mg (0.0033 mol) of N,N-dimethylaminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for 18 hours at room temperature. After completion of the reaction, the reaction liquid was poured into 1.5 liters of methanol, and a solid was precipitated. The solid precipitated was suction filtered. The solid thus obtained was dissolved again in 100 ml of N-methylpyrrolidone, and the solution was slowly poured again into a liter of methanol to precipitate a solid. The precipitated solid was suction filtered, and the filter cake was washed with methanol. The solid thus obtained was purified by silica gel column chromatography (toluene:ethyl acetate=9:1), and thus 9.9 g of an orange-colored solid was obtained (yield: 77%). The structure was identified by $^1$H-NMR. $^1$H-NMR (500 MHz, DMSO-d6, TMS, δ ppm): 6.89 (t, 1H, J=7.5 Hz), 7.14-7.19 (m, 4H), 7.27-7.31 (m, 4H), 7.66 (d, 2H, J=9.0 Hz), 8.03 (d, 2H, J=9.0 Hz), 8.17 (d, 1H, J=8.0 Hz), 8.43 (s, 1H), 8.51 (d, 1H, J=1.0 Hz), 8.60 (dd, 1H, J=1.0 Hz, 7.5 Hz).

(Method of Synthesizing Compound 17)
Compound 17

[Chemical Formula 129]

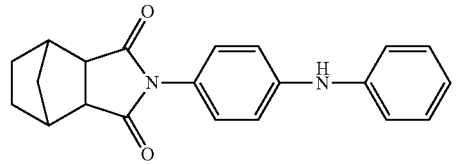

Step 1: Synthesis of Intermediate I
Intermediate I

[Chemical Formula 130]

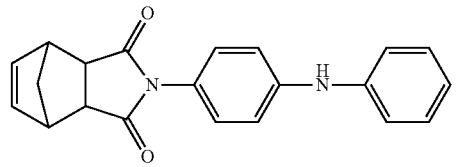

In a four-necked reactor equipped with a cooler and a thermometer, 10 g (0.061 mol) of 5-norbornene-2,3-dicarboxylic acid anhydride and 11.2 g (0.061 mol) of 4-aminodiphenylamine were dissolved in 500 ml of acetic acid under a nitrogen gas stream. This solution was allowed to react while heated to reflux for six hours in an oil bath. After completion of the reaction, the reaction liquid was poured into a liter of water, and a solid was precipitated. Thereafter, the precipitated solid was suction filtered. The filter cake was washed with water, and then the solid of the filter cake thus obtained, and 250 ml of methanol were introduced into a three-necked reactor equipped with a cooler and a thermometer. The mixture was heated to reflux for an hour in a nitrogen gas stream, and then 125 ml of water was added thereto. The mixture was cooled to 0° C., and thereby, crystals were precipitated. The precipitated crystals were suction filtered. Thereafter, the crystals of the filter cake were rinsed with a solvent mixture of methanol/water=2/1. The crystals thus obtained were dried in a vacuum dryer, and thus 18.3 g of a colorless solid was obtained (yield: 91%). The structure was identified by $^1$H-NMR. $^1$H-NMR (500 MHz, DMSO-d6, TMS, δ ppm): 1.57-1.61 (m, 2H), 3.31-3.33 (m, 2H), 3.45 (dd, 2H, J=1.8 Hz, 2.5 Hz), 6.26 (t, 2H, J=1.8 Hz), 6.86 (t, 1H, J=7.5 Hz), 6.92 (d, 2H, J=9.0 Hz), 7.07 (d, 2H, J=9.0 Hz), 7.09 (d, 2H, J=8.5 Hz), 7.24 (dd, 2H, J=7.5 Hz, 8.5 Hz), 8.35 (s, 1H).

Step 2: Synthesis of Compound 17

In a four-necked reactor equipped with a cooler and a thermometer, 10.0 g (0.03 mol) of the Intermediate I, and 1 g of 5% palladium-carbon (STD product, water-containing product, manufactured by N.E. Chemcat Corp.) were added to 300 ml of a solvent mixture of tetrahydrofuran/methanol=2/1 under a nitrogen gas stream. Under a slight pressure of hydrogen gas, the mixture was allowed to react for 16 hours at room temperature. After completion of the reaction, the reaction liquid was suction filtered with a Kiriyama funnel covered with a filtering aid. The solvent of the filtrate thus obtained was distilled off in a rotary evaporator. The solid thus obtained was purified by silica gel column chromatography (hexane:tetrahydrofuran=3:2), and thus a pale yellow solid was obtained. Furthermore, the pale yellow solid thus obtained was subjected to recrystallization from toluene, and thus 7.3 g of colorless crystals were obtained (yield: 73%).

The structure was identified by $^1$H-NMR. $^1$H-NMR (500 MHz, CDCl$_3$, TMS, δ ppm): 1.44-1.48 (m, 2H), 1.64-1.73 (m, 4H), 2.83-2.89 (m, 2H), 3.20-3.25 (m, 2H), 5.88 (s, 1H), 6.98 (t, 1H, J=7.5 Hz), 7.09-7.12 (m, 6H), 7.28 (dd, 2H, J=7.5 Hz, 8.5 Hz).

(Method of Synthesizing Compound 18)
Compound 18

[Chemical Formula 131]

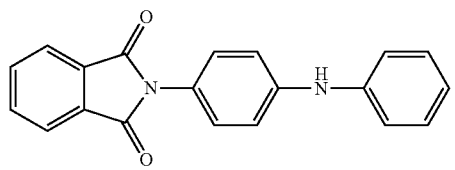

In a four-necked reactor equipped with a cooler and a thermometer, 10 g (0.068 mol) of phthalic anhydride, 12.4 g (0.068 mol) of 4-aminodiphenylamine, and 500 ml of acetic acid were introduced under a nitrogen gas stream, and the mixture was allowed to react while heated to reflux for eight hours in an oil bath. After completion of the reaction, the reaction liquid was poured into a liter of methanol, and a solid was precipitated. Thereafter, the precipitated solid was suction filtered. The solid thus obtained was dissolved again in 100 ml of N-methylpyrrolidone, and the solution was slowly poured again into a liter of methanol to precipitate a solid. The solid was dried in a vacuum dryer, and thus 19.2 g of a green solid was obtained (yield: 91%). The structure was identified by $^1$H-NMR. $^1$H-NMR (500 MHz, THF-d8, TMS, δ ppm): 6.88 (t, 1H), 7.13-7.17 (m, 4H), 7.25-7.29 (m, 4H), 7.93 (dd, 2H, J=3.0 Hz, 33.5 Hz), 7.93 (dd, 2H, J=3.0 Hz, 22.5 Hz), 8.41 (s, 1H).

(Method of Synthesizing Compound 19)
Compound 19

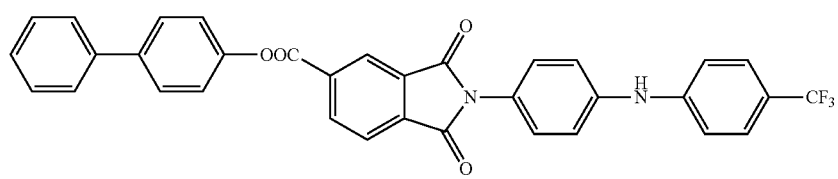

Step 1: Synthesis of Intermediate J
Intermediate J

[Chemical Formula 133]

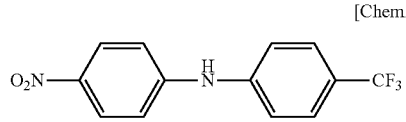

In a two-necked reactor, 40.00 g (147.1 mmol) of 4-iodobenzotrifluoride, and 30.47 g (220.6 mmol) of 4-nitroaniline were dissolved in 150 ml of dimethyl sulfoxide under a nitrogen gas stream. 11.70 g (147.1 mmol) of copper(II) oxide and 12.38 g (220.6 mmol) of potassium hydroxide were added to the solution, and the mixture was allowed to react for eight hours at 110° C. Thereafter, the reaction liquid was returned to room temperature, 1000 ml of distilled water and 500 ml of saturated brine were added thereto, and the mixture was extracted with 500 ml of ethyl acetate. The organic layer was dried over sodium sulfate, concentrated in a rotary evaporator, and then purified by silica gel column chromatography (toluene:tetrahydrofuran=9:1). Thus, 18.20 g of an Intermediate J was obtained (yield 44%). The structure was identified by $^1$H-NMR. $^1$H-NMR (500 MHz, CDCl$_3$, TMS, δ ppm): 6.47 (s, 1H), 7.09 (d, 2H, J=9.0 Hz), 7.27 (d, 2H, J=8.5 Hz), 7.62 (d, 2H, J=8.5 Hz), 8.18 (d, 2H, J=9.0 Hz).

Step 2: Synthesis of Intermediate K
Intermediate K

[Chemical Formula 134]

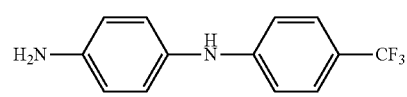

In a three-necked reactor, 17.15 g (60.76 mmol) of the Intermediate J was introduced and dissolved in 600 ml of methanol. 3.77 g of 5% palladium-carbon (STD product, water-containing product, manufactured by N.E. Chemcat Corp.) was added to the solution, and under a slight hydrogen pressure, the solution was allowed to react for five hours. Thereafter, the reaction liquid was filtered with a Kiriyama funnel covered with a filtering aid. The filtrate was concentrated in a rotary evaporator, and a solid thus obtained was purified by silica gel column chromatography (toluene:ethyl acetate=4:1). Thus, 13.84 g of an Intermediate K was obtained (yield 90%). The structure was identified by $^1$H-NMR. $^1$H-NMR (500 MHz, CDCl$_3$, TMS, δ ppm): 3.63 (s, 2H), 5.65 (s, 1H), 6.69 (d, 2H, J=9.0 Hz), 6.79 (d, 2H, J=8.5 Hz), 6.99 (d, 2H, J=9.0 Hz), 7.38 (d, 2H, J=8.5 Hz).

[Chemical Formula 132]

Step 3: Synthesis of Intermediate L
Intermediate L

[Chemical Formula 135]

In a three-necked reactor equipped with a thermometer, 16.17 g (94.98 mmol) of 4-phenylphenol and 7.51 g (94.98 mmol) of pyridine were dissolved in 200 ml of tetrahydrofuran under a nitrogen gas stream. Thereafter, 20 g (94.98 mmol) of trimellitic anhydride chloride was added thereto slowly such that the temperature of the reaction liquid would not rise to 40° C. or higher. The mixture was allowed to react for two hours at room temperature, and 800 ml of methanol was added thereto. Crystals precipitated therefrom were filtered and rinsed with methanol. The crystals thus obtained were dried in a vacuum, and thereby 21.18 g of an Intermediate L was obtained as a white solid (yield 65%). The structure was identified by $^1$H-NMR. $^1$H-NMR (500 MHz, DMSO-d6, TMS, δ ppm): 7.40 (t, 1H, J=7.5 Hz), 7.47-7.51 (m, 4H), 7.70-7.73 (m, 2H), 7.80 (d, 2H, J=9.0 Hz), 8.30 (dd, 1H, J=1.5 Hz, 8.0 Hz), 8.64 (m, 1H), 8.67 (dd, 1H, J=1.5 Hz, 8.0 Hz).

Step 4: Synthesis of Compound 19

In a two-necked reactor, 8.0 g (31.47 mmol) of the Intermediate K, and 13.0 g (37.76 mmol) of the Intermediate L were dissolved in 250 ml of acetic acid under a nitrogen gas stream. The solution was allowed to react for an hour at room temperature, and then for another three hours under heating and reflux conditions. Subsequently, the reaction liquid was returned to room temperature, and 500 ml of methanol was added thereto. Crystals precipitated therefrom were filtered, and the crystals thus obtained were added to 200 g of 1-methyl-2-pyrrolidone. The mixture was heated to 100° C. to completely dissolve the crystals. 400 g of a solvent mixture of methanol:ethyl acetate=1:1 was added to the homogeneous solution, and crystals precipitated therefrom were filtered and dried in a vacuum. Thus, 18.35 g of Compound 19 was obtained as a pale yellow solid (yield 86%). The structure was identified by $^1$H-NMR. $^1$H-NMR (500 MHz, DMSO-d6, TMS, δ ppm): 7.25 (d, 2H, J=8.5 Hz), 7.32 (d, 2H, J=8.5 Hz), 7.38-7.43 m, 3H), 7.48-7.52 (m, 4H), 7.57 (d, 2H, J=9.0 Hz), 7.72 (d, 2H, J=7.0 Hz), 7.80 (d, 2H, J=8.5 Hz), 8.19 (dd, 1H, J=1.0 Hz, 8.0 Hz), 8.53 (dd, 1H, J=1.0 Hz, 1.5 Hz), 8.63 (dd, 1H, J=1.5 Hz, 8.0 Hz), 8.94 (s, 1H).

(Method of Synthesizing Compound 20)
Compound 20

[Chemical Formula 136]

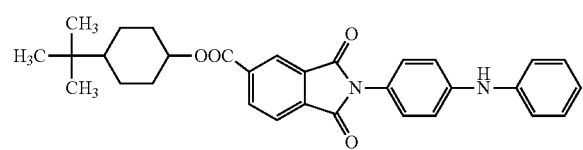

Step 1: Synthesis of Intermediate H

The Intermediate H was synthesized in the same manner as in Step 1 for the Compound 10.

Step 2: Synthesis of Compound 20

In a four-necked reactor equipped with a cooler, a thermometer and a dropping funnel, 10 g (0.028 mol) of the Intermediate H, 4.36 g (0.028 mol) of 4-tertiary-butyl-cyclohexanol, and 400 mg (0.0033 mol) of N,N-dimethylaminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for four hours at room temperature. After completion of the reaction, the reaction liquid was poured into a solvent mixture of water/methanol=1:1, and a solid was precipitated. The solid thus precipitated was suction filtered. The solid thus obtained was purified by silica gel column chromatography (toluene:ethyl acetate=9:1), and thus 9.5 g of a yellow-green solid was obtained (yield: 68%). The structure was identified by $^1$H-NMR. $^1$H-NMR (500 MHz, DMSO-d6, TMS, δppm): 8.43-8.40 (m, 2H), 8.29 (m, 1H), 8.12-8.08 (m, 1H), 7.29-7.25 (m, 4H), 7.18-7.14 (m, 4H), 6.89 (t, 1H, J=7.5 Hz), 5.23 (s, 0.4H), 4.90-4.83 (m, 0.6H), 2.14-2.03 (m, 2H), 1.84-1.82 (m, 1H), 1.66-1.60 (m, 2H), 1.53-1.46 (m, 1H), 1.40-1.32 (m, 1H), 1.23-1.04 (m, 2H), 0.89 (s, 3.6H), 0.87 (s, 5.4H).

(Method of Synthesizing Compound 21)
Compound 21

[Chemical Formula 137]

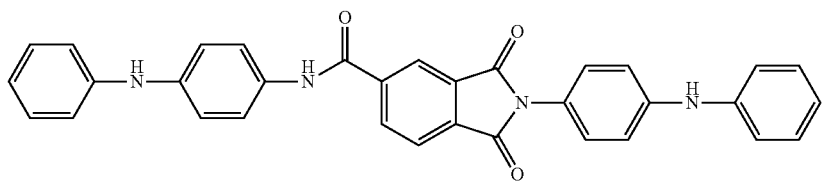

Step 1: Synthesis of Intermediate H

The Intermediate H was synthesized in the same manner as in Step 1 for the Compound 10.

Step 2: Synthesis of Compound 12

In a four-necked reactor equipped with a cooler, a thermometer and a dropping funnel, 10 g (0.028 mol) of the Intermediate H, 5.14 g (0.028 mol) of 4-aminodiphenylamine, and 400 mg (0.0033 mol) of N,N-dimethylaminopyridine were dissolved in 150 ml of N-methylpyrrolidone under a nitrogen gas stream. 6.4 g (0.033 mol) of 1-ethyl-3-(3-dimethylaminopropyl)carbodiimide hydrochloride (WSC) was added to the solution at room temperature. Thereafter, the mixture was allowed to react for 16 hours at room temperature. After completion of the reaction, the reaction liquid was poured into 1.5 liters of methanol, and a solid was precipitated. The solid thus precipitated was suction filtered. Furthermore, the solid thus obtained was dissolved in N-methylpyrrolidone. The solution was poured into 1.5 liters of methanol, and a solid was precipitated. The solid thus precipitated was purified by suction filtering. Thus, 12.1 g of a pale yellow solid was obtained (yield: 82%). The structure was identified by $^1$H-NMR. $^1$H-NMR (500 MHz, DMSO-d6, TMS, δppm): 10.50 (s, 1H), 8.52 (m, 1H), 8.44 (dd, 1H, J=1.5 Hz, 8.0 Hz), 8.43 (s, 1H), 8.16 (s, 1H), 8.10-8.09 (m, 1H), 7.70-7.68 (m, 2H), 7.31-7.26 (m, 4H), 7.24-7.21 (m, 2H), 7.19-7.14 (m, 4H), 7.12-7.09 (m, 2H), 7.07-7.05 (m, 2H), 6.91-6.87 (m, 1H), 6.82-6.79 (m, 1H).

(Method of Synthesizing Compound 22)
Compound 22

[Chemical Formula 138]

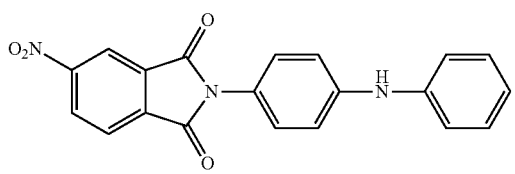

In a four-necked reactor equipped with a cooler and a thermometer, 30 g (0.155 mol) of 4-nitrophthalic anhydride, and 28.6 g (0.155 mol) of 4-aminodiphenylamine were added to a liter of acetic acid under a nitrogen gas stream. This solution was allowed to react while heated to reflux for four hours in an oil bath. After completion of the reaction, the reaction liquid was concentrated in a rotary evaporator until the reaction liquid decreased to about one-third of the original volume. The concentrated reaction liquid was poured into two liters of water. Sodium hydrogen carbonate was added to this solution until foaming stopped. Subsequently, a liter of ethyl acetate was added thereto, and the mixture was extracted. The ethyl acetate layer was partitioned, dried over anhydrous magnesium sulfate, and then filtered. The ethyl acetate layer thus obtained was concentrated in a rotary evaporator. A solid thus obtained was purified by silica gel column chromatography (toluene:ethyl acetate=9:1), and thus 41.9 g of a purple solid was obtained (yield: 75%). The structure was identified by $^1$H-NMR. $^1$H-NMR (500 MHz, DMSO-d6, TMS, δppm): 8.67 (dd, 1H, J=2.0 Hz, 8.0 Hz), 8.56 (d, 1H, J=2.0 Hz), 8.44 (s, 1H), 8.19 (d, 1H, J=8.0 Hz), 7.29-7.26 (m, 4H), 7.19-7.14 (m, 4H), 6.89 (t, 1H, J=7.0 Hz).
(Method of Synthesizing Compound 23)
Compound 23

[Chemical Formula 139]

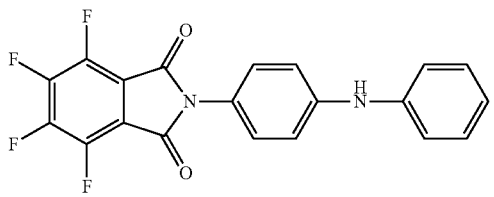

In a four-necked reactor equipped with a cooler and a thermometer, 150 ml of acetic acid was added to 10 g (0.045 mol) of tetrafluorophthalic anhydride and 8.37 g (0.045 mol) of 4-aminodiphenylamine under a nitrogen gas stream. This solution was allowed to react while heated to reflux for five hours in an oil bath. After completion of the reaction, the reaction liquid was poured into a liter of water, and thereby, a solid was precipitated. The solid thus precipitated was suction filtered. The solid thus obtained was purified by silica gel column chromatography (toluene:ethyl acetate=95:5), and 11.8 g of a yellow solid was obtained (yield: 68%). The structure was identified by $^1$H-NMR. $^1$H-NMR (500 MHz, DMSO-d6, TMS, δppm): 8.45 (s, 1H), 7.30-7.26 (m, 2H), 7.24-7.22 (m, 2H), 7.18-7.14 (m, 4H), 6.90 (t, 1H, J=7.5 Hz).
(Method of Synthesizing Compound 24)
Compound 24

[Chemical Formula 140]

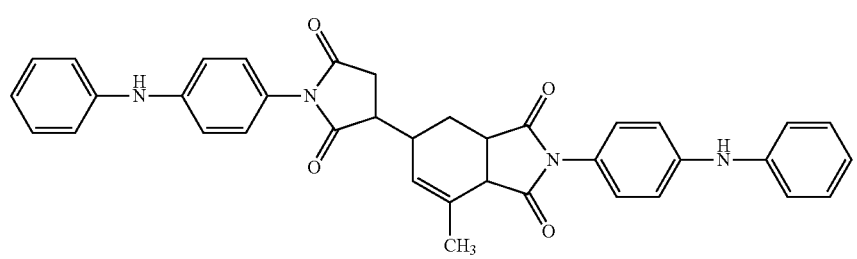

In a four-necked reactor equipped with a cooler and a thermometer, a liter of acetic acid was added to 20 g (0.076 mol) of 5-(2,5-dioxotetrahydrofuryl)-3-methyl-3-cyclohexene-1,2-dicarboxylic acid anhydride and 27.9 g (0.152 mol) of 4-aminodiphenylamine under a nitrogen gas stream. This solution was allowed to react while heated to reflux for five hours in an oil bath. After completion of the reaction, the reaction liquid was concentrated in a rotary evaporator until the reaction liquid decreased to about one-third of the original volume. The concentrated reaction liquid was poured into two liters of water. Sodium hydrogen carbonate was added to this solution until foaming stopped. Subsequently, a liter of ethyl acetate was added thereto, and the mixture was extracted. The ethyl acetate layer was partitioned, dried over anhydrous magnesium sulfate, and then filtered. The ethyl acetate layer thus obtained was concentrated in a rotary evaporator. A solid thus obtained was purified by silica gel column chromatography (toluene:ethyl acetate=7:3), and thus 29.5 g of a pale yellow solid was obtained (yield: 65%). The structure was identified by $^1$H-NMR. $^1$H-NMR (500 MHz, DMSO-d6, TMS, δppm): 8.36 (s, 1H), 8.35 (s, 1H), 7.28-7.23 (m, 4H), 7.18-7.11 (m, 10H), 7.05 (d, 2H, J=9.0 Hz), 6.87 (t, 2H, J=7.0 Hz), 5.50 (s, 1H), 3.55-3.50 (m, 2H), 3.17-3.14 (m, 1H), 2.93-2.87 (m, 1H), 2.58-2.56 (m, 1H), 2.50-2.43 (m, 2H), 2.35-2.32 (m, 1H), 1.95 (s, 3H).
(Method of Synthesizing Compound 25)
Compound 25

[Chemical Formula 141]

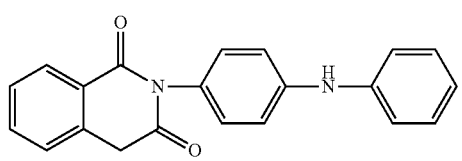

In a four-necked reactor equipped with a cooler and a thermometer, 150 ml of acetic acid was added to 10 g (0.056 mol) of homophthalic acid and 10.23 g (0.056 mol) of 4-aminodiphenylamine under a nitrogen gas stream. This solution was allowed to react while heated to reflux for five hours in an oil bath. After completion of the reaction, the reaction liquid was concentrated in a rotary evaporator until the reaction liquid decreased to about one-third of the original volume. The concentrated reaction liquid was poured into a liter of water. Sodium hydrogen carbonate was added to this solution until foaming stopped. Subsequently, 500 ml of ethyl acetate was added thereto, and the mixture was extracted. The ethyl acetate layer was partitioned, dried over anhydrous magnesium sulfate, and then filtered. The ethyl acetate layer thus obtained was concentrated in a rotary evaporator. A solid thus obtained was purified by silica gel column chromatography (toluene:ethyl acetate=8:2), and thus 13 g of a pale gray solid was obtained (yield: 71%). The structure was identified by $^1$H-NMR. $^1$H-NMR (400 MHz, DMSO-d6, TMS, δppm): 8.31 (s, 1H), 8.02 (d, 1H, J=8.2 Hz), 7.66 (t, 1H, J=7.3 Hz), 7.48-7.41 (m, 2H), 7.23 (t, 2H, J=7.8 Hz), 7.11-7.01 (m, 6H), 6.83 (t, 1H, J=7.9 Hz), 4.23 (s, 2H).

5. Examples Involving Compounds 10 to 25 and Comparative Examples

Examples 14 to 31 for the diarylamine compounds 10 to 25 represented by the formula (III) of the present invention, which were synthesized in the Production Examples, and Comparative Examples 10 to 19 will be described.

Hereinafter, evaluations of rubber composition in which the diarylamine compounds represented by the formula (III) of the present invention as aging inhibitors for acrylic rubber is used, will be described by way of Examples. However, the present invention is not intended to be limited to these Examples. In the following descriptions, the units "parts" and "percent (%)" are on a weight basis unless particularly stated otherwise. The preparation of test specimens and the evaluation method for heat resistance are similar to those described in connection with the diarylamine compound represented by any one of the formulas (I) and (II) of the present invention. In addition, rubber compositions were prepared, without adding an aging inhibitor in Comparative Example 10, and by adding conventionally known diphenylamine-based aging inhibitors in Comparative Examples 11 to 19.

Discussion on Examples and Comparative Examples

The results of the evaluation of heat resistance are presented in Table 7 (Examples) and Table 8 (Comparative Examples).

TABLE 7

| Incorporated formulation | | | Ex. 14 | Ex. 15 | Ex. 16 | Ex. 17 | Ex. 18 | Ex. 19 |
|---|---|---|---|---|---|---|---|---|
| | AR22 | pts. wt.$^{(1*)}$ | 100 | 100 | 100 | 100 | 100 | 100 |
| | SEAST SO | pts. wt. | 60 | 60 | 60 | 60 | 60 | 60 |
| | Stearic acid | pts. wt. | 2 | 2 | 2 | 2 | 2 | 2 |
| Aging inhibitor | Type | | Cpd.$^{(*2)}$ 10 | | | Cpd. 11 | Cpd. 12 | Cpd. 13 |
| | Addition amount relative to 100 parts by weight of rubber (AR22) | pts. wt. | 2.52 | 5.03 | 7.55 | 2.72 | 2.52 | 2.39 |
| | Addition amount relative to 100 g of rubber (AR22) | mmol | 4.93 | 9.86 | 14.79 | 4.93 | 4.93 | 4.93 |
| | DIAK No. 1 | pts. wt. | 0.5 | 0.5 | 0.5 | 0.5 | 0.5 | 0.5 |
| | NOCCELER DT | pts. wt. | 2.0 | 2.0 | 2.0 | 2.0 | 2.0 | 2.0 |
| | Elongation at break (before test) | % | 260 | 260 | 260 | 250 | 270 | 260 |
| | Elongation change ratio after a lapse of time for 504 hours at 190° C. | % | 74 | 68 | 65 | 78 | 77 | 79 |

| Incorporated formulation | | | Ex. 20 | Ex. 21 | Ex. 22 | Ex. 23 | Ex. 24 | Ex. 25 |
|---|---|---|---|---|---|---|---|---|
| | AR22 | pts. wt.$^{(1*)}$ | 100 | 100 | 100 | 100 | 100 | 100 |
| | SEAST SO | pts. wt. | 60 | 60 | 60 | 60 | 60 | 60 |
| | Stearic acid | pts. wt. | 2 | 2 | 2 | 2 | 2 | 2 |
| Aging inhibitor | Type | | Cpd. 14 | Cpd. 15 | Cpd. 16 | Cpd. 17 | Cpd. 18 | Cpd. 19 |
| | Addition amount relative to 100 parts by weight of rubber (AR22) | pts. wt. | 1.30 | 2.42 | 2.27 | 1.64 | 1.55 | 2.85 |
| | Addition amount relative to 100 g of rubber (AR22) | mmol | 2.47 | 4.93 | 4.93 | 4.93 | 4.93 | 4.93 |
| | DIAK No. 1 | pts. wt. | 0.5 | 0.5 | 0.5 | 0.5 | 0.5 | 0.5 |
| | NOCCELER DT | pts. wt. | 2.0 | 2.0 | 2.0 | 2.0 | 2.0 | 2.0 |
| | Elongation at break (before test) | % | 250 | 250 | 250 | 270 | 270 | 260 |

TABLE 7-continued

| | | | | | | | |
|---|---|---|---|---|---|---|---|
| Elongation change ratio after a lapse of time for 504 hours at 190° C. | % | 78 | 77 | 76 | 71 | 70 | 70 |

| Incorporated formulation | | Ex. 26 | Ex. 27 | Ex. 28 | Ex. 29 | Ex. 30 | Ex. 31 |
|---|---|---|---|---|---|---|---|
| AR22 | pts. wt. | 100 | 100 | 100 | 100 | 100 | 100 |
| SEAST SO | pts. wt. | 60 | 60 | 60 | 60 | 60 | 60 |
| Stearic acid | pts. wt. | 2 | 2 | 2 | 2 | 2 | 2 |
| Aging inhibitor Type | | Cpd. 20 | Cpd. 21 | Cpd. 22 | Cpd. 23 | Cpd. 24 | Cpd. 25 |
| Addition amount relative to 100 parts by weight of rubber (AR22) | pts. wt. | 2.45 | 1.29 | 1.77 | 1.90 | 2.94 | 1.62 |
| Addition amount relative to 100 g of rubber (AR22) | mmol | 4.93 | 2.47 | 4.93 | 4.93 | 4.93 | 4.93 |
| DIAK No. 1 | pts. wt. | 0.5 | 0.5 | 0.5 | 0.5 | 0.5 | 0.5 |
| NOCCELER DT | pts. wt. | 2.0 | 2.0 | 2.0 | 2.0 | 2.0 | 2.0 |
| Elongation at break (before test) | % | 270 | 260 | 260 | 250 | 270 | 250 |
| Elongation change ratio after a lapse of time for 504 hours at 190° C. | % | 71 | 75 | 74 | 74 | 75 | 75 |

(*1)pts. wt.: parts by weight
(*2)Cpd.: Compound

TABLE 8

| Incorporated formulation | | Comp. Ex. 10 | Comp. Ex. 11 | Comp. Ex. 12 | Comp. Ex. 13 | Comp. Ex. 14 |
|---|---|---|---|---|---|---|
| AR22 | pts. wt.(1*) | 100 | 100 | 100 | 100 | 100 |
| SEAST SO | pts. wt. | 60 | 60 | 60 | 60 | 60 |
| Stearic acid | pts. wt. | 2 | 2 | 2 | 2 | 2 |
| Aging inhibitor Type | | None | Diphenyl amine | STEARER-STAR | NONFLEX LAS-P | NOCRAC WHITE |
| Addition amount relative to 100 parts by weight of rubber (AR22) | pts. wt. | 0 | 0.84 | 1.39 | 1.50 | 1.78 |
| Addition amount relative to 100 g of rubber (AR22) | mmol | 0 | 4.93 | 4.93 | 4.93 | 4.93 |
| DIAK No. 1 | pts. wt. | 0.5 | 0.5 | 0.5 | 0.5 | 0.5 |
| NOCCELER DT | pts. wt. | 2.0 | 2.0 | 2.0 | 2.0 | 2.0 |
| Elongation at break (before test) | % | 250 | 260 | 260 | 250 | 260 |
| Elongation change ratio after a lapse of time for 504 hours at 190° C. | % | 90 | 87 | 88 | 85 | 84 |

| Incorporated formulation | | Comp. Ex. 15 | Comp. Ex. 16 | Comp. Ex. 17 | Comp. Ex. 18 | Comp. Ex. 19 |
|---|---|---|---|---|---|---|
| AR22 | pts. wt.(1*) | 100 | 100 | 100 | 100 | 100 |
| SEAST SO | pts. wt. | 60 | 60 | 60 | 60 | 60 |
| Stearic acid | pts. wt. | 2 | 2 | 2 | 2 | 2 |
| Aging inhibitor Type | | NOCRAC DP | NOCRAC AD-F | | NAUGARD 445 | |
| Addition amount relative to 100 parts by weight of rubber (AR22) | pts. wt. | 1.28 | 1.94 | 2.00 | 4.00 | 6.00 |

TABLE 8-continued

| | | | | | | |
|---|---|---|---|---|---|---|
| Addition amount relative to 100 g of rubber (AR22) | mmol | 4.93 | 4.93 | 4.93 | 9.86 | 14.79 |
| DIAK No. 1 | pts. wt. | 0.5 | 0.5 | 0.5 | 0.5 | 0.5 |
| NOCCELER DT | pts. wt. | 2.0 | 2.0 | 2.0 | 2.0 | 2.0 |
| Elongation at break (before test) | % | 270 | 260 | 260 | 270 | 280 |
| Elongation change ratio after a lapse of time for 504 hours at 190° C. | % | 85 | 83 | 80 | 78 | 79 |

[*1]pts. wt.: parts by weight

In Examples 14 to 31 in which, as the aging inhibitor, the diarylamine compounds represented by the formula (III) of the present invention which has a characteristic chemical structure and has at least one signal attributable to the hydrogen of the N—H moiety at 8.30 ppm to 9.00 ppm when a deuterated dimethyl sulfoxide solution of the diarylamine compound is analyzed by $^1$H-NMR is used, it can be seen that even under the severe conditions of standing for 504 hours in an environment at 190° C., the elongation change ratios are small, and excellent heat resistance is exhibited. Particularly, the compounds having the signal between 8.38 ppm and 8.94 ppm can realize very excellent heat resistance, such as an elongation change ratio after standing for 504 hours at 190° C. of 70% to 74%. Furthermore, in Examples 14 to 16 in which the Compound 10 is used as the aging inhibitor, it can be conceived that when the addition amount of the aging inhibitor is increased, heat resistance that is indicated by the elongation change ratio is enhanced, and also, excellent rubber elasticity is maintained without any changes in the value of the elongation at break, thereby the degree of freedom in the product design being increased.

On the contrary, in regard to Comparative Example 10 in which no aging inhibitor was not added, it is understood that the absolute value of the elongation change ratio of the acrylic rubber was large, and heat resistance was not sufficient. Furthermore, in regard to Comparative Examples 11 to 19 in which conventionally known diphenylamine-based aging inhibitors were added, it is understood that the elongation change ratio, that is, the effect of improving heat resistance was small as compared with Comparative Example 10 in which no aging inhibitor was added. Furthermore, in regard to Comparative Examples 17 to 19, it is understood that the elongation change ratio was enhanced along with an increase in the addition amount of the aging inhibitor; however, on the other hand, the elongation at break increased, so that there occurred an adverse effect that rubber was plasticized as a result of an increase in the amount of the aging inhibitor.

6. Test for Normal State Properties of Rubber Composition and Heat Resistance of Molded Article Furthermore, for the Compounds 1, 4, 8 and 9 synthesized in the Production Examples of the diarylamine compounds of the present invention, tests on the normal state properties and the heat resistance of molded articles were carried out.
I. Heat Resistance Test for Application as Extrusion Molded Articles The preparation of test specimens and the tests on various properties were carried out according to the following methods.

(Preparation of Test Specimen)
An acrylic rubber composition was molded by pressing for 20 minutes at 170° C. and crosslinked, and thus a sheet having a size of 15 cm×15 cm×2 mm was produced. Furthermore, this sheet was subjected to secondary crosslinking by heating at 170° C. for four hours. A dumbbell-shaped No. 3 test specimen was produced from this sheet.
(Test for Normal State Properties)
As the mechanical characteristics at normal temperature, the respective produced test specimens were used to measure the tensile strength, elongation at break (elongation), and 100% tensile stress according to the tensile test of JIS K6251. Furthermore, the hardness was measured according to the hardness test of JIS K6253.
(Heat Resistance Test)
A test for heat resistance for an application as extrusion molded articles was carried out using test specimens thus produced, which had been left to stand for 1000 hours in an environment at 180° C. The elongation change ratio was obtained by measuring the elongations according to JIS K6251, and calculating the change ratios (absolute values) of the elongations according to the following calculation formula. It is considered that as closer to zero the elongation change ratio is, even when the rubber composition is processed into an extrusion molded article, higher heat resistance is obtained, which leads to preferable results.
Calculation Formula:

Change ratio (%)=|100×[(elongation before test (%))− (elongation after test (%))]/(elongation before test (%))|.

Furthermore, the 100% tensile stress was measured according to JIS K6251. A tear of a test specimen in the middle of the test was evaluated as BO (bending out). Furthermore, as a bending test, a test specimen after heat resistant aging was subjected to 180° bending, and the external appearance was evaluated by observing whether there was any abnormality such as the occurrence of cracking, or folds. A test specimen having no abnormality such as the occurrence of cracking or folds was rated as A, and a test specimen having abnormalities such as the occurrence of cracking or folds was rated as B.

Examples 32 to 39, and Comparative Examples 20 and 21

100 parts by weight of an acrylic rubber (manufactured by Zeon Corp., Nipol AR22), 60 parts by weight of carbon black (manufactured by Tokai Carbon Co., Ltd., SEAST SO), 2 parts by weight of stearic acid, and as an aging inhibitor, a predetermined amount of one of Compound 1 (Examples 32 and 33), Compound 4 (Examples 34 and 35), Compound 8 (Examples 36 and 37) and Compound 9 (Examples 38 and 39), which were all synthesized in the Production Examples described above, or 4,4'-bis(α,α'-dimethylbenzyl)diphenylamine (manufactured by Shiraishi Calcium Kaisha, Ltd., NAUGARD 445: Comparative Examples 20 and 21) were mixed, and the mixture was kneaded for five minutes at 50° C. using a 0.8-liter Banbury mixer. Subsequently, 1 part by weight of 2,2-bis[4-(4-aminophenoxy)phenyl]propane (manufactured by Wakayama Seika Kogyo Co., Ltd., BAPP) as a crosslinking agent, and 2 parts by weight of dialkyl(C8-18)amine (manufactured by Lion Akzo Co., Ltd., AMINE 2C) as a crosslinking accelerating agent were added to the kneading product, and the mixture was kneaded with an open roll. Thus, an acrylic rubber composition was prepared. This acrylic rubber composition was molded and crosslinked under the conditions described above, and thereby, test specimens were produced. These test specimens were subjected to a test for normal state properties, and measurement of the elongation change ratio, a 100% tensile stress and a bending test as heat resistance tests. The results are presented in Table 9.

exhibit folds in the middle of the test, Examples 32 to 39 do not have occurrence of cracking or folds even if subjected to 180° bending. Thus, it was confirmed that the crosslinked rubber products formed by using the acrylic rubber compositions of the present invention exhibit improved heat resistance in the heat resistance test for the application as extrusion molded articles. In addition, in Examples 33, 35, 37 and 39, a further enhanced heat resistance was recognized as the content of the diarylamine compounds of the present invention increased (elongation change ratio, and 100% tensile stress). Therefore, the effect of incorporating the compounds of the present invention (Compounds 1, 4, 8 and 9) as aging inhibitors was confirmed.

II. Heat Resistance Test for Application as Sealing Member

The preparation of test specimens, and the tests on various properties were carried out according to the following methods.

An acrylic rubber composition was molded by pressing for 20 minutes at 170° C. and crosslinked, and cylindrical-shaped

TABLE 9

| Incorporated formulation | | | Ex. 32 | Ex. 33 | Ex. 34 | Ex. 35 | Ex. 36 | Ex. 37 | Ex. 38 | Ex. 39 | Comp. Ex. 20 | Comp. Ex. 21 |
|---|---|---|---|---|---|---|---|---|---|---|---|---|
| AR22 | | pts. wt.[(1*)] | 100 | 100 | 100 | 100 | 100 | 100 | 100 | 100 | 100 | 100 |
| SEAST SO | | pts. wt. | 60 | 60 | 60 | 60 | 60 | 60 | 60 | 60 | 60 | 60 |
| Stearic acid | | pts. wt. | 2 | 2 | 2 | 2 | 2 | 2 | 2 | 2 | 2 | 2 |
| Aging inhibitor | Type | | Cpd.[(*2)] 1 | | Cpd. 4 | | Cpd. 8 | | Cpd. 9 | | NAUGARD 445 | |
| | Addition amount relative to 100 parts by weight of rubber | pts. wt. | 2.52 | 5.03 | 2.39 | 4.78 | 2.85 | 5.70 | 1.64 | 3.28 | 2.00 | 4.00 |
| | Addition amount relative to 100 g of rubber | mmol | 4.93 | 9.86 | 4.93 | 9.86 | 4.93 | 9.86 | 4.93 | 9.86 | 4.93 | 9.86 |
| BAPP | | pts. wt. | 1.0 | 1.0 | 1.0 | 1.0 | 1.0 | 1.0 | 1.0 | 1.0 | 1.0 | 1.0 |
| AMINE 2C | | pts. wt. | 2.0 | 2.0 | 2.0 | 2.0 | 2.0 | 2.0 | 2.0 | 2.0 | 2.0 | 2.0 |
| Normal state properties | Tensile strength | Mpa | 9.4 | 9.4 | 9.6 | 9.5 | 9.7 | 9.5 | 9.8 | 9.6 | 9.8 | 9.4 |
| | Elongation | % | 260 | 260 | 260 | 260 | 270 | 270 | 260 | 270 | 260 | 270 |
| | 100% tensile stress | Mpa | 3.8 | 3.6 | 3.8 | 3.7 | 3.9 | 3.8 | 3.9 | 3.7 | 4.1 | 3.9 |
| | Hardness | Duro A | 64 | 34 | 63 | 64 | 64 | 63 | 63 | 63 | 64 | 64 |
| Extrusion heat resistance | Elongation change ratio, after a lapse of time for 1000 hours at 180° C. | % | 65 | 53 | 67 | 56 | 61 | 52 | 66 | 58 | 80 | 78 |
| | 100% tensile stress, after a lapse of time for 1000 hours at 180° C. | Mpa | 5.4 | 5.2 | 5.5 | 5.2 | 5.3 | 5.1 | 5.5 | 5.3 | BO | BO |
| | Bending test, after a lapse of time for 1000 hours at 180° C. | | A | A | A | A | A | A | A | A | B | B |

[(*1)]pts. wt.: parts by weight
[(*2)]Cpd.: Compound

As shown in Table 9, in Examples 32 to 39 in which the diarylamine compounds of the present invention (Compounds 1, 4, 8 and 9) are used as aging inhibitors, even under the severe conditions of standing for 1000 hours in an environment at 180° C., the changes in elongation are small as compared with Comparative examples 20 and 21. Furthermore, in regard to the 100% tensile stress, while Comparative Examples 20 and 21 undergo bending out (BO), Examples 32 to 39 do not exhibit tear of the test specimens. Furthermore, in the bending test, while Comparative Examples 20 and 21 test specimens having a diameter of 29 mm and a thickness of 12.5 mm were produced. The test specimens were subjected to secondary crosslinking by heating for four hours at 170° C. As the mechanical characteristics at normal temperature, the produced test specimens were respectively used to measure the tensile strength, elongation at break (elongation), and 100% tensile stress according to the tensile test of JIS K6251. Furthermore, the hardness was measured according to the hardness test of JIS K6253. Subsequently, the test specimens were left to stand for 168 hours in an environment at 180° C.

in a state of being 25% compressed, and then, compression was released. Thus, the compression set was measured.

Examples 40 to 43, and Comparative Example 22

100 parts by weight of an acrylic rubber (manufactured by Zeon Corp., Nipol AR12), 60 parts by weight of carbon black (manufactured by Tokai Carbon Co., Ltd., SEAST SO), 2 parts by weight of stearic acid, and as an aging inhibitor, a predetermined amount of one of Compounds 1, 4, 8 and 9 synthesized in the Production Examples described above (Examples 40 to 43), or 4,4'-bis(α,α'-dimethylbenzyl)diphenylamine (manufactured by Shiraishi Calcium Kaisha, Ltd., NAUGARD 445: Comparative Example 22) were mixed, and the mixture was kneaded for five minutes at 50° C. using a 0.8-liter Banbury mixer. Subsequently, 0.6 parts by weight of hexamethylenediamine carbamate (manufactured by DuPont Dow Elastomers Japan K.K., Diak No. 1) as a crosslinking agent, and 2 parts by weight of di-o-tolylguanidine (manufactured by Ouchi Shinko Chemical Industrial Co., Ltd., NOCCELER DT) as a crosslinking accelerating agent were added to the kneaded product, and the mixture was kneaded with an open roll. Thus, an acrylic rubber composition was prepared. This acrylic rubber composition was molded and crosslinked under the conditions described above, and thus test specimens were produced. These test specimens were subjected to a test for normal state properties, and the measurement of compression set as a heat resistance test. The results are presented in Table 10.

INDUSTRIAL APPLICABILITY

According to the present invention, there is provided a diarylamine compound having a novel structure, which can be used in an aging inhibitor that does not cause oxidative deterioration of polymers such as rubbers and polyolefin resins, even if used in a higher temperature environment than in conventional cases. Furthermore, an aging inhibitor, particularly an aging inhibitor for polymers, which contains the compound, can be provided, and a polymer composition such as a rubber composition or a polyolefin composition, which contains the compound and has high heat resistance, can be provided. Therefore, polymer materials such as rubbers and polyolefin resins can be used under severer high-temperature conditions that in conventional cases.

The invention claimed is:
1. A diarylamine compound represented by the following formula (I), the diarylamine compound having a hydrogen of the N—H moiety having a N—H shift value in $^1$H-NMR of 8.30 ppm to 9.00 ppm as measured in deuterated dimethyl sulfoxide (TMS, δ ppm):

TABLE 10

| Incorporated formulation | | Ex. 40 | Ex. 41 | Ex. 42 | Ex. 43 | Comp. Ex. 22 |
|---|---|---|---|---|---|---|
| AR22 | pts. wt.[1*] | 100 | 100 | 100 | 100 | 100 |
| SEAST SO | pts. wt. | 60 | 60 | 60 | 60 | 60 |
| Stearic acid | pts. wt. | 2 | 2 | 2 | 2 | 2 |
| Aging inhibitor Type | | Cpd.[*2] 1 | Cpd. 4 | Cpd. 8 | Cpd. 9 | NAUGARD 445 |
| Addition amount relative to 100 parts by weight of rubber | pts. wt. | 2.52 | 2.39 | 2.85 | 1.64 | 2.00 |
| Addition amount relative to 100 g of rubber | mmol | 4.93 | 4.93 | 4.93 | 4.93 | 4.93 |
| DIAK No. 1 | pts. wt. | 0.6 | 0.6 | 0.6 | 0.6 | 0.6 |
| NOCCELER DT | pts. wt. | 2.0 | 2.0 | 2.0 | 2.0 | 2.0 |
| Normal state properties Tensile strength | Mpa | 9.4 | 9.6 | 9.7 | 9.8 | 9.8 |
| Elongation | % | 250 | 260 | 240 | 260 | 240 |
| Hardness | Duro A | 64 | 63 | 64 | 63 | 64 |
| Seal heat resistance Compression set, after 168 hours at 180° C. | % | 19 | 20 | 18 | 19 | 23 |

[*1]pts. wt.: parts by weight
[*2]Cpd.: Compound

As shown in Table 10, in Examples 40 to 43 in which the diarylamine compounds of the present invention (Compounds 1, 4, 8 and 9) were used as aging inhibitors, it was confirmed that even under the severe conditions of standing for 168 hours in an environment at 180° C., the compression set was small as compared with Comparative Example 22. It was also confirmed that the crosslinked products formed by using the acrylic rubber compositions of the present invention exhibited improved heat resistance in the heat resistance test for the application as sealing members as well.

Formula (I)

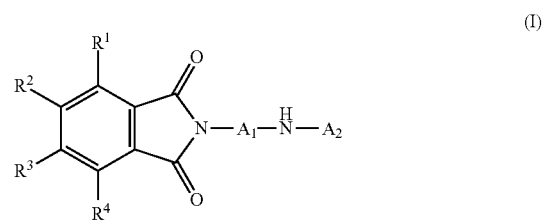

wherein in the formula (I),
- $A_1$ and $A_2$ each independently represents an aromatic group which is optionally substituted with an alkyl group having 1 to 10 carbon atoms, a halogen-substituted alkyl group having 1 to 10 carbon atoms, a halogen atom, a cyano group, or a nitro group;
- $R^1$, $R^3$ and $R^4$ each represent a hydrogen atom;
- $R^2$ represents —C(=O)—OR''', and R''' represents an alkyl group having 1 to 10 carbon atoms, or an aromatic group having 4 to 30 carbon atoms; wherein R''' is optionally substituted with a halogen atom, an alkyl group having 1 to 10 carbon atoms, an aralkyl group having 1 to 20 carbon atoms, an aromatic group having 6 to 30 carbon atoms, a cyano group, a nitro group, a sulfo group, —OR$^a$, —O—C(=O)—R$^a$, —C(=O)—OR$^a$, —O—C(=O)—OR$^a$, —NR$^c$—C(=O)—R$^a$, —C(=O)—NR$^a$R$^b$, —O—C(=O)—NR$^a$R$^b$, —SR$^a$, —S(=O)—R$^a$, or —S(=O)$_2$—R$^a$;
- $R^a$, $R^b$ and $R^c$ each independently represent a hydrogen atom, an alkyl group having 1 to 8 carbon atoms, or a phenyl group.

2. The compound according to claim 1, represented by the formula (I), wherein
- $A_1$ represents a phenylene group which is optionally substituted with an alkyl group having 1 to 10 carbon atoms, a halogen-substituted alkyl group having 1 to 10 carbon atoms, a halogen atom, a cyano group, or a nitro group;
- $A_2$ represents a phenyl group which is optionally substituted with an alkyl group having 1 to 10 carbon atoms, a halogen-substituted alkyl group having 1 to 10 carbon atoms, a halogen atom, a cyano group, or a nitro group.

3. The compound according to claim 1, represented by the formula (I), wherein
- R''' represents a phenyl group or a naphthyl group; wherein R''' is optionally substituted with a halogen atom, an alkyl group having 1 to 10 carbon atoms, an aralkyl group having 1 to 20 carbon atoms, an aromatic group having 6 to 30 carbon atoms, a cyano group, a nitro group, a sulfo group, —OR$^a$, —O—C(=O)—R$^a$, —C(=O)—OR$^a$, —O—C(=O)—OR$^a$, —NR$^c$—C(=O)—R$^a$, —C(=O)—NR$^a$R$^b$, —O—C(=O)—NR$^a$R$^b$, —SR$^a$, —S(=O)—R$^a$, or —S(=O)$_2$—R$^a$;
- $R^a$, $R^b$ and $R^c$ each independently represent a hydrogen atom, an alkyl group having 1 to 8 carbon atoms, or a phenyl group.

4. An aging inhibitor for polymers comprising the compound according to claim 1.

5. A polymer composition comprising the compound according to claim 1, and a polymer.

6. A method of producing a diarylamine compound represented by the following formula (VII), which has a hydrogen of the N—H moiety having a N—H shift value in $^1$H-NMR of 8.30 ppm to 9.00 ppm as measured in deuterated dimethyl sulfoxide (TMS, δ ppm):

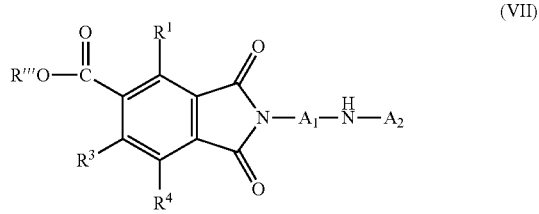

(VII)

wherein in the formula (VII),
- $A_1$ and $A_2$ each independently represents an aromatic group which is optionally substituted with an alkyl group having 1 to 10 carbon atoms, a halogen-substituted alkyl group having 1 to 10 carbon atoms, a halogen atom, a cyano group, or a nitro group;
- $R^1$, $R^3$ and $R^4$ each represent a hydrogen atom;
- $R^2$ represents —C(=O)—OR''', and R''' represents an alkyl group having 1 to 10 carbon atoms, or an aromatic group having 4 to 30 carbon atoms; wherein R''' is optionally substituted with a halogen atom, an alkyl group having 1 to 10 carbon atoms, an aralkyl group having 1 to 20 carbon atoms, an aromatic group having 6 to 30 carbon atoms, a cyano group, a nitro group, a sulfo group, —OR$^a$, —O—C(=O)—R$^a$, —C(=O)—OR$^a$, —O—C(=O)—OR$^a$, —NR$^c$—C(=O)—R$^a$, —C(=O)—NR$^a$R$^b$, —O—C(=O)—NR$^a$R$^b$, —SR$^a$, —S(=O)—R$^a$, or —S(=O)$_2$—R$^a$,
- $R^a$, $R^b$ and $R^c$ each independently represent a hydrogen atom, an alkyl group having 1 to 8 carbon atoms, or a phenyl group, the method comprising three processes, comprising Process 1 of allowing a trimellitic anhydride halide compound represented by the following formula (IV):

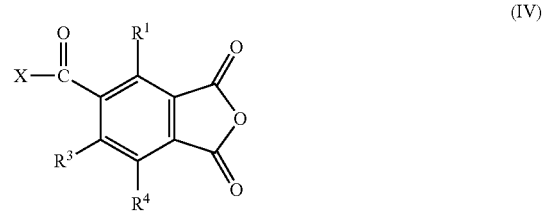

(IV)

wherein in the formula (IV),
- $R^1$, $R^3$ and $R^4$ represent a hydrogen atom; and
- X represents a halogen atom, to react with a hydroxyl group-containing compound represented by the following formula (V):

R'''OH                                    (V)

wherein in the formula (V),
- R''' represents an alkyl group having 1 to 10 carbon atoms which may have a substituent, or an aromatic group having 4 to 30 carbon atoms which may have a substituent;
- the relevant substituents are each independently a halogen atom, an alkyl group having 1 to 10 carbon atoms, an aralkyl group having 1 to 20 carbon atoms, an aromatic group having 6 to 30 carbon atoms, a cyano group, a nitro group, a sulfo group, —OR$^a$, —O—C(=O)—R$^a$, —C(=O)—OR$^a$, —O—C(=O)—OR$^a$, —NRc—C(=O)—R$^a$, —C(=O)—NR$^a$R$^b$, —O—C(=O)—NR$^a$R$^b$, —SR$^a$, —S(=O)—R$^a$ or —S(=O)$_2$—R$^a$; and
- $R^a$, $R^b$ and $R^c$ each independently represent a hydrogen atom, an alkyl group having 1 to 8 carbon atoms, or a phenyl group, in an organic solvent in the presence of a base, and thereby producing a trimellitic anhydride ester compound by the following reaction scheme (1):

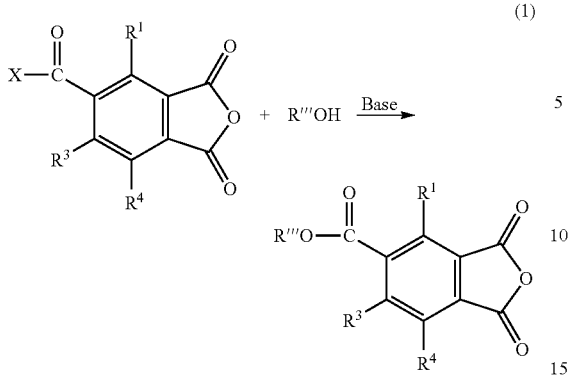

(1)

wherein the symbols used in the reaction scheme (1) respectively have the same meanings as defined above;

Process 2 of allowing the trimellitic anhydride ester compound produced in Process 1 to react with an amino group-containing diarylamine compound represented by the following formula (VI):

(VI)

wherein in the formula (VI), $A_1$ and $A_2$ each independently represents an aromatic group which is optionally substituted with an alkyl group having 1 to 10 carbon atoms, a halogen-substituted alkyl group having 1 to 10 carbon atoms, a halogen atom, a cyano group, or a nitro group in an organic solvent, and thereby producing an amide acid compound by the following reaction scheme (2):

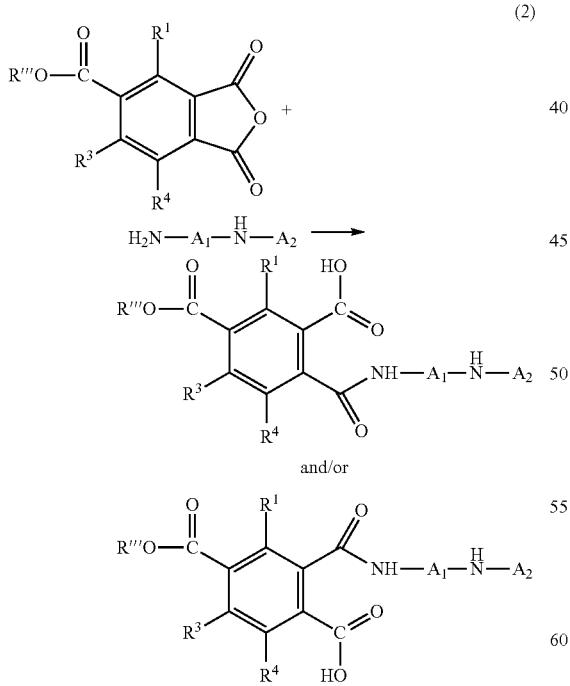

(2)

wherein the symbols used in the reaction scheme (2) respectively have the same meanings as defined above; and Process 3 of heating the reaction solution containing the amide acid compound produced in Process 2, and thereby imidating the amide acid compound by the following reaction scheme (3):

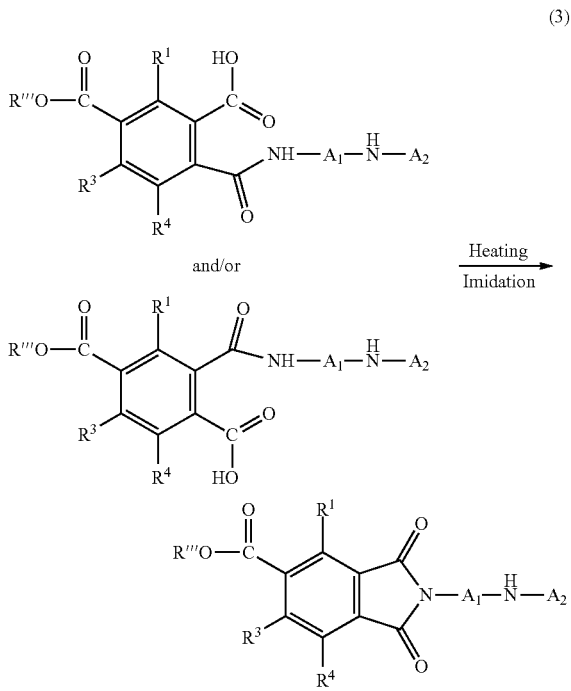

(3)

wherein the symbols used in the reaction scheme (3) respectively have the same meanings as defined above, wherein these three processes are carried out in a one-pot process in the presence of an organic solvent.

7. The method according to claim 6, wherein the amino group-containing diarylamine compound is an aminodiphenylamine compound represented by the following formula (VIII):

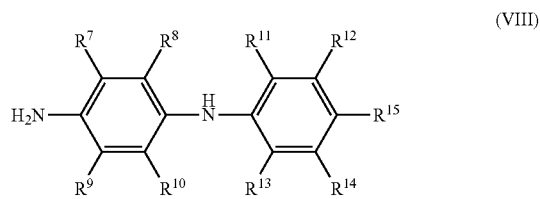

(VIII)

wherein in the formula (VIII), $R^7$ to $R^{15}$ each independently represent a hydrogen atom, an alkyl group having 1 to 10 carbon atoms, a halogen-substituted alkyl group having 1 to 10 carbon atoms, a halogen atom, a cyano group, or a nitro group, and the method comprises three processes represented by the following reaction scheme (1a);

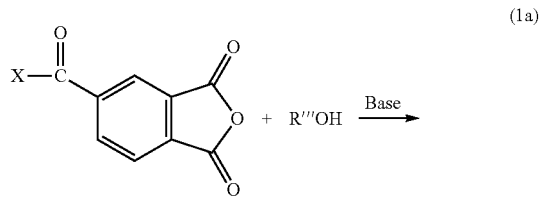

(1a)

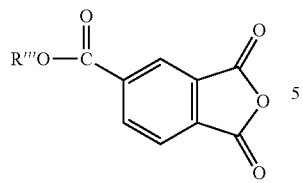
wherein in the reaction scheme (1a), R''' has the same meaning as defined above;
the following reaction scheme (2a);
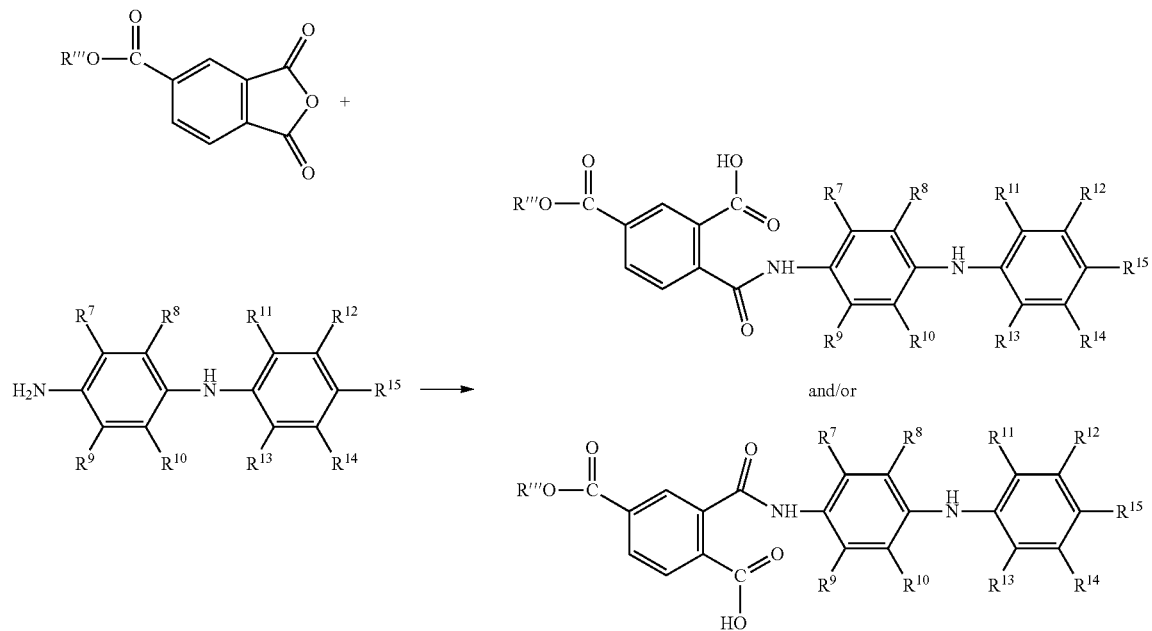
wherein in the reaction scheme (2a),
R''' has the same meaning as defined above, and
$R^7$ to $R^{15}$ respectively have the same meanings as defined above; and
the following reaction scheme (3a);
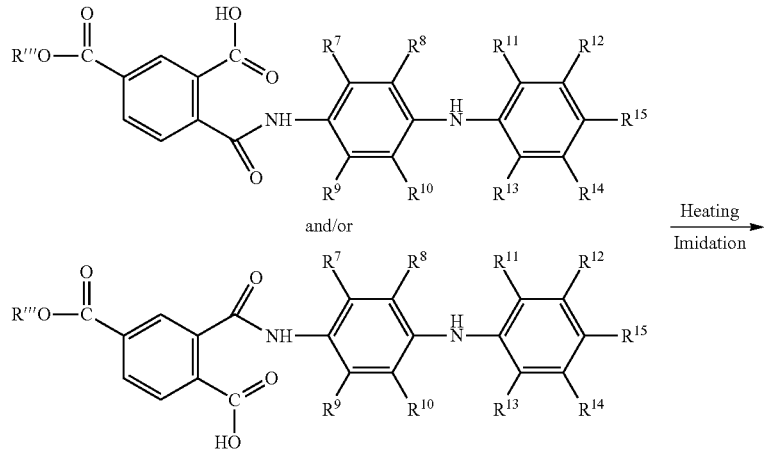

-continued

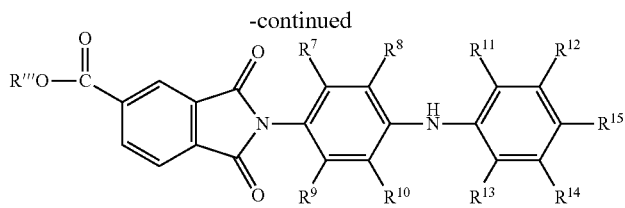

wherein in the reaction scheme (3a), the symbols respectively have the same meanings as defined above, wherein these three processes are carried out in a one-pot process in the presence of an organic solvent, and thereby as a phthalimide group-containing diarylamine compound having an ester group at the 4-position, a phthalimide group-containing diphenylamine compound having an ester group at the 4-position as represented by the following formula (IX):

(IX)

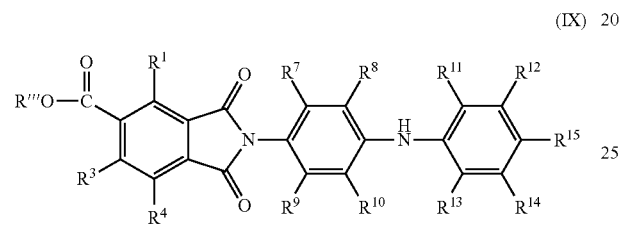

wherein the symbols in the formula (IX) respectively have the same meanings as defined above, is produced.

8. The method according to claim 6, wherein the trimellitic anhydride halide compound is trimellitic anhydride chloride, the amino group-containing diarylamine compound is an aminodiphenylamine compound represented by the following formula (X):

(X)

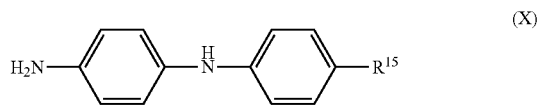

wherein in the formula (X), $R^{15}$ represents a hydrogen atom, an alkyl group having 1 to 10 carbon atoms, a halogen-substituted alkyl group having 1 to 10 carbon atoms, a halogen atom, a cyano group, or a nitro group, and the method comprises three processes represented by the following reaction scheme (1b):

(1b)

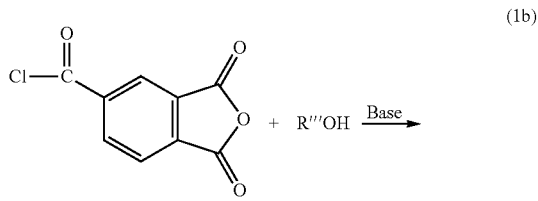

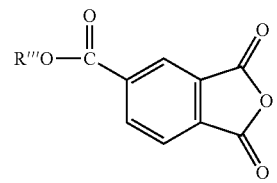

wherein in the reaction scheme (1b), R''' has the same meaning as defined above;

the following reaction scheme (2b):

(2b)

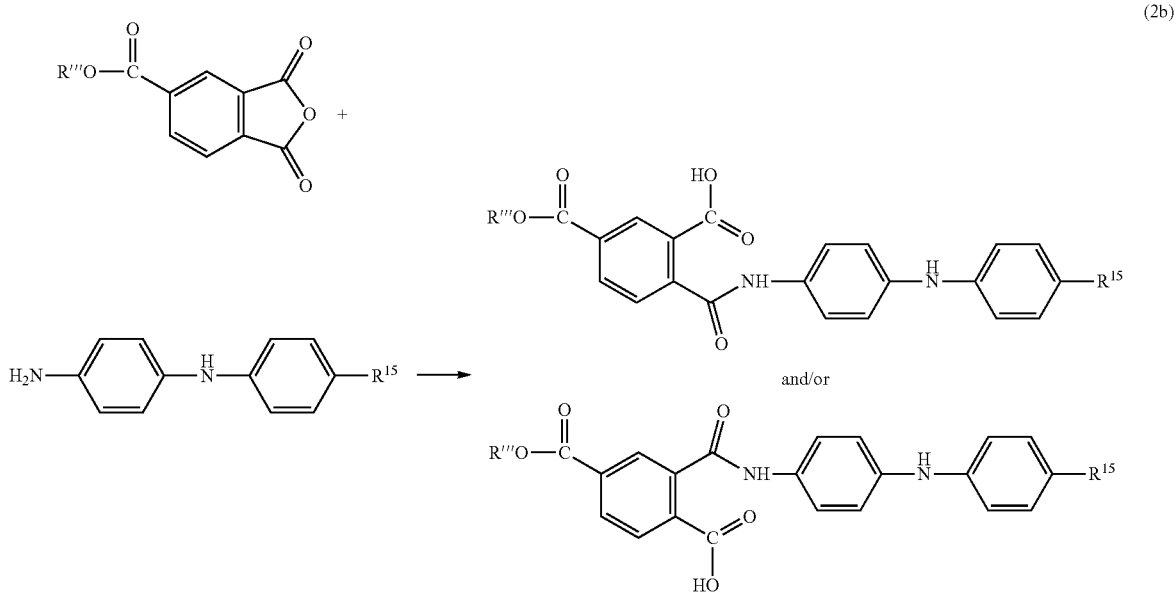

wherein in the reaction scheme (2b), the symbols respectively have the same meanings as defined above; and
the following reaction scheme (3b):

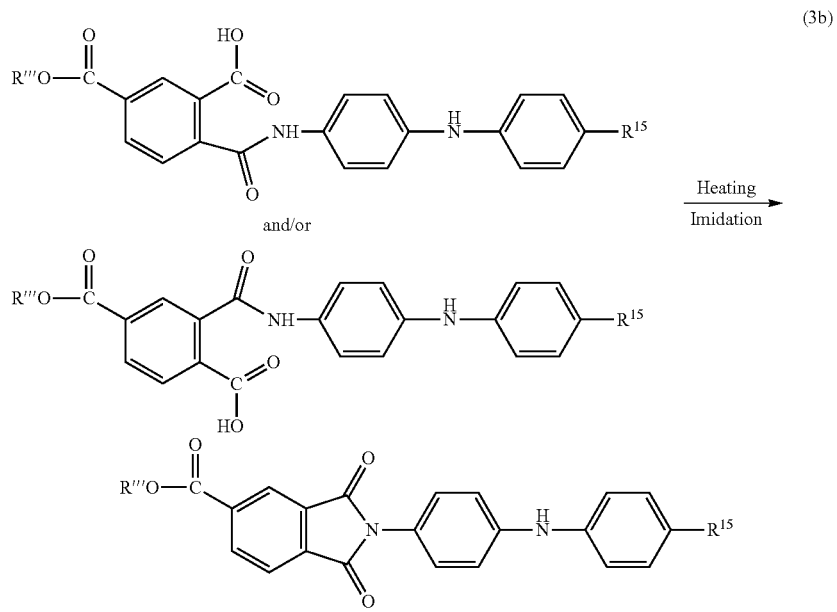

(3b)

wherein in the reaction scheme (3b), the symbols respectively have the same meanings as defined above,
wherein these three processes are carried out in a one-pot process in the presence of an organic solvent, and thereby, as a phthalimide group-containing diarylamine compound having an ester group at the 4-position, a phthalimide group-containing diphenylamine compound having an ester group at the 4-position represented by the following formula (XI):

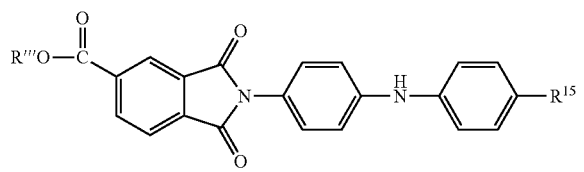

(XI)

wherein the symbols in the formula (XI) respectively have the same meanings as defined above, is produced.

9. The method according to claim 6, wherein the organic solvent is at least one organic solvent selected from the group consisting of an aprotic polar solvent and a non-polar solvent.

10. The method according to claim 6, wherein the organic solvent is a solvent mixture of a nitrogen-containing aprotic polar solvent and an aromatic hydrocarbon-based non-polar solvent.

* * * * *